(12) United States Patent
Lipscher et al.

(10) Patent No.: US 8,301,462 B2
(45) Date of Patent: Oct. 30, 2012

(54) SYSTEMS AND METHODS FOR DISEASE MANAGEMENT ALGORITHM INTEGRATION

(75) Inventors: Randolph B. Lipscher, Austin, TX (US); Eric Wohl, Austin, TX (US); Michael D. Dahlin, Austin, TX (US)

(73) Assignee: Catalis, Inc., Austin, TX (US)

( * ) Notice: Subject to any disclaimer, the term of this patent is extended or adjusted under 35 U.S.C. 154(b) by 772 days.

(21) Appl. No.: 11/857,909

(22) Filed: Sep. 19, 2007

(65) Prior Publication Data

US 2008/0091464 A1    Apr. 17, 2008

Related U.S. Application Data

(63) Continuation-in-part of application No. 10/959,912, filed on Oct. 6, 2004, now abandoned, and a continuation-in-part of application No. 09/992,035, filed on Nov. 23, 2001, now abandoned.

(60) Provisional application No. 60/845,736, filed on Sep. 19, 2006, provisional application No. 60/862,344, filed on Oct. 20, 2006, provisional application No. 60/508,998, filed on Oct. 6, 2003, provisional application No. 60/252,820, filed on Nov. 22, 2000.

(51) Int. Cl.
    *G06Q 50/00* (2006.01)
(52) U.S. Cl. .................................. 705/2; 705/3
(58) Field of Classification Search .................. 705/2, 3
    See application file for complete search history.

(56) References Cited

U.S. PATENT DOCUMENTS

| | | | |
|---|---|---|---|
| 4,839,822 A | 6/1989 | Dormond et al. | |
| 4,858,121 A | 8/1989 | Barber et al. | |
| 4,916,611 A | 4/1990 | Doyle, Jr. et al. | |
| 5,018,067 A | 5/1991 | Mohlenbrock et al. | |
| 5,065,315 A | 11/1991 | Garcia | |
| 5,070,452 A | 12/1991 | Doyle, Jr. et al. | |
| 5,072,383 A | 12/1991 | Brimm et al. | |
| 5,077,666 A | 12/1991 | Brimm et al. | |
| 5,101,476 A | 3/1992 | Kukla | |

(Continued)

FOREIGN PATENT DOCUMENTS

WO          WO 01/33378 A1        5/2001

(Continued)

OTHER PUBLICATIONS

Proquest search result, Jun. 7, 2012.*

*Primary Examiner* — Dilek B Cobanoglu

(57) ABSTRACT

A method of formulating a medical order for a patient includes transmitting a medical order interface to a healthcare provider interface device. The medical order interface includes a plurality of selectable medical order items. The method further includes, in response to receiving a selection of a medical order item of the plurality of selectable medical order items, transmitting an authorization request interface to the healthcare provider interface device. The authorization request interface includes a set of selectable findings controls. Each selectable findings control of the set of selectable findings controls is associated with a set of medical findings associated with the patient. The authorization request interface includes a send control. In addition, the method includes, in response to receiving a selection of a select findings control and receiving selection of the send control, sending an electronic authorization request. The electronic authorization request includes the set of medical finding associated with the select findings control and order data associated with the medical order item.

20 Claims, 61 Drawing Sheets

U.S. PATENT DOCUMENTS

| | | |
|---|---|---|
| 5,265,010 A | 11/1993 | Evans-Paganelli |
| 5,301,105 A | 4/1994 | Cummings, Jr. |
| 5,319,543 A | 6/1994 | Wilhelm |
| 5,347,453 A | 9/1994 | Maestre |
| 5,347,477 A | 9/1994 | Lee |
| 5,361,202 A | 11/1994 | Doue |
| 5,366,896 A | 11/1994 | Margrey et al. |
| 5,390,238 A | 2/1995 | Kirk et al. |
| 5,528,021 A | 6/1996 | Lassus et al. |
| 5,561,446 A | 10/1996 | Montlick |
| 5,594,638 A | 1/1997 | Iliff |
| 5,644,778 A * | 7/1997 | Burks et al. ............... 705/2 |
| 5,660,176 A | 8/1997 | Iliff |
| 5,722,418 A | 3/1998 | Bro |
| 5,737,539 A | 4/1998 | Edelson et al. |
| 5,748,907 A | 5/1998 | Crane |
| 5,758,095 A * | 5/1998 | Albaum et al. ............ 705/2 |
| 5,769,074 A | 6/1998 | Barnhill et al. |
| 5,772,585 A | 6/1998 | Lavin et al. |
| 5,778,882 A | 7/1998 | Raymond et al. |
| 5,845,255 A | 12/1998 | Mayaud |
| 5,868,669 A | 2/1999 | Iliff |
| 5,879,163 A | 3/1999 | Brown et al. |
| 5,883,370 A | 3/1999 | Walker et al. |
| 5,924,074 A | 7/1999 | Evans |
| 5,946,646 A | 8/1999 | Schena et al. |
| 5,951,300 A | 9/1999 | Brown |
| 5,954,641 A | 9/1999 | Kehr et al. |
| 5,960,085 A | 9/1999 | de la Huerga |
| 5,992,890 A | 11/1999 | Simcox |
| 6,018,713 A | 1/2000 | Coli et al. |
| 6,021,202 A | 2/2000 | Anderson et al. |
| 6,024,699 A | 2/2000 | Surwit et al. |
| 6,026,363 A | 2/2000 | Shepard |
| 6,047,259 A | 4/2000 | Campbell et al. |
| 6,055,333 A | 4/2000 | Guzik et al. |
| 6,073,097 A | 6/2000 | Gould et al. |
| 6,073,375 A | 6/2000 | Fant et al. |
| 6,085,752 A | 7/2000 | Kehr et al. |
| 6,090,044 A | 7/2000 | Bishop et al. |
| 6,108,635 A | 8/2000 | Herren et al. |
| 6,113,540 A | 9/2000 | Iliff |
| 6,132,218 A | 10/2000 | Benja-Athon |
| 6,161,095 A | 12/2000 | Brown |
| 6,188,988 B1 * | 2/2001 | Barry et al. ............... 705/3 |
| 6,206,829 B1 | 3/2001 | Iliff et al. |
| 6,208,974 B1 | 3/2001 | Campbell et al. |
| 6,209,095 B1 | 3/2001 | Anderson et al. |
| 6,215,901 B1 | 4/2001 | Schwartz |
| 6,248,063 B1 | 6/2001 | Barnhill et al. |
| 6,298,348 B1 | 10/2001 | Eldering |
| 6,317,789 B1 | 11/2001 | Rakavy et al. |
| 6,347,329 B1 | 2/2002 | Evans |
| 6,385,592 B1 | 5/2002 | Angles et al. |
| 6,454,708 B1 | 9/2002 | Ferguson et al. |
| 6,470,320 B1 | 10/2002 | Hildebrand et al. |
| 6,484,144 B2 * | 11/2002 | Martin et al. ............. 705/2 |
| 6,516,324 B1 | 2/2003 | Jones et al. |
| 6,601,055 B1 | 7/2003 | Roberts |
| 6,609,200 B2 | 8/2003 | Anderson et al. |
| 6,678,669 B2 | 1/2004 | Lapointe et al. |
| 6,839,678 B1 | 1/2005 | Schmidt et al. |
| 2001/0023419 A1 | 9/2001 | Lapointe et al. |
| 2001/0032099 A1 | 10/2001 | Joao |
| 2001/0032124 A1 | 10/2001 | Savage et al. |
| 2001/0041992 A1 | 11/2001 | Lewis et al. |
| 2001/0042064 A1 | 11/2001 | Davis et al. |
| 2002/0019749 A1 * | 2/2002 | Becker et al. ............. 705/2 |
| 2002/0049612 A1 | 4/2002 | Jaeger et al. |
| 2002/0049615 A1 * | 4/2002 | Huber ...................... 705/3 |
| 2003/0018495 A1 | 1/2003 | Sussman |
| 2003/0050801 A1 | 3/2003 | Ries |
| 2003/0195774 A1 | 10/2003 | Abbo |
| 2003/0208465 A1 | 11/2003 | Yurko et al. |

FOREIGN PATENT DOCUMENTS

| | | |
|---|---|---|
| WO | WO 01/35376 A1 | 5/2001 |
| WO | WO 02/33654 A1 | 4/2002 |
| WO | WO 02/42875 A2 | 5/2002 |
| WO | WO 02/42876 A2 | 5/2002 |
| WO | WO 2004/15543 A2 | 2/2004 |
| WO | WO 2004/51415 A2 | 6/2004 |
| WO | WO 2004/51428 A2 | 6/2004 |
| WO | WO 2004/51628 A2 | 6/2004 |

* cited by examiner

| |
|---|
| File Edit View Favorites Tools Help |
| Standard questions/findings: Cardiovascular exam<br><br>  Rhythmn   O Regular   O Irregular<br><br>  Rate   O Normal   O Fast   O Slow<br><br>  Murmur   O Present   O Not Present<br><br>  Grade     O I/VI   O II/VI   O III/VI   O IV/VI   O V/VI   O VI/VI<br><br>  Timing    O Early Systolic   O Mid Systolic   O Late Systolic   O Systolic Ejection   O Holosystolic<br>              O Diastolic   O Early Diastolic   O Mid Diastolic   O Late Diastolic   O Holodiastolic<br>              O Continuous   O Machinery-type<br><br>  Radiation   O Neck   O Axilla   O Base of Heart   O Apex of Heart   O Back   O Diffuse   O Abdomen<br><br>  S2   O   Present   O   Not Present<br><br>  S3   O   Present   O   Not Present<br><br>  S4   O   Present   O   Not Present<br><br>  Rub   O   Present   O   Not Present |
| Disease management questions/findings: Cardiovascular exam<br><br>Dr. Lipscher, the patient's disease management company requests that you please answer these important disease management questions. Thank you.<br><br>Mediastinal crunch    O Present   O Not Present |

RxCare — Randy Lipscher, MD
Patient: Helen Black

Select Patient Northeast clinic

Today's Patients | All Patients

Today's Patients

| Time | Name | ID |
|---|---|---|
| 8:00am | Black, Helen | 3638 |
| 8:15am | Thomas, Mark | 6793 |
| 8:30am | Kulawiec, Rich | 6276 |
| 8:45am | Roehr, Thomas | 6649 |
| 9:00am | Chin, Ian | 1209 |
| 9:15am | Strange, Bill | 4563 |
| 9:30am | Barclay, Alan | 4550 |
| 9:45am | Adams, Simon | 2541 |
| 10:00am | Ferry, Shawn | 8953 |
| 10:15am | Kopack, Mike | 2675 |
| 10:30am | Crawford, Hugh | 3475 |

Find by Last Name: [ ]

A B C D E F G H I
J K L M N O P Q R S
T U V W X Y Z

[Clear]

[Back]

FIG. 25

ReCare — Randy Lipscher, MD
Patient: Helen Black

Message to United Healthcare PPO

Date: 08/08/01
Subject: Reply: Helen Black missed first hospital follow-up visit
Priority: Urgent
To: Ms. Kim Black - United Healthcare Diabetic Case Manager

Reply

☑ Acknowledged
☐ Please address issue with patient
☐ I or my office will address the issue with the patient
☐ Please call me ASAP
☐ Please inform me when issue is addressed
☐ Issue already addressed or resolved
☐ Please assign a Case Manager if not already done
☐ Please enroll patient in compliance education program

SYSTEMS AND METHODS FOR DISEASE MANAGEMENT ALGORITHM INTEGRATION

CROSS-REFERENCE TO RELATED APPLICATION(S)

The present application claims priority from U.S. Provisional Application No. 60/845,736, filed Sep. 19, 2006, entitled "SYSTEMS AND METHODS FOR DISEASE MANAGEMENT ALGORITHM INTEGRATION," naming inventors Randolph Lipscher, Eric Wohl, and Michael Dahlin, which application is incorporated by reference herein in its entirety.

The present application claims priority from U.S. Provisional Application No. 60/862,344, filed Oct. 20, 2006, entitled "SYSTEM AND METHOD FOR EXPRESSION OF PREFERRED ORDERS," naming inventors Randolph B. Lipscher, Michael D. Dahlin, and Eric Wohl, which application is incorporated by reference herein in its entirety.

The present application claims priority from U.S. Non-Provisional application Ser. No. 10/959,912, filed Oct. 6, 2004, entitled "SYSTEM AND METHOD FOR EXTERNAL INPUT OF DISEASE MANAGEMENT ALGORITHMS," naming inventors Randolph B. Lipscher, Michael D. Dahlin, and Eric Wohl, which claims priority from U.S. Provisional Application No. 60/508,998, filed Oct. 6, 2003, entitled "SYSTEM FOR EXTERNAL INPUT OF DISEASE MANAGEMENT ALGORITHM AND INTEGRATION OF ALGORITHM AT POINT OF CARE," naming inventors Randolph B. Lipscher and Michael D. Dahlin, and which is a continuation-in-part of and claims priority from U.S. patent application Ser. No. 09/992,035, filed Nov. 23, 2001, entitled "SYSTEM AND METHOD FOR INTEGRATING DISEASE MANAGEMENT INTO PHYSICIAN WORKFLOW," naming inventors Michael D. Dahlin, Eric Wohl, Randolph B. Lipscher, and Charles Andrew Bergman, which claims priority to U.S. Provisional Application No. 60/252,820, filed Nov. 22, 2000, entitled "SYSTEM AND METHOD FOR INTEGRATING DISEASE MANAGEMENT INTO PHYSICIAN WORKFLOW," each of which applications are incorporated by reference herein in its entirety.

FIELD OF THE DISCLOSURE

This disclosure, in general, relates to systems for external input of disease management algorithms and integration of algorithms at points of care.

BACKGROUND

Healthcare costs are increasing and, as a result, payers, such as government agencies and insurance companies, are seeking to reduce costs. Government agencies, such as Medicaid and Medicare, are experiencing large increases in expenditures. Insurance companies are also experiencing cost pressures and are increasing policy rates.

In many cases, payers have implemented rules and conditions under which they will pay for a procedure or examination. In addition, these payers have developed disease management programs to manage disease treatment and prevent or mitigate expensive consequences to manageable diseases, such emergency room visits and hospitalization.

However, insurance companies, government agencies, and other organizations associated with health services have difficulty communicating with physicians. Physicians generally have greater access to the patient. When physicians lack information about a payers rule or a specific patients disease management program, they may not conform to the rules or guide the patient's compliance with the disease management program. As such, an improved system for providing input of disease management algorithms to disease management systems and integrating the algorithms into physician workflow would be desirable.

BRIEF DESCRIPTION OF THE DRAWINGS

The present disclosure may be better understood, and its numerous features and advantages made apparent to those skilled in the art by referencing the accompanying drawings.

FIGS. 13, 14, and 15 include general diagrams illustrating exemplary interfaces for use in a medical workflow.

FIGS. 18-29 include general diagrams illustrating exemplary interfaces for use in a medical workflow.

FIGS. 30-54 include illustrations of exemplary interfaces for use in a medical workflow.

FIGS. 56-66 include illustrations of exemplary interfaces for use in a medical workflow.

The use of the same reference symbols in different drawings indicates similar or identical items.

DESCRIPTION OF THE DRAWINGS

In one particular embodiment, the disclosure is directed to a system including a disease management advisor system configured to communicate with a healthcare provider system. The disease management advisor system transmits a disease management algorithm to the healthcare provider system. The disease management algorithm is converted or mapped to a controlled medical vocabulary for use by the healthcare provider system in providing an interface for entry of medical information. For example, the interface may include control elements for entering patient medical information. In one particular embodiment, the interface is configured based on the disease management algorithm.

In one exemplary embodiment, the disease management algorithm includes a set of rules that determine when the algorithm is applicable and includes data associated with the action resulting from application of the disease management algorithm. The disease management algorithm may also include information regarding in which HCP systems it should be implemented. For example, a formulary disease management algorithm may include rules that direct implementation of the algorithm when a specific drug is prescribed or when a prescription interface is displayed in conjunction with a patient examination that reveals a particular set of findings. Such a formulary algorithm may be implemented in all HCP systems associated with a particular disease management advisor. In another exemplary embodiment, a patient-based disease management algorithm may be implemented to display a particular text message when a particular patient visits a physician. In such an example, the algorithm would be sent only to HCP systems associated with the treatment of the particular patient. In general, the disease management algorithm is interpreted to configure interfaces provided by the HCP system.

Figure 1:
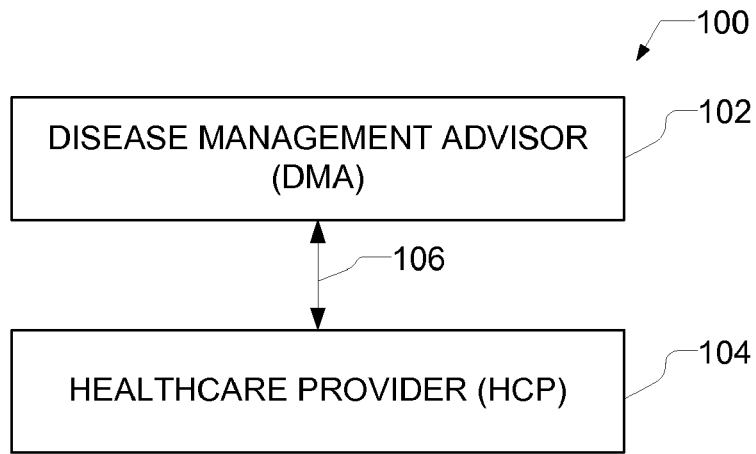
FIGS. 1, 2 and 3 include diagrams illustrating exemplary disease management systems.

FIG. 1 shows the top-level system architecture. The system 100 comprises at least one Disease Management Advisor (DMA) system 102, at least one Health Care Practitioner (HCP) system 104, and at least one network 106 connecting these systems.

A disease management advisor system 102 is a system used by one or more disease management advisors. A disease management advisor (DMA) includes an entity that advises one or more health care providers regarding treatment of patients. Examples of disease management advisors include specialized disease management advising companies, pharmacies, insurance companies, government agencies, medical professional societies, medical specialists, experts in particular fields of medicine, pharmacy benefits management companies, pharmacy advertisers, pharmacies, labs, research institutions, organizers of medical studies, and organizers of medication trials.

A health care practitioner system 104 or a healthcare provider system is a system used by one or more health care practitioners. A health care practitioner (HCP) is an entity that participates in the examination, evaluation, or treatment of medical patients. Examples of health care practitioners include medical doctors, nurses, nurse practitioners, clinic administrative staff, technicians, pharmacologists, pharmacy workers, medical students, and medical assistants.

In an exemplary embodiment, the "HCP system" and "DMA system" roles may both be played by the same entity at different times. Generally, an HCP is an entity that executes examination, evaluation, or treatment of a patient. Generally, a DMA is an entity that advises about health care decisions. Often, a doctor acts as an HCP and an HMO acts as a DMA. In alternative embodiments, an HMO acts as the HCP (e.g., approving a treatment) while a doctor acts as a DMA (e.g., recommending a treatment). In some exemplary embodiments, a patient acts as an HCP (e.g., administering a medication) while a doctor acts as a DMA (e.g., providing information about a medication's side effects.) In a further example, a patient acts as a DMA (e.g., requesting a medication refill) and the doctor acts as an HCP (e.g., ordering a medication refill).

In an exemplary embodiment, the computer network 106 includes the Internet and the DMA systems and HCP systems are physically separate computer systems. In another exemplary embodiment, the computer network 106 is a shared memory system through which DMA and HCP systems resident in the same physical computing system communicate.

In an exemplary embodiment, the computer network 106 includes an encryption module and the system uses the encryption module to authenticate communication and to prevent third parties from being able to read information. In this embodiment, authentication ensures that DMA systems and HCP systems know the identity of the systems with which they communicate or the identity of the users of those systems, and the DMA and HCP system restrict access to system functionality based on the identity of the system or user requesting an action. Encryption may be accomplished using algorithms known to practitioners skilled in the art, such as DES, IDEA, Blowfish, and RSA. Authentication may be accomplished using algorithms known to practitioners skilled in the art, such as Kerberos, PGP, public key cryptography, SDSI, and SPKI.

Figure 2:
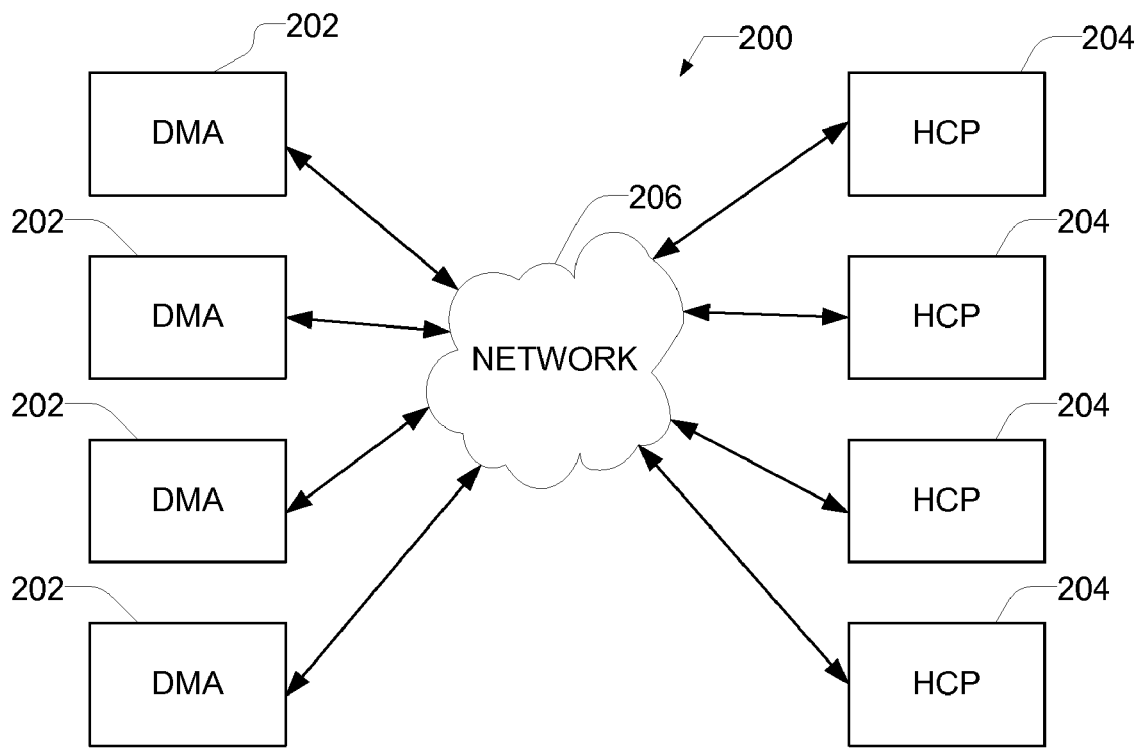

In a particular embodiment, each DMA system 202 communicates with multiple HCP systems 204 and each HCP system 204 communicates with multiple DMA systems 202 through a network 206, as illustrated in FIG. 2. Each of the DMA systems 202 and HCP systems 204 may include a transmission module that permits addressing and transmission of data and disease management algorithms between systems. In an alternative embodiment, a central transmission system may receive the disease management algorithms from each of the systems and determine to which system the disease management algorithm is to be transferred.

Figure 3:
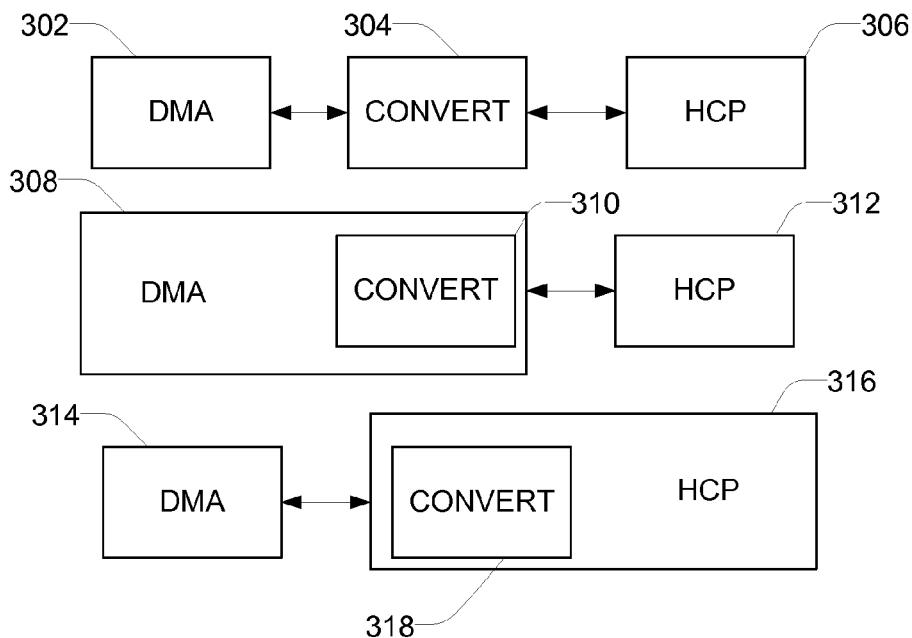

As FIG. 3 illustrates, the system may also include a conversion module, such as conversion modules 304, 310, and 318. Typically, the HCP system, such as HCP systems 306, 312, and 316, may manipulate and store medical data that describes medical conditions using a controlled medical vocabulary. A controlled medical vocabulary defines a unique word or identifier to each unique significant medical concept. Synonyms or other phrases describing the same concept are mapped to the controlled medical vocabulary's identifier. For example, a controlled medical vocabulary might map "elevated temperature", "feels warm", and "fever" to the term "fever" or, in another embodiment, to unique number, such as 284751. Exemplary controlled medical vocabularies include SNOMED-CT (Systematized Nomenclature of Medicine—Clinical Terms), ICD9-CM, LOINC (Logical Observation Identifiers Names and Codes), READ, and UMLS (Unified Medical Language System). In an embodiment, one or more DMA systems, such as DMA systems 302, 308, and 314, may use different controlled medical vocabularies from the controlled medical vocabulary used by the HCP system, such as HCP systems 306, 312, and 316. In addition, the HCP systems (e.g. 306, 312, and 316) may use different controlled medical vocabularies from each other. In this embodiment, a conversion module (i.e. 304, 310, and 318) translates rules specified at a DMA system using the DMA's controlled medical vocabulary to rules executed at the HCP system using the HCP's controlled medical vocabulary. In one embodiment, this conversion module includes a mapping from each term in a DMA's controlled medical vocabulary to a mapping in the HCP's controlled medical vocabulary and translates each instance of a term from the former into a term from the latter.

In one embodiment, a DMA system may specify rules without using a controlled medical vocabulary. In such an embodiment, the conversion module translates from the set of terms or phrases that refer to a concept to the concept in the HCP's controlled medical vocabulary. In one embodiment, this translation comprises a human expert reading the DMA rule and converting it to a rule in the HCP system's controlled medical vocabulary. In another embodiment, this translation is done automatically using, for example, the method described by Kornai and Stone (Andras Kornai and Lisa Stone, "Automatic Translation to Controlled Medical Vocabularies" in A. Abraham and L. Jain (eds): Innovations in Intelligent Systems and Applications Springer Verlag, 2004, 413-434), included herein by reference.

As FIG. 3 illustrates, the conversion occurs between arrival of data at the DMA system and display of data at the HCP system, but the system may be constructed with this conversion occurring at various places. For example, this conversion may occur after the algorithms have been sent by the DMA and before they are received by the HCP (e.g., conversion may occur at a data center through which the DMAs and HCPs communicate.) Alternatively, this conversion may occur within the DMA system, as illustrated by DMA system 308 and conversion module 310. In another example, this conversion may occur within the HCP system, such as HCP system 316 having conversion module 318.

Figure 4:
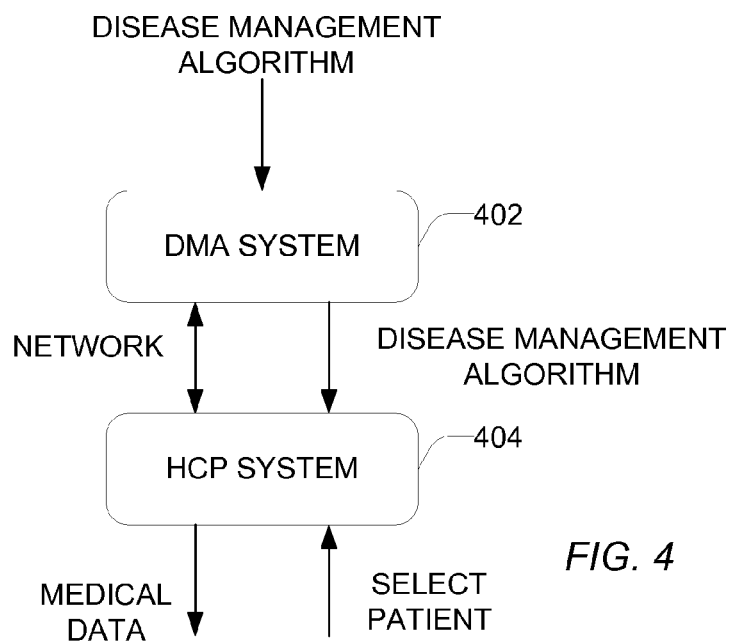
FIGS. 4 and 5 include flow diagrams illustrating exemplary methods for using disease management systems, such as those illustrated in FIGS. 1, 2, and 3.

FIG. 4 depicts four data flows in the system. The disease management advisor system 402 receives one or more disease management algorithms and, in one embodiment, stores the algorithms. The disease management advisor system transmits the one or more disease management algorithms across the network to one or more health care practitioner systems 404, which store the one or more algorithms. The health care practitioner system 404 receives medical inputs including a directive to select a patient. The health care practitioner system displays medical data, the contents of which depend upon both the patient selected and at least one of the disease management algorithms received.

Figure 5:
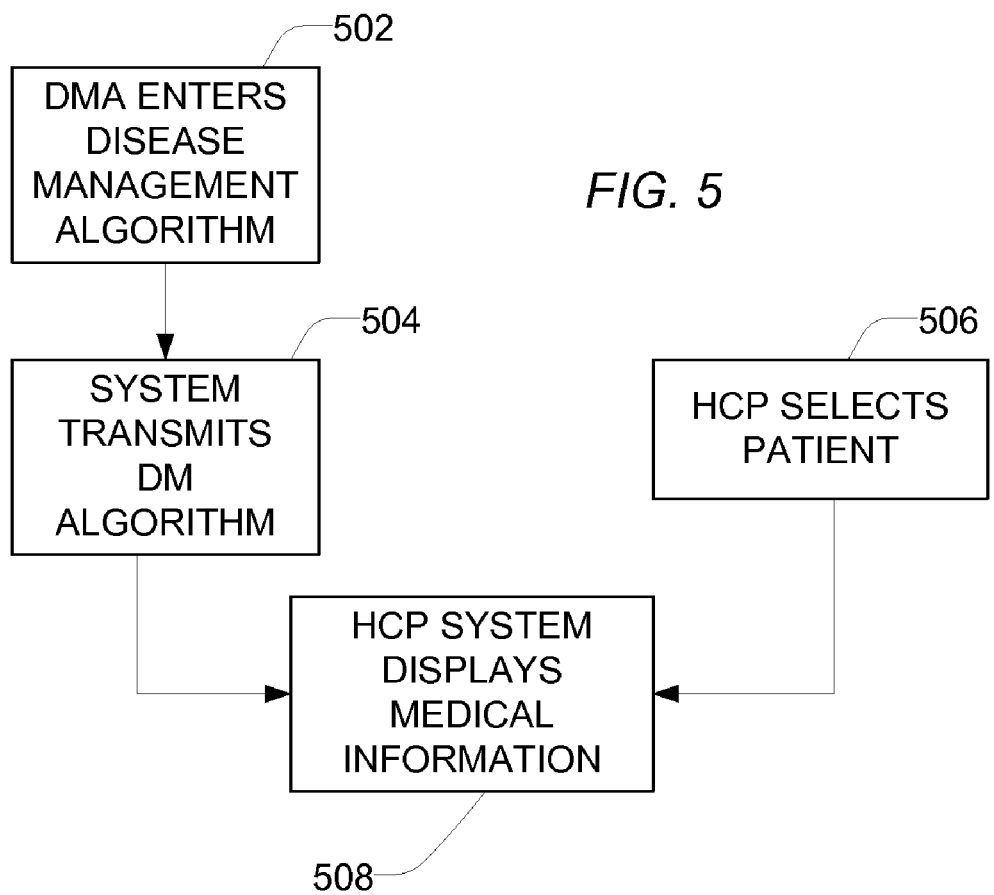

FIG. 5 indicates a flow chart of actions relating to these flows of data. A DMA enters at least one disease management algorithm into a DMA system, as shown at step 502. After the entry of the at least one disease management algorithm, the network transmits the at least one disease management algorithm from a DMA system to an HCP system, as shown at step 504. An HCP selects a patient at the HCP system, as shown at step 506. After the HCP selects a patient, the HCP system displays medical data specified by the disease management algorithm for the selected patient based on the algorithm's operation on medical data associated with the selected patient, as shown at step 508. Note that the selection of the patient may precede or follow the network transmission of the at least one algorithm.

One can envision various methods by which an algorithm can analyze the records associated with a selected patient in order to specify medical information to be displayed. In one embodiment, the disease management algorithm specifies one or more selection conditions and specifies medical data. The HCP system displays an algorithm's medical data when the selection conditions specified in the algorithm are satisfied by the record associated with the selected patient.

Medical data include data relating to medical treatment. Examples include findings, medical reference information, medical journal articles, best practice recommendations or guidelines, alerts about a patient, information about a medical condition, information about a doctor, recommended questions, recommended actions, forms, approval of medical orders, medications or tests, orders for medications, treatments or tests, medical coding information, changes to existing templates or forms, and the like. A finding is information about a particular medical patient. Examples of such information include: demographic information (such as the patient's age, gender, address, or occupation), symptom information, disease process information, medical history information, family history information, behavioral information (such as patient alcohol consumption or smoking status), medication, genetic information, allergy information, reaction information, current medication or treatment information, past medication or treatment information, payer information (such as insurance company or pharmacy benefits management company), and other observations of or information about a patient. Note that findings are a particular category of medical data.

A selection condition specifies conditions for which medical data should be displayed. These conditions are based on one or more factors. In one embodiment, these factors include at least one medical finding about the currently selected patient. In another embodiment, the selection condition also includes at least one factor regarding other information about the selected patient (e.g., the patient's payer or home address), information about the HCP user (e.g., the user's specialty, identity), or the current task being performed by the HCP system (e.g., displaying Review of Systems template, prescribing medication, ordering MRI). A selection condition includes a function taking factors as input. Example functions include Boolean functions, a numerical function, numerical range comparisons, database queries, string regular expressions, computer program functions, and combinations of these types.

To illustrate examples of selection conditions: a selection condition may specify that medical data be displayed (1) when a particular HCP selects a particular patient and begins the view current messages task, (2) when any HCP selects any patient that has a particular condition, (3) when any HCP selects any patient enrolled in a particular insurance plan, or (4) when any HCP selects any patient enrolled in a particular insurance plan and who has a particular condition and the current HCP task associated with the patient is the prescribe medication or request medical order task.

In one embodiment, each disease management algorithm specifies one or more selection conditions and specifies at least one from a list of standard system response actions. The HCP system activates the response action when the selection conditions specified in the algorithm are satisfied by the record associated with the selected patient. In one embodiment, one or more of the disease management algorithms also may include medical findings. In this embodiment, the HCP system activates the response action using the medical findings as arguments or modifiers to the response action when the selection conditions specified in the algorithm are satisfied by the record associated with the selected patient.

System response actions are "hooks" in the HCP system for altering or augmenting the behavior of the HCP system. By specifying the disease management algorithms in terms of a relatively short list of standard actions, a general and extensible framework can be constructed that allows a broad range of different DMA entities to specify a broad range of modifications to the base HCP system.

For example, the standard system response actions may include at least one of:

(1) Prompt the user for more information. An algorithm that includes this action also specifies a medical findings template that is to be displayed. This template provides input elements or controls (e.g., checkboxes, tri-state boxes that can be marked "positive", "negative" or "unmarked", text input fields, etc.) with each entry tied to a specific finding in the HCP system's controlled medical vocabulary. When such a template is displayed, the state of the inputs is initialized according to the current patient's electronic medical record as stored in the HCP system (e.g., when the user checked the box for "difficulty swallowing" on the Physical Exam page and then the response action displays a template that includes a "difficulty swallowing" field, the field appears in the checked state). Also, when updates are made to the displayed template, these updates are propagated back to the standard HCP template display (so that when the user unchecks "difficulty swallowing" in the displayed template and then views the standard Physical Exam template, the "difficulty swallowing" box appears unchecked.

(2) Send a message to an external entity. An algorithm that includes this action also specifies one or more medical findings from the patient's record to be sent and a destination to which this information should be sent. For example, an algorithm may specify that whenever a patient insured by Blue Cross is diagnosed with diabetes, that patient's name, contact information, diagnosis, chief complaint, history of present illness, review of systems, physical exam, current medication, and past medical family and social history be sent to a disease management nurse who is to contact that patient to coordinate that patient's care. Destinations are specified using addresses, such as email addresses or DMA system specific addresses, or user IDs from the HCP and DMA systems. Note that confidentiality of medical information is important. Embodiments may protect confidentiality in two ways. First, before any information is sent, the user (typically the physician treating the patient) may be notified of the destination and the information being sent, and the user is prompted to approve transmission before it is sent (or decline transmission to cancel it.) Second, the system may include a set of rules restricting transmission of information about a patient to specific destinations. For example, in a given HCP system transmission might be permitted to healthcare workers in the clinic, specialists allied with the clinic or the patient's plan, the patient him/herself, the patient's guardian, or the patient's payer.

In another embodiment, transmission to researchers and government agencies is supported by stripping any personally identifying information from the list of findings to be transmitted for algorithms that specify such an entity as the recipient. Additionally, such transmission may pass through a delay aggregator that collects a number of records and or delays transmission of such records in time before sending them to the destination.

(3) Display information. An algorithm that includes this action also specifies the information to be displayed. For example, this information could include a recommendation for best-practice treatment (e.g., "Antibiotic X is more effective than antibiotic Y for condition Z"), an advertisement, prescribing information, summaries of recent related clinical studies, a warning (e.g., "medication X is contra-indicated for the current patient because the patient has finding Y", or "Mr. Jones [the current patient] is allergic to medication class Z") or opportunities to enroll patients in medical trials. This information can include text, graphics, and references such as URLs that can be clicked on to display additional information.

(4) Display a dialog. A dialog includes information of the types listed above for display information. However, the dialog response may solicit explicit action by the user (e.g., click "ok") in order to force the user to take some action (or to acknowledge) the information.

(5) Payer approval. This action specifies a list of findings and a set of rules across those findings that must be satisfied for automatic approval of a procedure, medication, or order. When a payer approval action is triggered, the system displays the findings (along with their current states from the patient's record) and allows the user to update these findings on the on-screen template. If the state of the findings satisfies the criteria, a message to that effect is displayed. The user can select "done," for example, if the treatment is automatically approved or if the user chooses not to proceed with the approval process. Alternatively, the user can select "request override". The action specifies an approval agency and a set of findings to be sent to the approval agency, and when the user requests an override, this information is displayed and the user also may (1) enter (in text or via voice dictation) additional comments and (2) select additional parts of the patient's record (e.g., the physical exam, review of systems, etc.) to include in the transmission. When the user selects send, the information is sent to the approving entity.

In one embodiment, the transmission includes a capability allowing the approving agency to transmit electronically an approval number that the HCP system binds to the current patient's current encounter record. In another embodiment, the approving agency inserts a new algorithm into the system specifying that a message indicating approval be displayed when the current user selects the current patient and either views the current encounter record or views the messages task.

(6) Highlight. This action specifies a particular finding that appears on the screen that is currently being displayed by the HCP system when the algorithm is triggered. The HCP system may realize this action by highlighting on screen the specified finding. This action can, for example, allow a pharmacy benefit management company to highlight a medication on a list of medications because that medication is both on-formulary for the patient and conforms to best-practice guidelines for the patient's condition.

(7) Preselect. This action specifies that a particular finding that appears on the screen be set to the selected state. For example, the algorithm specifies that for a patient with condition X, a blood test of type Y be ordered if no order for test Y appears in the patient's record for the past year. In one embodiment, algorithms of this type are restricted to (a) only work on findings that correspond to orders (e.g., not physical exam findings or HCP findings) and (b) only findings that appear on the current screen (e.g., the algorithm can not change the state of a finding that is invisible to the user.)

It will be apparent to those skilled in the art that other system responses can be defined. For example, a system response that combines attributes from the above responses could be defined.

Referring back to FIG. 3, in one embodiment, in addition to converting rules between vocabularies, the conversion module converts a DMA's rules from a list or table of criteria to the system's disease management algorithm format. For example, the United States Government currently publishes tables of criteria that must be met in order for specific medical procedures, orders, medications, or billing codes to be authorized. For example, such a table may specify that Hospice Care may be ordered (and paid for by a specific government program) when the patient is expected to live fewer than 6 months. The conversion module maps this table of rules to specific conditions (e.g., a finding that corresponds to one or more controlled medical vocabulary elements corresponding to "patient not expected to survive 6 months"—e.g., a single code for that concept, or any of a group of codes including specific diagnoses where the standard prognoses is that the patient will die within 6 months if the disease runs its expected course) and to specific actions (e.g., when "hospice care" is selected as an order and the condition is not met, display a warning to the user.)

In one embodiment, the system (1) downloads a set of rules, (2) converts these rules to one or more disease management algorithms specifying (a) at least one selection rule operating on a medical finding element specified by a controlled medical vocabulary identifier and (b) at least one action to be taken, (3) receives a patient selection from a user, (4) evaluates the selected patient's medical record under the selection rule, and (5) depending on the result of the evaluation of the selection rule, takes the specified action or takes some other action. (Note that the latter case includes taking no action.) In one embodiment, the rules downloaded from the public Internet may be specified using a different controlled medical vocabulary than the selection rules used internally by the system.

Figure 6:
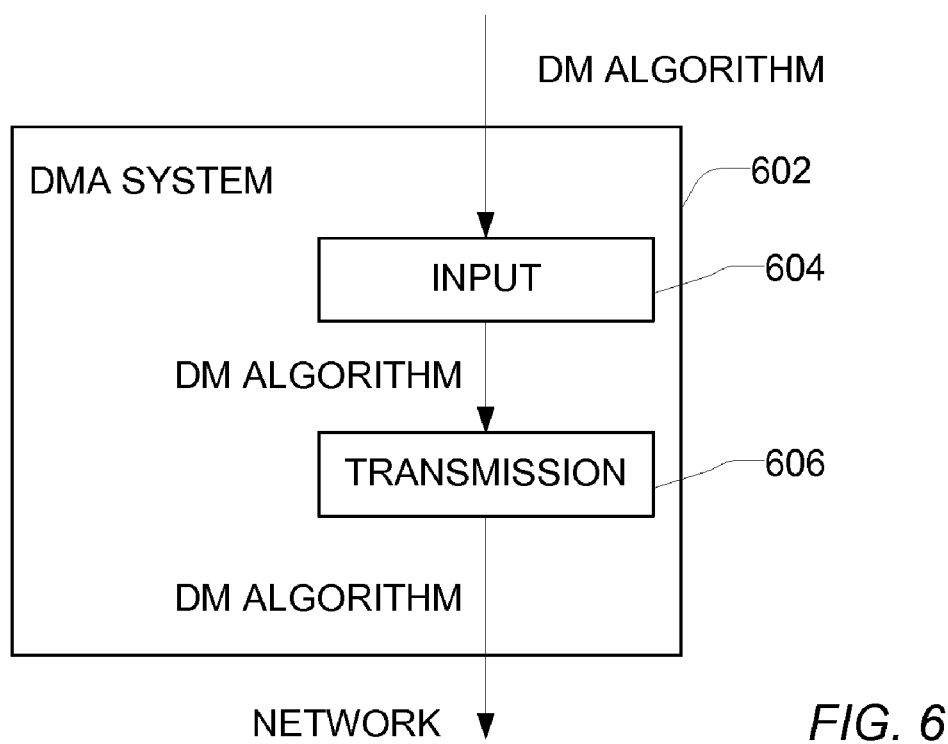
FIGS. 6 and 7 include diagrams illustrating exemplary disease management advisor systems.

As illustrated in FIG. 6, in an exemplary embodiment, the disease management advisor system 602 provides an interface 604 for input of one or more disease management algorithms and an interface or module 606 for transmission of these one or more algorithms across a network to one or more HCP systems. The DMA system receives as input one or more disease management algorithms via the input interface 604 and sends one or more disease management algorithms to one or more HCP systems using a network via the transmission module 606.

Figure 7:
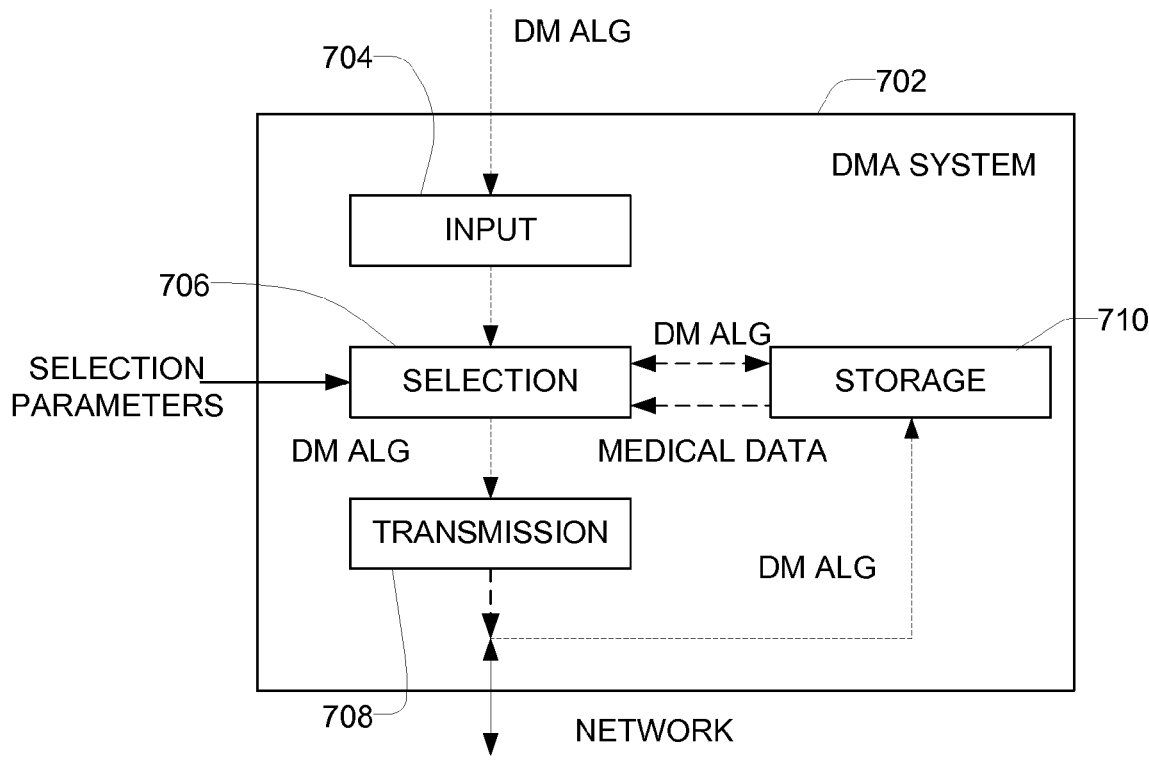

The algorithms may be sent to one HCP system, a subset of HCP systems, or all HCP systems. In one embodiment, illustrated in FIG. 7, the DMA system also includes a selection module 706 that chooses to which HCP systems a particular algorithm should be sent.

In this embodiment, the selection module 706 makes use of a storage module 710, such as DRAM memory, disk, a database, or a file system. In one embodiment, the storage module 710 stores information relevant to the selection conditions in one or more algorithms. For example, in one embodiment, the storage module 710 stores information about patients, such as which patients are treated by which HCPs or such as patient findings. For example, in one embodiment, the storage module 710 stores the current task being performed by an HCP using a particular device, which allows relevant disease management algorithms to be transmitted to an HCP system while the HCP system is being used to treat a particular patient. In another embodiment, the storage module 710 stores information about a particular clinic or user that uses the HCP system. For example, in one embodiment the storage module 710 stores information about HCP devices, such as which HCP devices are used by which HCPs or which insurance plans an HCP user is counted as a primary care physician.

In this embodiment, the DMA system 702 may receive as input one or more disease management algorithms via an input interface 704 and may receive as input one or more selection criteria and may send one or more disease management algorithms to one or more HCP systems using a network connected to transmission module 708. In this embodiment, the set of disease management algorithms sent to a given HCP system depends on applying the selection criteria to characteristics of the HCP system or medical information about one or more patients served by the HCP system or on both.

Figure 8:
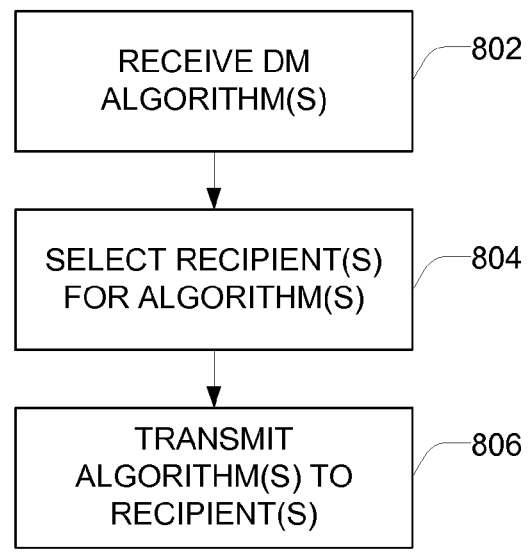
FIGS. 8, 9, 10, 11, and 12, include flow diagrams illustrating exemplary methods for use by disease management systems, such as those illustrated in FIGS. 1, 2, and 3.

FIG. 8 illustrates an exemplary flow of actions performed by an exemplary DMA system. The system may receive one or more input algorithms, as shown at step 802, may select destinations to which these algorithms are sent, as shown at step 804, and may transmit these algorithms, as shown at step 806.

In one embodiment, the storage module used by the selection module receives medical data from the HCP device. For example, the HCP device may use a network to transmit the list of HCPs registered to access the device, the list of patients treated by users of the device, and findings about patients. The DMA system receives and stores this information.

Figure 9:
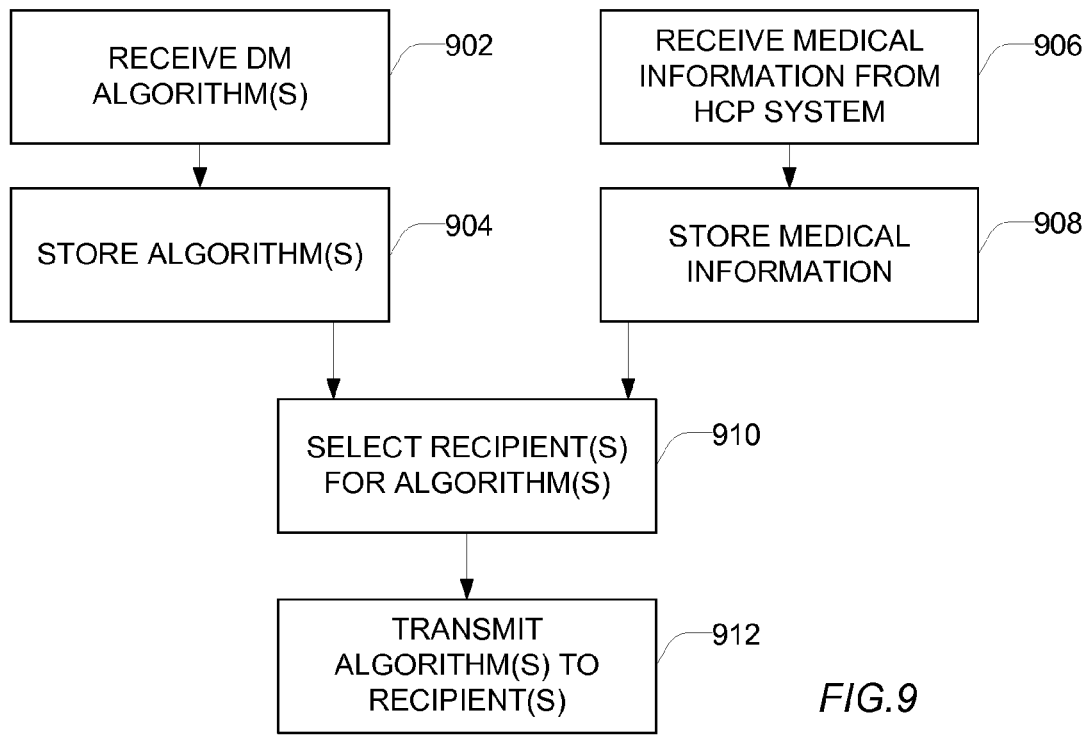

FIG. 9 illustrates an exemplary flow of actions performed by an exemplary DMA system. The system may receive and store one or more input algorithms, as shown at steps 902 and 904, and the system may receive and store one or more medical data elements, as shown at steps 906 and 908. The system may select recipients for algorithms based on selection conditions in the algorithm applied to stored medical data, as shown at step 910. The system may send the algorithms to the selected recipients, as shown at step 912. Note that in this exemplary embodiment, selection and transmission of algorithms may be triggered by arrival of either an algorithm or of medical data. For example, the system may receive one algorithm, and transmit that algorithm whenever it receives medical data indicating that a new patient matches the selection criteria for that algorithm.

The input interface provides algorithms to the DMA system. For example, the input interface may be a keyboard, mouse, touch screen, graphic user interface, another computer, another program or stored information, among others.

The data entered via the input interface specifies one or more disease management algorithms. In an exemplary embodiment, the input interface may include a method to input one or more selection condition specifiers, such as the identity of an HCP recipient, the identity of a patient, a set of findings to match, or a task performed by the HCP using the HCP system. In an exemplary embodiment, the input method also may include a method to input one or more medical data items, such as a message, form to be filled out, alert to be displayed, or modification to be made to an examination template. The input method processes the data received and generates an algorithm data structure in a machine-readable form such as XML, an in-memory data object, HTML, formatted text, a database record, or the like.

In one exemplary embodiment, the input method includes a Graphical User Interface (GUI) display modeled on a typical HTML-based web-based email service. However, where a typical HTML-based web-based email interface provides a "To:" field in which the email address of a user is specified, the Input GUI of the exemplary disease management system includes a field for specifying a patient ID and one for specifying an HCP ID. In one particular embodiment, these fields may include the option to specify that a disease management algorithm apply to all patients or all HCPs. Where a typical HTML-based web-based email interface provides a text input area, the GUI also includes an area for entering a text message. The interface may alternatively include a field for entering selection criteria. Where a typical HTML-based web-based email interface provides a button to send the message, the input elements provides a button to send the algorithm.

In this exemplary embodiment, the user enters a patient ID, HCP ID, and message and activates the send button. The input method processes the field inputs to assemble an XML record in which the patient ID and HCP ID are selection condition items indicating that the algorithm pertains to the patient P and HCP H specified in the corresponding GUI fields and in which the text message M from the text GUI field is included as medical data. In one exemplary embodiment, this algorithm is interpreted to mean "when HCP H selects patient P, display message M".

In a second exemplary embodiment, the input method includes a text editor such as emacs, Microsoft Notepad, or vi with which a user specifies algorithms as XML data files. Input is accomplished by signaling the disease management advisor system to load one or more specified data files from local storage or from across a network.

The transmission module transmits algorithms to one or more HCP systems. In one embodiment, all algorithms are transmitted to all HCP systems. In another embodiment, algorithms to be transmitted include a list of HCP systems to which they are to be transmitted. In one embodiment, transmission is immediate. In another embodiment, the transmission module stores the messages to be transmitted and transmits them at a later time.

The transmission module uses a network protocol to deliver data to the remote HCP system. Algorithms embodying such protocols are known to those skilled in the art, such as HTTP, TCP, RPC, and shared memory. In an exemplary embodiment, the transmission is accomplished using a protocol that encrypts transmitted data such as SSH, SSL, or DES over TCP. Although the system can be implemented by transmitting all algorithms to all HCPs or by requiring the DMA user to explicitly specify specific HCPs that should receive specific messages (as illustrated in FIG. 6), an exemplary embodiment (illustrated in FIG. 7) also includes a selection module that selects which HCP systems should receive each algorithm.

In one embodiment, the algorithms are be transmitted soon after they are received by the DMA system. In this embodiment, the system receives a disease management algorithm, selects a set of HCP systems to which the algorithm should be sent by comparing the algorithm's selection conditions to the stored information. The system then sends the algorithms to the selected HCP systems.

For example, the system could receive an algorithm specifying that a specified message be displayed when any HCP is treating a patient that is enrolled with a particular insurance company and that is diagnosed with diabetes. In this case, the exemplary selection module sends the algorithm to all HCP systems.

In another example, the system can receive an algorithm specifying that all HCP's treating a particular patient should be informed that that patient has recently missed an appointment for diabetes management program meeting. The exemplary selection module reads from the storage module to determine the list of HCP systems used by HCPs that treat the specified patient and sends that algorithm to that list of HCP systems.

In a further example, the system can receive an algorithm specifying a message containing the results of a test on a particular patient that was ordered by a particular HCP. The exemplary selection module sends the algorithm to the HCP system used by that HCP.

In another embodiment, the algorithms are stored and transmitted at a later time. When the algorithms are stored and transmitted at a later time, factors that select when an algorithm is transmitted include factors such as time of day, elapsed time since the algorithm was stored, receiving a request from an HCP system, receiving medical data that trigger a match with the algorithm. For example, in order to prevent data transfers from interfering with other system activities, the DMA system may store algorithms to be sent to an HCP and deliver them in a batch (a) at a specified batch update time such as 1 AM or (b) when the HCP system contacts the DMA system and requests that stored algorithms be sent.

For example, the DMA system may send the algorithms relating to patient P when triggered by a notification from an HCP system that the user of the HCP system has selected patient P as the current patient. In another example, the DMA system may send the algorithms relating to patient P when triggered by a notification from an HCP system that patient P has an upcoming appointment with clinic served by the HCP system. In a further example, the DMA system may send the algorithms relating to patient P and task T when triggered by medical information from an HCP system that the user of the HCP system has selected patient P as the current patient and has selected task T. For example, the DMA system may send algorithms relating to a patient's medication formulary when the HCP system begins the task of writing a prescription for the patient.

In a further example, the DMA system may send the algorithms relating to one or more findings criteria F when triggered by medical information from an HCP system that findings stored for a patient match criteria F. For example, when the HCP system sends medical data indicating that the finding "diagnosis=diabetes" has been entered for a patient, the DMA system may send algorithms that display information on how to enroll a patient for a diabetes management program.

In another example, when previously stored findings indicate that a patient is demographically eligible for a particular drug trial and a new finding is received from an HCP system and stored, and this new finding is a diagnosis that matches the selection diagnosis for the medical trial, the DMA system sends an algorithm alerting the HCP that the patient is eligible for enrollment in the specified medication trial.

Selection may occur at the DMA system or at the HCP system. One or both may store the needed information and may perform selection operations. Selection tasks may be partitioned to one or both in various combinations. In one example, all algorithms may be sent to all HCPs and filtered at the HCP. In another example, all data and events may be sent to the DMA and filtering performed at the DMA. In a further embodiment, filtering and selection tasks may be shared between the HCPs and DMAs.

The DMA system can be a PC, server, multiprocessor, distributed collection of machines connected by a network, a server with separate access terminals that communicate with the server with some suitable protocol (e.g., X, HTTP, VNC, tty dumb terminal) or any combination thereof.

In one example, the DMA system may include a CPU and memory. The DMA system may further include an input/display: screen, keyboard, or mouse. The DMA system may further include persistent storage and may include a network interface. The DMA system may also communicate using encrypted communication. For example, the DMA may utilize authentication and privacy features. In one exemplary embodiment, the DMA may only accept messages from the HCP. In another exemplary embodiment, the HCP may only accept messages from the DMA.

Figure 10:
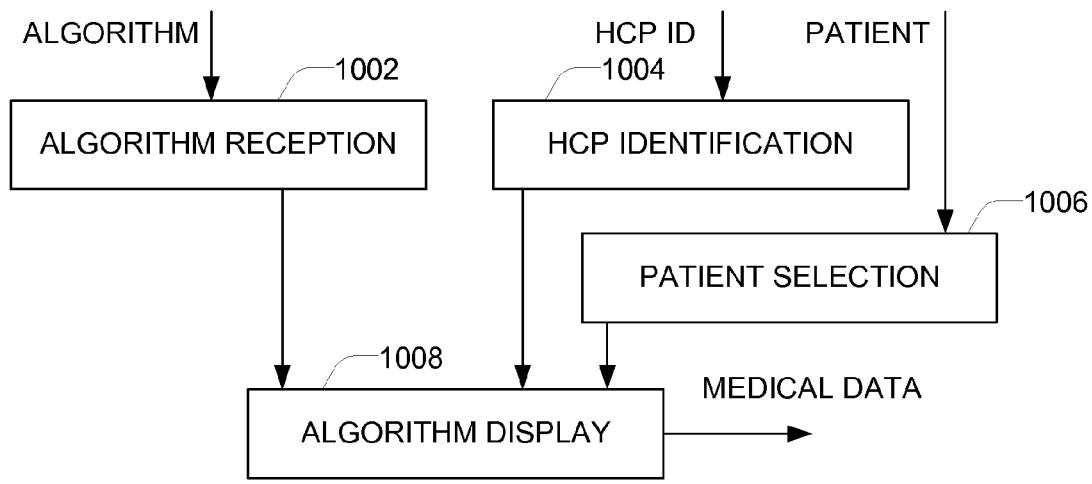
Figure 11:
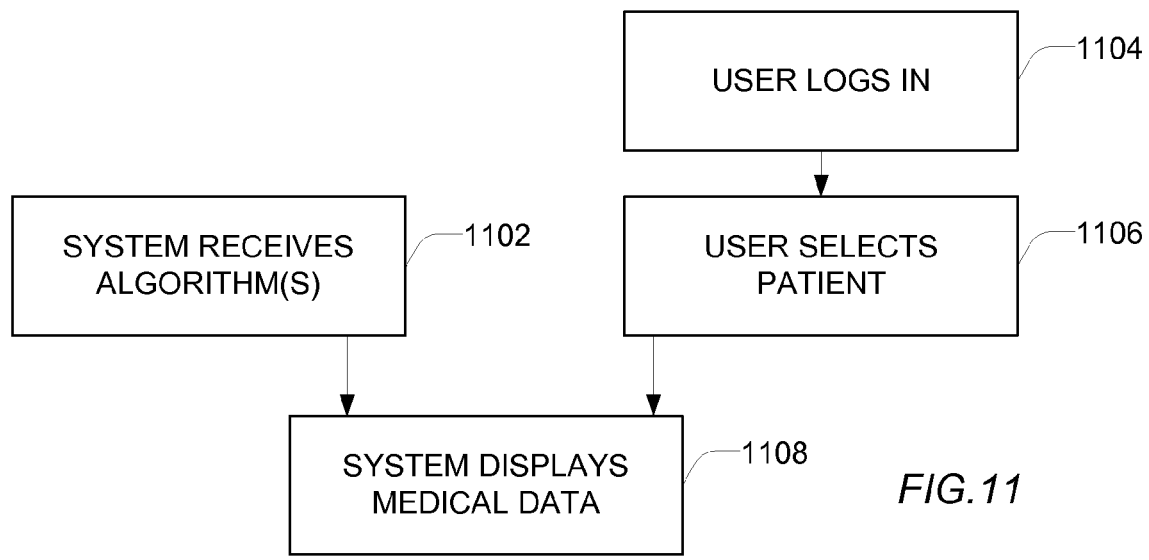

FIG. 10 illustrates components of an exemplary embodiment of the HCP system. The embodiment includes a reception module 1002, an HCP identification module 1004, a patient selection module 1006, and an algorithm display module 1008. In this embodiment and as illustrated in FIG. 11, the HCP system receives one or more algorithms from the network, as shown at step 1102. A user logs in (thereby specifying to the system the HCP ID of the user), as shown at step 1104. The user specifies a patient to examine or treat, as shown at step 1106. The algorithm display module 1004 displays medical data from one or more algorithms, as shown at step 1108.

Figure 12:
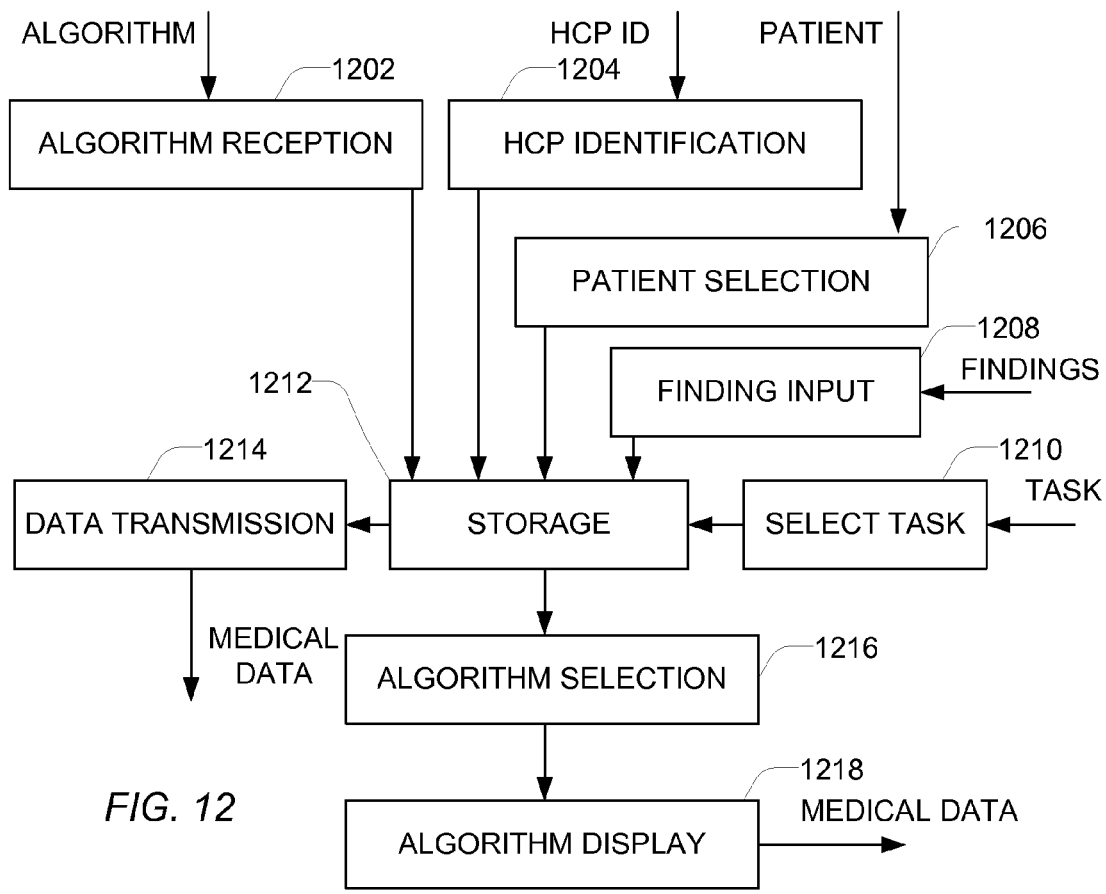

FIG. 12 illustrates components of an exemplary embodiment of the HCP system. The exemplary embodiment may include an algorithm reception module 1202, an HCP identification module 1204, a patient selection module 1206, a finding input module 1208, a task selection module 1210, storage 1212, an algorithm selection module 1216, and an algorithm display module 1218. This embodiment also includes a medical data transmission module 1214.

In this embodiment, the system may receive and store one or more algorithms. A user may be identified, may select a patient, may select a task, and may enter zero or more findings about the patient. The algorithm selection system 1216 may select one or more algorithms to display by matching algorithm conditions against the HCP ID, patient ID, current task, or findings about the patient. Note that the findings may have been entered during the current session or retrieved from storage from data entered into or loaded into the system at a previous time. The algorithm display module 1218 may display medical data associated with the selected algorithm(s) to the user.

In this embodiment, the selection and display functions may be triggered each time a different user logs in, each time a user selects a different patient, each time a user activates a task, and each time a user adds or updates a finding. In another embodiment, the selection and display functions may be triggered by a subset of these events. In this embodiment, stored medical data such as the current logged-in HCP, the current patient, findings, or the current task may also be transmitted to one or more DMA systems. In another embodiment, a user other than the user treating the patient selects the patient. For example, a receptionist may select a patient for the HCP to treat.

The HCP identification module 1204 may allow a user to signify the identity of the user currently using the HCP system. In a particular embodiment, the HCP identification module 1204 is a log-in module in which the user enters a user ID and password. The system may verify that the entered password matches the stored password for the specified user ID, and, if so, may store the fact that the specified user is the current user of the HCP system. In another embodiment, the HCP identification module 1204 may associate an HCP system with a specific user.

The patient selection module 1206 may select a patient that an HCP is to treat or examine while using the HCP system. In a particular embodiment, the current user of the HCP system may select a patient from a list of patients stored in and displayed by the HCP system. At least two views of this list may be supported. First, the user may view and select from all patients that are customers of the HCP's clinic, department, practice, or hospital. Second, the user may view and select from those patients that have checked in with the receptionist. In another embodiment, a user other than the current user may select a patient for the current user to treat or examine. For example, a nurse or receptionist may select the next patient that a doctor should treat.

In another embodiment, the current patient on an HCP device may be selected based on the room in which that HCP device is located. In this embodiment, a receptionist may enter the patient ID of the patient in a specific room and may indicate the room in which that patient is located. If the HCP system is a portable device, when the HCP carries his or her HCP system into the room, the HCP system may determine the room it is in using a location method such as Cricket, a bar code reader, or an IR Transponder. The patient in that room may become the selected patient for the HCP system. If the HCP system is a non-portable device with different HCP systems in different rooms, the assignment of a patient to a room automatically may make the specified patient the selected patient for the HCP system.

In a further embodiment, the current patient on an HCP device may be selected based on patient input. In this embodiment, a patient may log into the HCP device using a smart card and may become the current patient of the HCP device. Optionally, the patient may enter medical information into the device. Then, an HCP may become the current user of the device and the patient may remain the device's current patient.

The finding input module 1208 receives and stores findings about patients. In a particular embodiment, the finding input module 1208 may be an electronic medical record (EMR) system, which may provide a graphical user interface (GUI) for the display and entry of medical information. An example of such an EMR system is the Medcin ChartBuilder™ GUI. In another embodiment, the finding input module 1208 may be an interface for receiving information from a data storage system or computer program that contains findings about a patient.

An HCP may engage in various tasks during the treatment or examination of a patient. Tasks may include activities, such as: log in, select patient, refill prescription, read correspondence, history of present illness, physical exam, review/update patient medical social and family history, diagnose, select billing code, order tests, order treatments, order laboratory tests, select medications, review literature, recommend consultation, review past charts, annotate past charts, and council patient. Within these tasks, there may be subtasks. For example, within select medication, a user may engage in activities, such as select a category of medication, select a specific medication, review warnings about a selected medication, review drug monographs, select a dosage, select a route, or confirm selected medication.

As a user performs tasks and subtasks, the task select module 1210 may store in the HCP system a state indicating the current activity of the user. In one embodiment, the task select module 1210 may detect when a user selects the read notifications task. In this embodiment, algorithms relating to a patient may be displayed during a designated step in the treatment of that patient. In one embodiment, the task select module 1210 may detect each navigation action of a user that is accessing an electronic medical record (EMR) system. In this embodiment, subsets of algorithms relating to a patient may be displayed as separate tasks under the EMR system and are selected by the HCP. For example, a message describing the appropriate step therapy of antibiotics for ear infections may be displayed in a banner when the HCP selects the prescription-writing task while treating a current patient for whom the HCP has entered a diagnostic finding of ear infection. For example, an audible alert may be sounded and a banner add describing the appropriate step therapy of antibiotics for ear infections may be displayed when the HCP selects an expensive, high-potency antibiotic during the prescription-writing task while treating a current patient for which the HCP has entered a diagnostic finding of ear infection and for which there is no stored finding of recent use of first-line antibiotics.

The algorithm selection module 1216 may select one or more algorithms to display based on one or more factors such as the identity of the current patient, the identity of the current HCP user, the facility with which the HCP system is associated, findings about the current patient, or the current task. It is of note that the algorithm selection module 1216 may select algorithms relating to the current patient in at least two ways. First, the algorithm may be selected by selecting algorithms based on the patient identity. For example, an algorithm may include "MATCH PATIENT_ID John Doe" as a selection condition. Second, the algorithm may be selected by selecting algorithms based on findings, which are by definition medical data about a particular patient. For example, an algorithm may include "MATCH SMOKING_STATUS Yes" as a selection condition.

In one embodiment, the algorithm selection module may specify selection criteria in terms of the controlled medical vocabulary used by the HCP system to store patient information. In this embodiment, a conversion module may convert an algorithm specified by a DMA using a different controlled medical vocabulary into the HCP controlled medical vocabulary.

In a particular embodiment, the algorithm selection module 1216 may iterate across all stored algorithms. For each stored algorithm, the algorithm selection module 1216 may execute a function that takes as input (a) an algorithm's selection condition that specifies a Boolean equation based on the HCP ID, patient ID, finding values, and task and (b) the current stored values of the HCP system's current HCP user, current patient, findings about the current patient, or current task. The algorithm selection module 1216 may instantiate the current stored values into the selection condition's equation and may evaluate that equation. This function may return the Boolean value TRUE if the stored values satisfy the selection condition and FALSE otherwise. After executing the function for each stored algorithm, the selection module 1216 may return the set of algorithms for which the function returns TRUE.

In another preferred embodiment, the algorithm selection module 1216 may iterate across all stored algorithms. For each stored algorithm, the algorithm selection module 1216 may execute a function that takes as input (a) an algorithm's selection condition that specifies a computer function that returns a numeric value and that takes as argument the HCP ID, patient ID, finding values, and task and (b) the current stored values of the HCP system's current HCP user, current patient, findings about the current patient, and current task. The algorithm selection module 1216 may execute the selection condition's function using the current stored values as input. This function may return, for example, a numeric value: 0 when the algorithm is irrelevant to the current patient or a positive value when the algorithm is relevant. Higher positive values may be regarded as indicating higher importance or relevance. After executing the function for each stored algorithm, the selection module 1216 may return the algorithm for which the function returns the higher numerical value.

Other algorithm selection module embodiments are possible. For example, the efficiency of execution may be improved by storing algorithms in a tree data structure based on the current task and finding values that satisfy each algorithm's selection condition and then traversing the tree based on the current stored values.

In one embodiment, the system may enforce access control on algorithms, restricting which patient information they can access, which findings they can read, which findings they can write, which entities they can transmit information to, and which information can be transmitted. In one embodiment, the system may enforce that algorithms issued by a particular DMA D match for patients that DMA is authorized to access. In this embodiment, each patient may be associated with one or more DMAs (e.g., the patient's insurance company, HMO, and pharmacy benefits management company.) The system may require an algorithm issued by DMA D to include the condition "MATCH PATIENT_DMA INCLUDES D". Such an arrangement may allow the system to enforce security and privacy rules by preventing unauthorized access to patient medical data.

The algorithm display module 1218 may display medical data associated with an algorithm to the HCP user. Examples of display methods may include visual interface, such as displaying a text message, displaying a list of titles of one or more text messages, displaying an icon, displaying a graphical or textual banner, displaying a dialog box, highlighting an item on the screen, changing the order of one or more items on a template for input or output of medical data displayed on a screen, adding one or more items to a template for input or output of medical data displayed on a screen, displaying information, displaying a dialog, displaying a template for input, displaying an approval template, preselecting a displayed element, or displaying an animation. Examples of display methods may include audio methods, such as sounding a beep, sounding a series of sounds, or outputting spoken words. Examples of display methods may include tactile methods, such as vibrating the HCP device or vibrating an input/output device. Examples of display methods may include multi-device methods, such as issuing a telephone call to an HCP portable or non-portable phone, issuing a page to an HCP pager, issuing a telephone call to a clinic, issuing a fax transmission to an HCP or clinic, or sending an email to an HCP or clinic. In one embodiment, a transmission module is associated with the display methods where the transmission module sends some medical finding information to at least one DMA.

In one embodiment, the system may display algorithms using a GUI interface that resembles web-based email. In this embodiment, when an HCP user works with a patient, an icon may be displayed when algorithms have been selected as relevant for that patient. When an HCP user enters the view messages task, a list of message titles from the medical data of each selected algorithm may be displayed. When an HCP user selects one of the messages and enters the view that message task, the body of the message from the medical data of that algorithm may be displayed. In one embodiment, that body may be a simple textual message. In another embodiment, that body may be an HTML or XML form that can be filled out by the doctor and transmitted to the DMA that originated the message.

In one embodiment, the system may display medical data by issuing a tactile alert, such as by vibrating the HCP device. For example, in this embodiment, a selection condition may evaluate to true when the patient is enrolled with pharmacy benefits company B, the current task is select medication, and the current medication selected does not appear on company B's formulary list. When this selection condition evaluates to true, the medical data associated with the algorithm may be a directive to issue a tactile alert by vibrating the HCP device.

In another embodiment, the system displays medical data visually by displaying a banner containing the medical information in pictorial form (e.g., GIF or JPEG), animation form (e.g., FLASH or MPEG), or text form (e.g., text, XML, or HTML) in an area on the screen of the HCP device. In this embodiment, when a selection condition evaluates to true, the medical data associated with the algorithm may be a directive to display a banner and a reference to a storage location containing that banner. This reference to a storage location containing the banner may refer to local system DRAM memory (e.g., using a memory address), local system disk (e.g., using a file name or database query), or remote system storage (e.g., using a URL or URN). When the selection condition for such an algorithm is triggered, the algorithm display module may display the specified banner on the HCP device screen.

Figure 14:
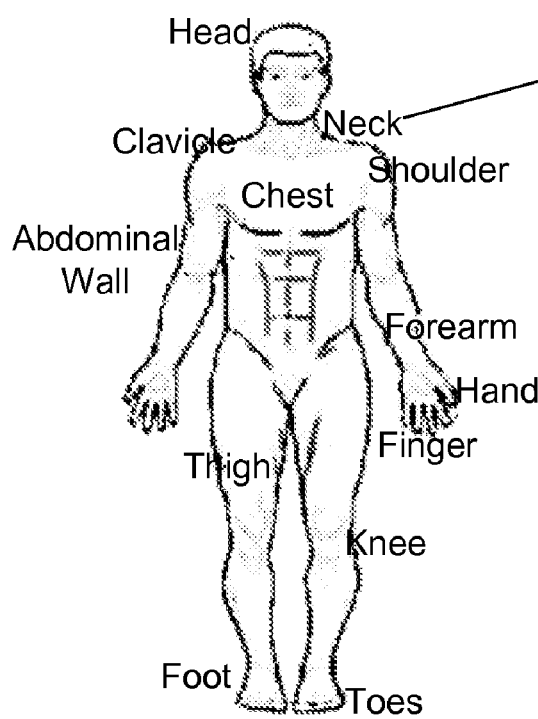

In a further embodiment, the system may display medical data visually by altering a template. A template is a medical interface structure for displaying or gathering medical information. For example, FIGS. 13 and 14 illustrate EMR templates for entering and viewing findings. In this embodiment, the medical data to be displayed may include a template ID, a list of new template elements to add, a list of existing elements on that template to delete, and a list of the order in which template elements should be displayed. Rather than display the original default template, the system may modify the default template by applying the transformations described in the medical data to display an altered template. FIG. 13 illustrates the display of an altered template with one question added by the algorithm display module.

In one embodiment, the system may provide several display modules including web-based email message display, tactile alert, banner display, or modify template. In this embodiment, the medical data associated with each algorithm may include a DISPLAY_TYPE field and a DISPLAY_CONTENT field. The system may display the content stored in the DISPLAY_CONTENT field using a method specified by the DISPLAY_TYPE field.

The medical data transmission module 1214 of FIG. 12 may transmit stored medical data to a DMA system. In one embodiment, stored medical data may be sent independent of the algorithms issued by the DMA system. For example, the HCP system regularly may send all findings information stored about DMA D's patients to DMA D's DMA system. In another example, the HCP system regularly may send anonomized information about all patients to a research university. In a further example, the HCP system may send updates about medication and allergy information about patients registered with a particular pharmacy benefits management company C to C's DMA system whenever an update is made to that information.

In one embodiment, algorithms may include directives to send specific information to specific DMA systems. For example, when an algorithm is selected by a selection module, the medical data for the algorithm may direct the system to transmit specific information to a specific DMA. For example, an algorithm selected when a particular test is ordered for patients of a particular DMA may send findings that indicate whether that test is to be reimbursed to the DMA. In one embodiment, this information may be sent automatically without intervention by the HCP user. In another embodiment, this information may be sent after being displayed to and updated by the HCP user.

Figure 15:

In one embodiment, the HCP system may implement an interface similar to that of web-based email. In this embodiment, DMA systems may send algorithms to HCP systems. These algorithms may specify as conditions for display at least one patient ID or finding condition. The HCP user may log into the system. Then, the HCP user repeatedly may select a current patient and may examine and treat the current patient. While treating the current patient, the HCP may select the Display messages task. When the HCP selects this task, the HCP system may select from the set of stored algorithms those algorithms that either include the current patient ID as their selection condition or that include a set of one or more finding conditions that match findings stored for the current patient. These selected algorithms may be displayed as a list, where each item on the list may include a priority, title, and identity of the issuing DMA, which may be stored as fields of the medical data associated with the algorithm. FIG. 15 illustrates such a display. The HCP may select one or more messages for more detailed display. Each time a message is selected for more detailed display, the body of the message may be displayed. In one embodiment, the body may contain text. The HCP may have the option to activate a reply button, compose a textual reply, and transmit that textual reply to the DMA specified by the algorithm.

In another embodiment, the message body may contain an XML template. For example, the template may provide a list of questions that may be answered by inputting medical findings. The answers to these questions may be initialized to the findings present for the current patient or left initialized to unanswered if no matching finding has been entered for the current patient. The HCP may update this template by entering findings about the current patient. These findings may be stored to the current patient record. When the HCP has completed updating these findings, the HCP may activate a reply button on the screen, causing the HCP system to transmit the findings on the template to the DMA.

Figure 16:
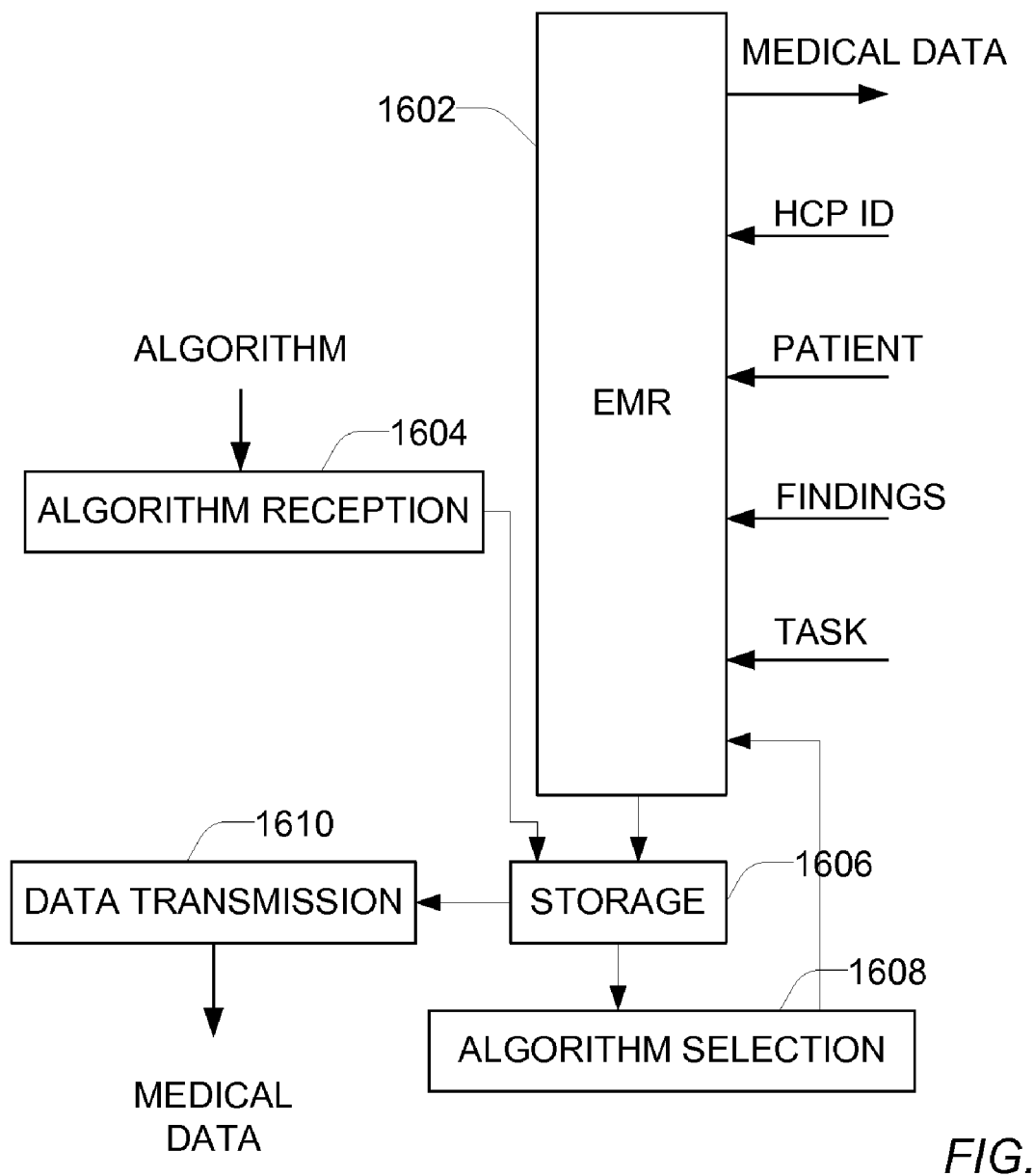
FIG. 16 includes a flow diagram illustrating an exemplary method for use by a disease management system, such as those illustrated in FIGS. 1, 2, and 3.

In one embodiment, the HCP system may be integrated with an electronic medical record system. As illustrated in FIG. 16, the HCP system may include a reception module 1604, a storage module 1606, a data transmission module 1610, and an EMR module 1602.

The HCP system may include a CPU and memory, input and display devices, such as screens, keyboards, mice, etc. permanent storage devices, and a network access. The HCP system may communicate using encryption, authentication and privacy algorithms. In one exemplary embodiment, the DMA system only accepts messages from the HCP system. In another exemplary embodiment, the HCP system only accepts messages from the DMA system.

The EMR module 1602 may include interfaces to log in (identify user), select patient, and select task. The EMR module 1602 further may include several tasks interfaces, such as HPI (history of present illness), ROS (review of systems), Dx (enter diagnosis), or Rx (enter prescription). Each of these task interfaces may be regarded as a template that includes interface elements for inputting medical findings, displaying medical findings, or both. In this embodiment, as each task may be selected, the stored current task state may be updated and provided to the selection module 1608 as input. In this embodiment, each of these tasks may provide a display interface to the HCP system, which allows algorithms to display medical data during execution of a task. Examples of display methods supported by this display interface may include displaying a banner, highlighting a question on a template, adding a question to a template, reordering questions on a template, displaying an icon on a template, or displaying a dialog box.

Figure 17:
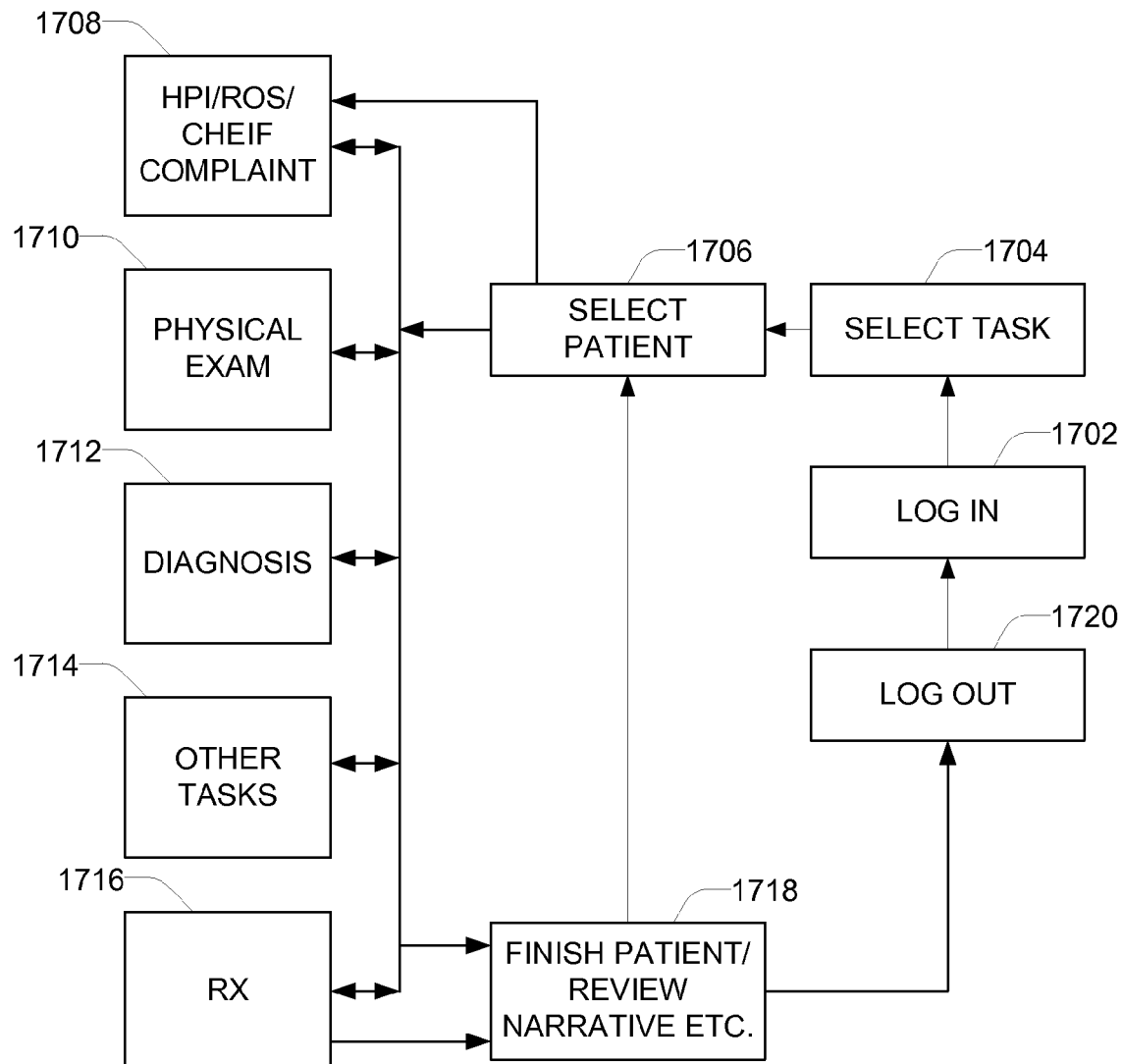
FIG. 17 includes a flow diagram illustrating an exemplary medical workflow.

Generally, a physician follows a pattern of tasks. FIG. 17 illustrates an exemplary procedure. For example, a physician may log-in to a portable device and the healthcare provider system, as shown at step 1702. The physician may select a general task, as shown at step 1704. In one exemplary embodiment, the general task may include visiting a patient. The physician may select a patient, as shown at step 1706. The physician may select a specific task relating to the patient visit. Generally, the physician follows an ordered procedure. However, the physician may skip steps or jump to previous steps. In one particular embodiment, some of the steps may be performed prior to the physician's patient visit.

In this exemplary embodiment, the physician performs an HPI, ROS, and chief complaint review, as shown at step 1708. The physician may perform a physical exam, diagnosis, other tasks, such as order procedures and tests, write a prescription, or review a note or narrative, as shown in steps 1710, 1712, 1714, 1716 and 1718, respectively. The physician may then log-out, as shown at step 1720.

Each of these tasks may be documented using an interface that includes control elements for indicating findings associated with the step in the procedure. The findings may be recorded in an electronic medical records system based on a controlled medical vocabulary. In addition, the electronic medical record (EMR) system may configure the interface based on disease management algorithms. For example, when the selection conditions of the disease management algorithm match conditions found in the EMR system, the interface may be adjusted based on the disease management algorithm's coding. For example, selection of a patient may activate a message associated with that patient. In another example, selection of a test or procedure order may activate a payer rule that indicates an interest in more data before the order is approved. In a further exemplary embodiment, the selection of a prescription given a set of findings may result in the display of a warning message or the encouragement to prescribe an alternative medication.

Figure 18:
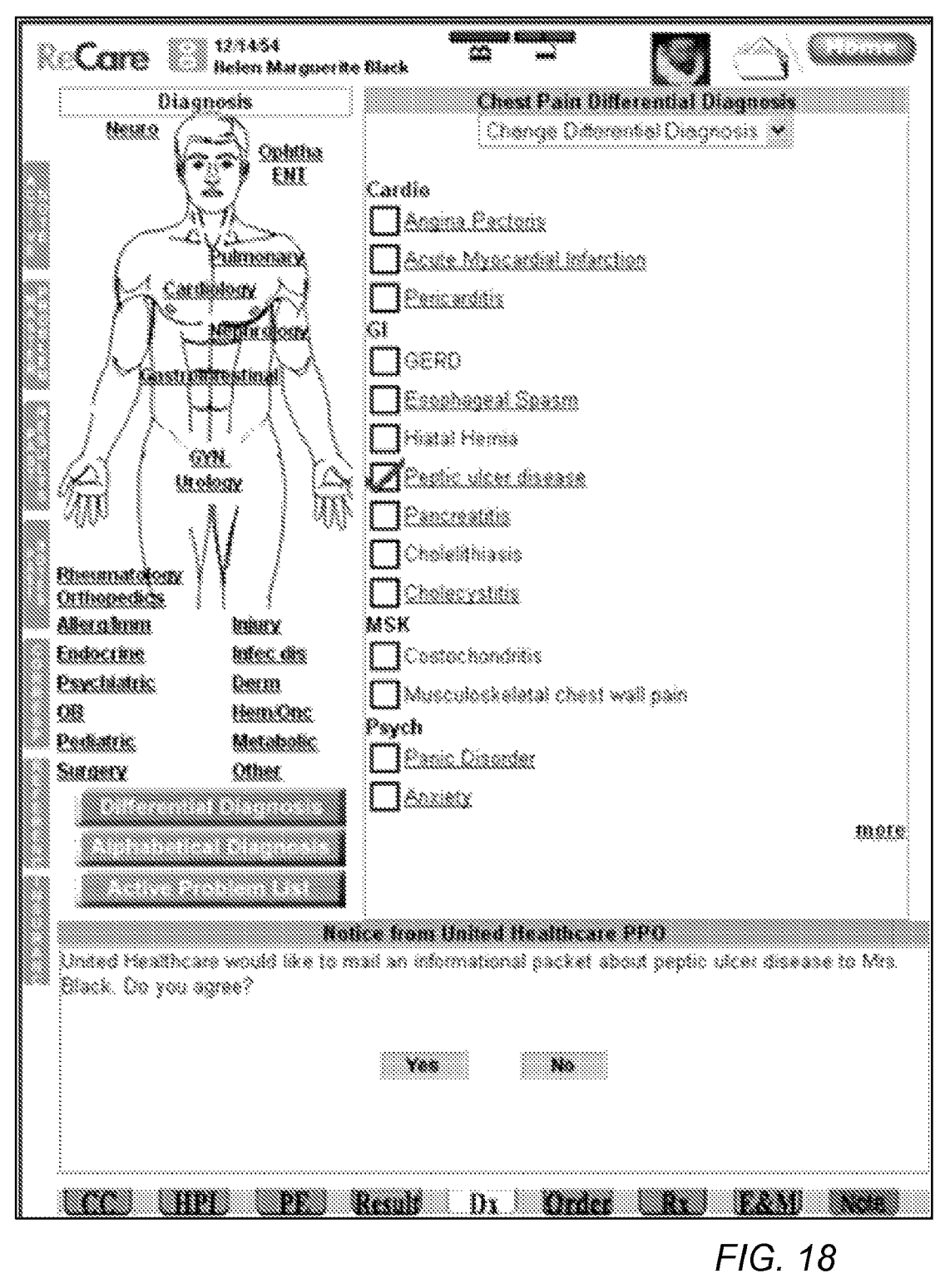
Figure 19:
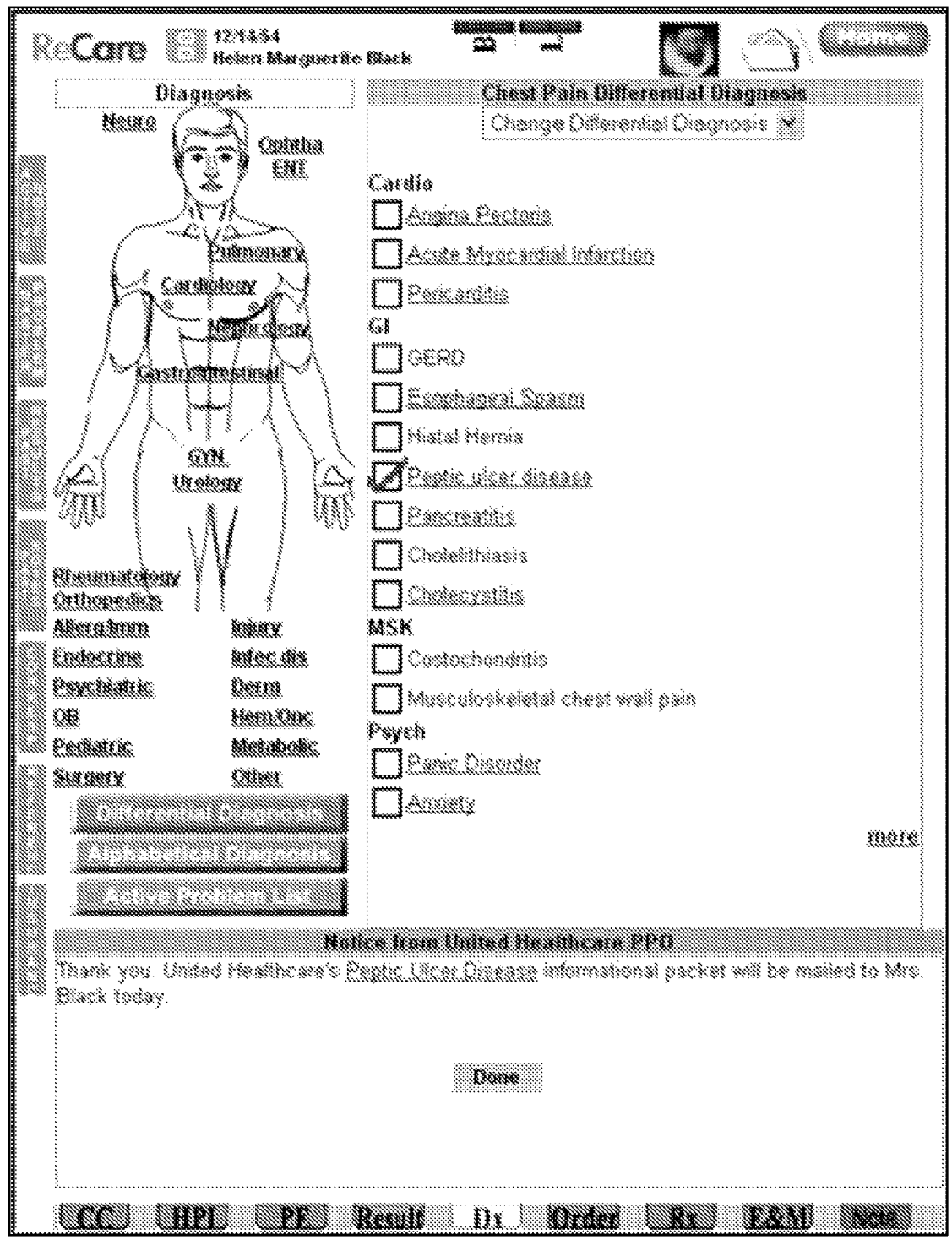
Figure 20:
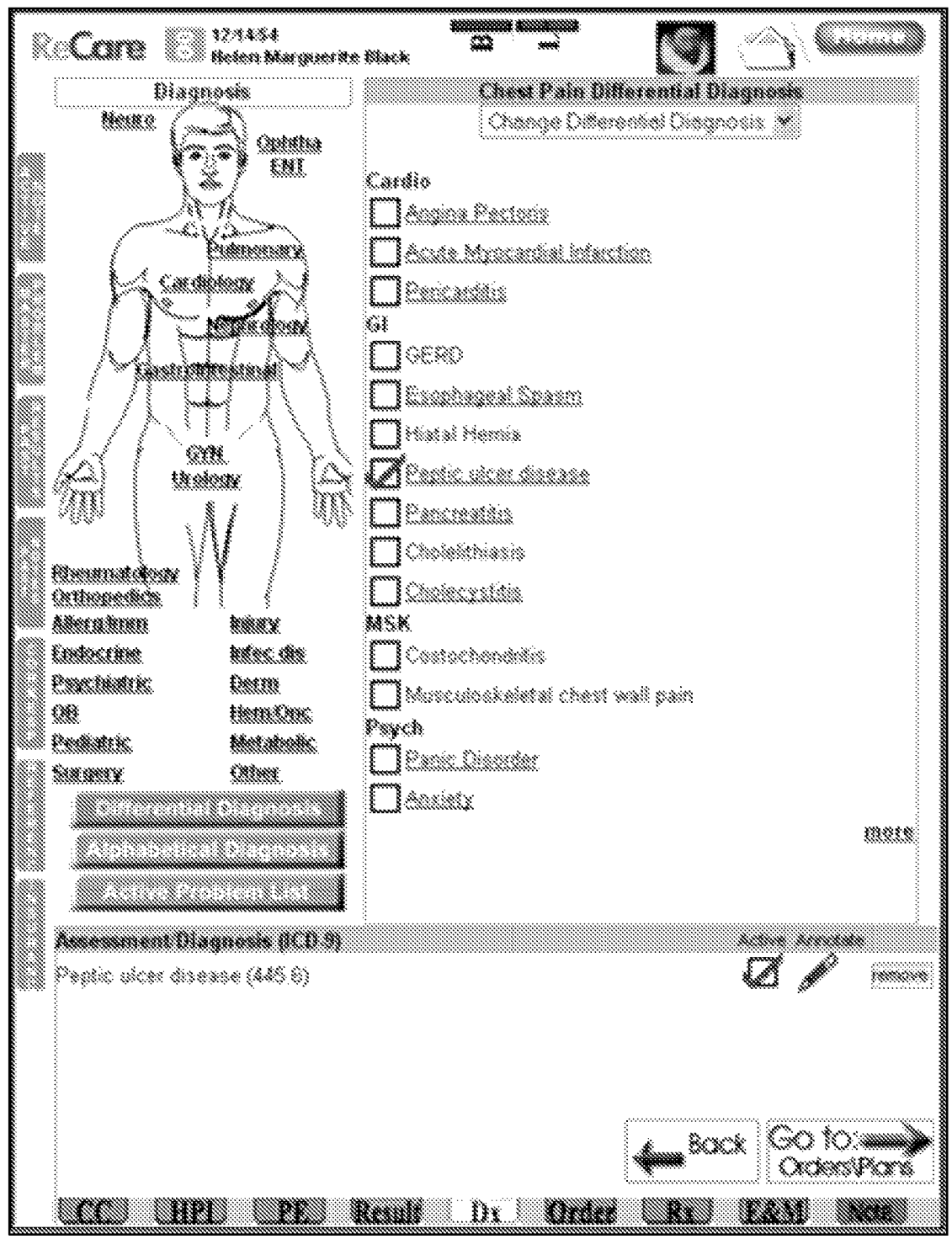

For example, FIG. 18 illustrates an example in which selection of a finding in an EMR system results in a message asking the physician to provide permission to send the patient information about their condition. The physician may, for example, ask the patient whether the patient would like information to be sent and indicate the patient's response using the control elements provided. When, for example, the physician indicates yes, the system may display another message, such as a thank you message or indication that the response was received, as illustrated in FIG. 19. As illustrated in FIG. 20, the physician may be permitted to continue with the patient visit.

Figure 21:
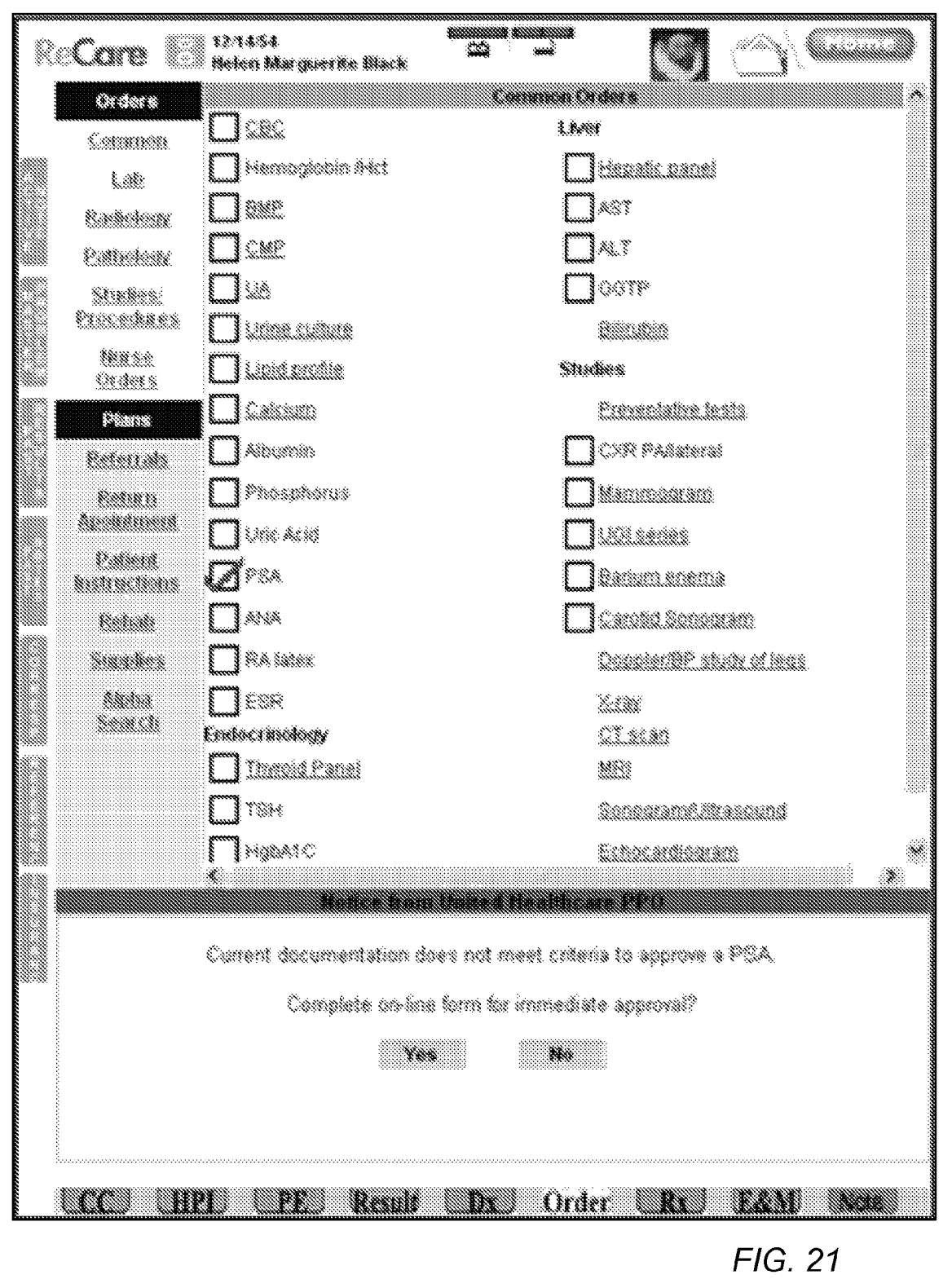
Figure 22:
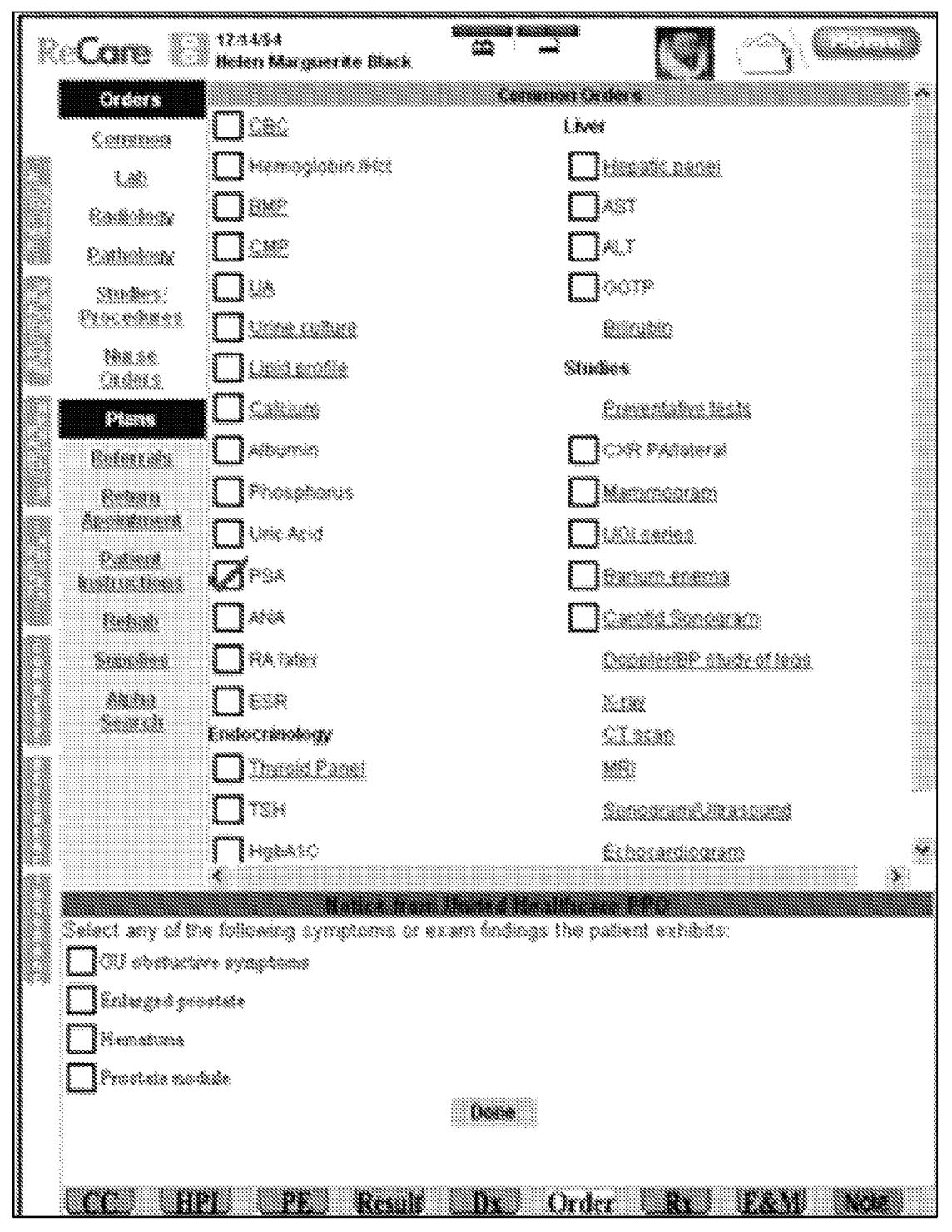
Figure 23:
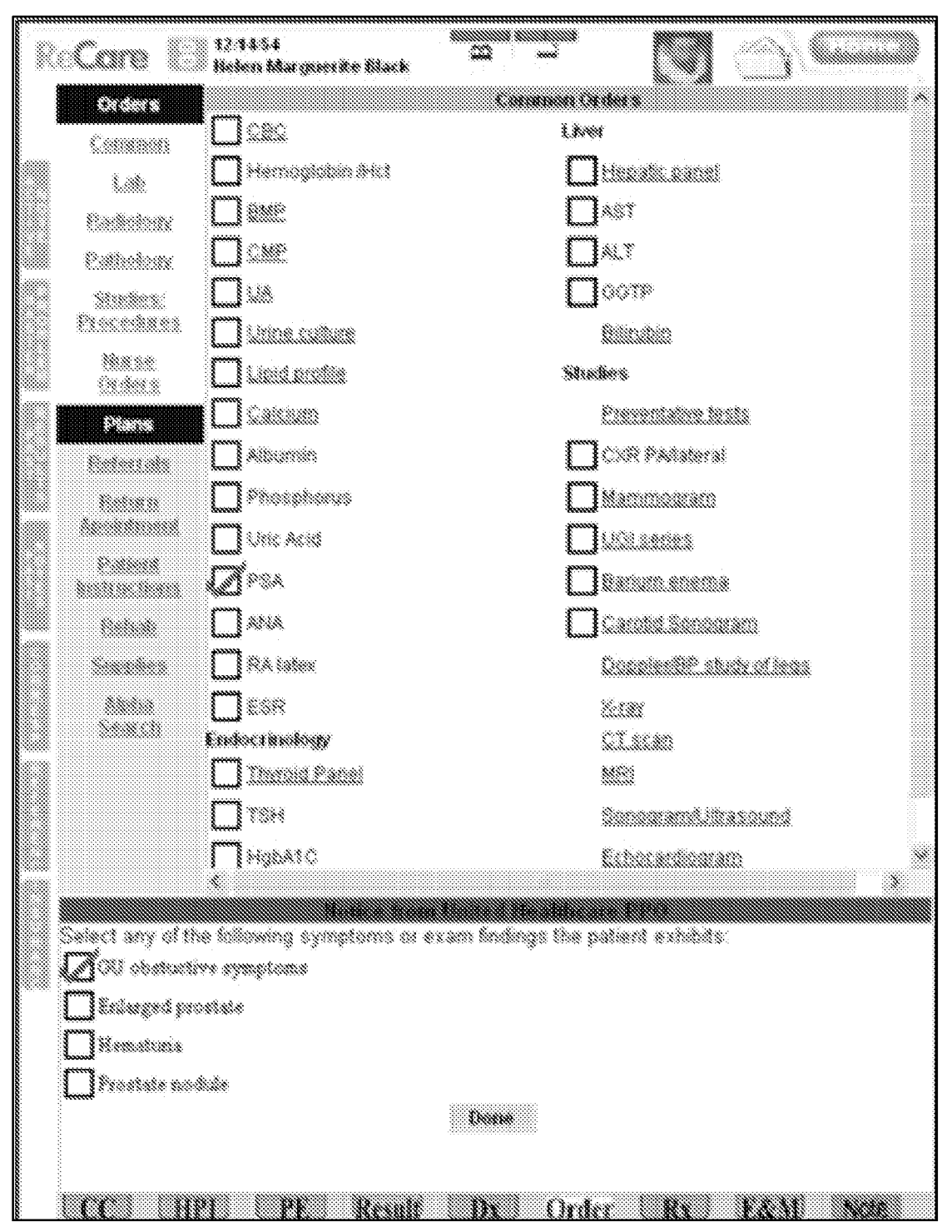
Figure 24:
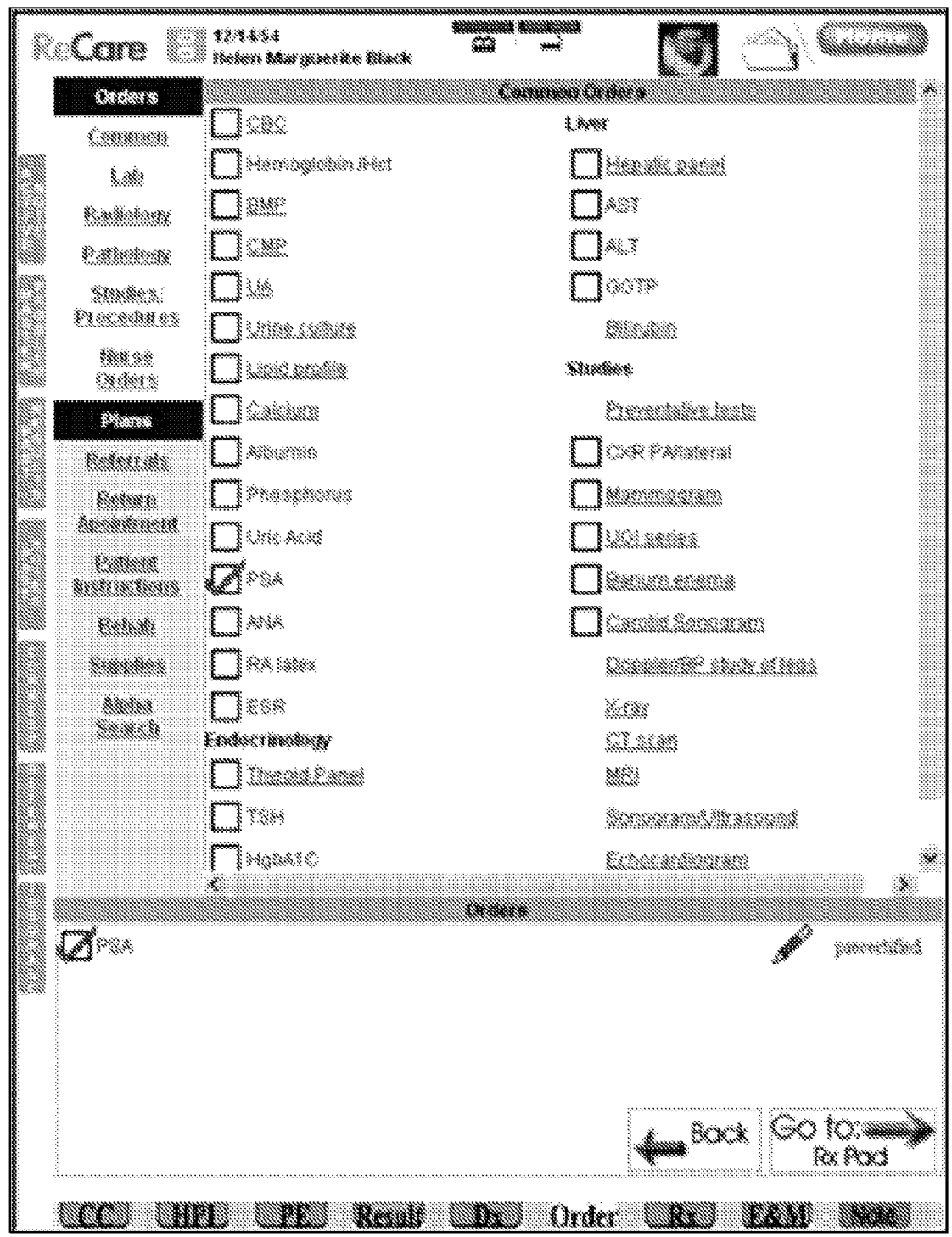

In another exemplary embodiment, when a physician is ordering a test or procedure, an algorithm within the system may indicate that the current documentation does not support ordering the test, as illustrated in FIG. 21. The physician may be prompted to enter more information and may be provided with a shortened template for providing the additional information, as illustrated in FIG. 22. The physician may provide additional documentation, as shown in FIG. 23, and proceed in ordering the test, as shown in FIG. 24.

The DMA associated with this procedure may indicate the rule associating the set of findings or lack thereof with the ordered test. This rule may be converted based on the EMR's controlled medical vocabulary and presented in an interface that is specific to the EMR. Other EMR systems may interpret the disease management algorithm based on their specific controlled medical vocabulary and present the results of the rule in their specific interface format. In this manner, a single disease management algorithm may be implemented in multiple types or brands of EMR systems.

Figure 26:
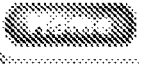
Figure 27:
Figure 28:
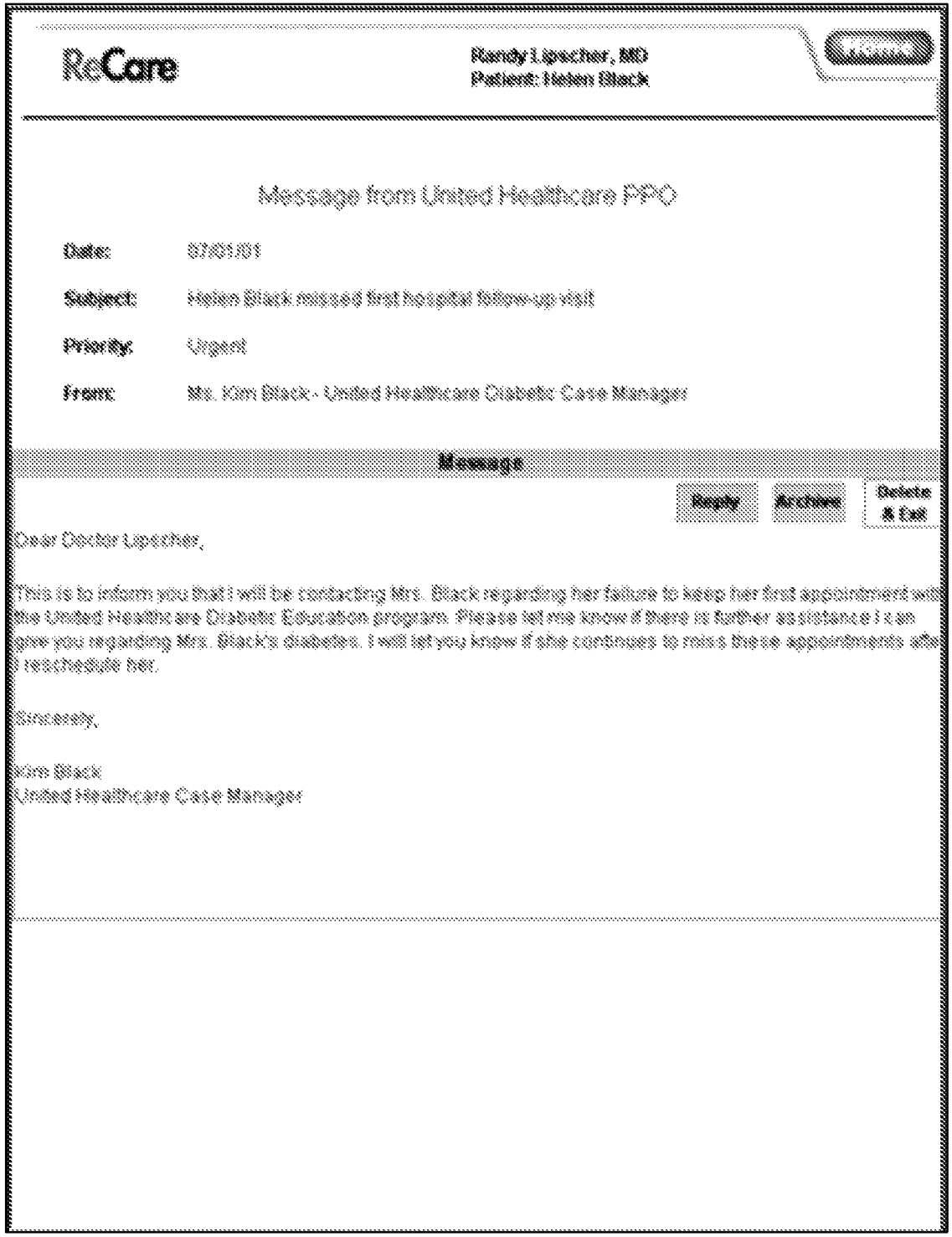

In another exemplary embodiment, a disease management algorithm may be triggered by the selection of a patient. For example, selection of a patient Helen Black, from a list illustrated in FIG. 25 may result in the display of medical data associated with the specific patient and optionally the sending of that data to a DMA advisor, as illustrated in FIG. 26, and may result in access to a set of messages associated with the patient, as illustrated in FIG. 27. The physician may selectively review messages, as illustrated in FIG. 28, and may provide a requested response or reply, as illustrated in FIG. 29.

The DMA system also may provide an interface to the DMA advisor for reviewing the response, sending messages to the physician, and providing data to the physician. In one exemplary embodiment, these messages are encoded in an XML file that includes the addressed HCP system, HCP ID, and patient ID as selection criteria and a message and associated data requests as action items. The XML file may be converted based on the controlled medical vocabulary of the receiving HCP system and implemented in a compatible interface, as illustrated in FIGS. 28 and 29.

In one embodiment, the algorithm identifies patients eligible for a clinical trial. For example, the algorithm includes selection criteria for determining eligibility for a clinical trial. In this embodiment, the algorithm also includes medical data that provides the HCP details about the medical trial, a display module comprising an on-line form for enrolling the patient in the trial, and a data transmission module for transmitting information about enrolled patients to an external DMA, such as the entity conducting the clinical trial.

In another embodiment, the algorithm encourages an HCP user to use approved step therapy where inexpensive treatments of tests are attempted first and more expensive treatments or tests attempted when the inexpensive medications are unsuccessful. For example, the algorithm may include selection criteria for patients of a particular payer DMA, for findings consistent with a particular medical condition, for findings indicating that a less expensive treatment or test has not been recently tried, and for the current task being select a treatment or test. In this example, the algorithm also may include medical data formed as a banner alert detailing the recommended step therapy for a medical condition.

In a further embodiment, the algorithm may assist an HCP user in following best practices guidelines for diagnosing or treating a condition. For example, the algorithm may include selection criteria for patients with findings that match specified criteria and for a particular task in an EMR system. In this example, the algorithm also comprises medical data formed as a question added to an EMR template.

In one embodiment, the algorithm may assist an HCP in making accurate coding decisions. In this embodiment, the algorithm may include selection criteria for patients with findings that match specified criteria and for the coding task in a system. In this example, the algorithm also may include medical data formed as a recommended code to be displayed. In another embodiment, the algorithm also may include medical data formed as a set of questions that should be asked to improve coding decisions.

In one embodiment, the algorithm may assist a DMA in teaching HCP to make better diagnostic, treatment selection, or coding decisions. In this embodiment, the algorithm may include selection criteria for patients associated with a particular DMA and for the finish patient task. In this embodiment, the algorithm also may include a directive to transmit findings from the patient encounter to the DMA system. By using this embodiment, the DMA may track the types of diagnostic, treatment selection, or coding decisions made in different circumstances by a particular HCP and identify cases where best practices data or statistics from other HCPs indicate alternative choices could be considered.

In a further embodiment, the algorithm assists a DMA in teaching HCP to make better diagnostic, treatment selection, or coding decisions. The algorithm includes selection criteria for patients findings that match selection criteria and for the task to view messages. In this embodiment, the algorithm also may include medical data, such as a recommendation to consider a particular diagnostic decision, treatment selection decision, or coding decision. For example, the medical data can also include a list of findings questions that should be asked to improve medical decisions. For example, the medical data also may include references (such as HTML URL links) to articles describing a best practice approach.

In one embodiment, the algorithm may provide reference material related to the current patient to an HCP. The algorithm may include selection criteria for patients with findings that match selection criteria and the task to view reference material. In this embodiment, the algorithm also may include medical data, such as links to articles related to certain findings, such as certain diagnoses, disease processes, systems, medications, or allergies.

In a further embodiment, the algorithm may assist DMAs and HCPs in enrolling patients in disease management programs. In this embodiment, the algorithm may include selection criteria for patients belonging to a certain DMA, with findings matching selection criteria, and with findings indicating that they are not currently enrolled in a DMA's disease management program. In this embodiment, the algorithm also may include medical data that assists the HCP in enrolling the patient in the program. For example, in one embodiment, the medical data may include a dialog box to be displayed. This dialog box may display text recommending that the patient be enrolled in the program and may allow an HCP to select "Yes" or "No." After the HCP makes a selection, the finding state may be updated to indicate this data and the patient ID, findings, and this decision may be transmitted to the DMA.

In another embodiment, the algorithm may assist DMAs in educating HCPs about particular products. The algorithm may include selection criteria for a task of selecting a product (e.g., selecting a test or medication) and for patients about whom findings match selection criteria. In another embodiment, the algorithm may include selection criteria for a task of selecting a product (e.g., selecting a test or medication) and the subtask of selecting a particular product (e.g., a particular medication). In either case, the embodiment also may include medical data about a particular medical product. For example, for a medication product, the medical data may include reference material detailed describing prescribing information (e.g., a drug monograph) for the product. For example, for a medication product, the medical data may include a banner display indicating conditions when the product should be considered. In another example, for a medication product, the medical data may include a banner display offering to send a representative to contact the HCP with more information about the medication.

For a preventive care and immunization based embodiment, the DMA, HCP, and patients may use the system to regularly perform and document preventive care procedures according to the practices recommended by the DMA. For example, a DMA (which is referred to as DMA-A) may wish its male patients over the age of 40 to receive a prostate exam once every year. The DMA may specify this as a treatment algorithm with selection criteria selecting patients (a) associated with the DMA, (b) male, (c) over 40 years old, and (d) who have not had a prostate exam during the past year. The DMA system may transmit the treatment algorithm to the healthcare EMR system. Then, when the HCP is accessing the physical exam task, when the current patient meets those criteria, the healthcare EMR system may prompt the user to perform the exam (for example, by displaying a banner graphic indicating that a yearly prostate exam is recommended for the current patient). Finally, when the HCP completes the encounter, the healthcare EMR system may include the results of the prostate exam in the report sent to the DMA.

Preventive care prompting may also be driven by specific data elements entered. For example, some DMAs may wish to remind HCPs to perform a yearly foot exam on diabetes patients and to further prompt the HCP to perform such an exam when working with a diabetic patient who has not had a recent foot exam. The DMAs may specify this rule as algorithm selection criteria with medical data to be displayed to prompt the HCP to perform such an exam, and the HCP system may prompt the physician during the physical exam of such a patient.

In another embodiment, a DMA may modify only a particular template. For example, DMA-A may augment the template for fracture to, for example, encourage calcium supplements for middle-aged or older females. In this embodiment, the selection conditions may include the DMA, the gender and age of a patient, and a diagnostic finding, and the medical data to be displayed may include an additional question to be included on the fracture treatment template.

For an exemplary patient education task embodiment, the DMA, HCP, and patients may use the healthcare EMR system to transmit educational material to patients. In another embodiment, a DMA may develop a set of smoking cessation information that they wish to transmit to their smoking patients. The DMA may prompt the HCP to authorize sending that information when the patient visits the HCP when the HCP is engaged in PMFSH task for the patient and to send that information when the HCP approves.

Similar rules may allow a DMA to communicate diet, exercise, diabetes management, pregnancy, and other information. In one embodiment, a DMA may wish to send educational material to its patients while the patients are using the healthcare EMR system to enter pre-clinical encounter information. For example, in one embodiment, the healthcare EMR system may provide Patient-PMFSH review, Patient-HPI, and patient-INFO tasks that may allow patients to fill in updates to their past medical, family and social history, to enter the history of their present illness and to view selected health information while they wait in the clinic waiting room. For example, when a patient indicates that they have a fever, the DMA may wish to display rules for distinguishing a cold from a fever to the patient while they wait.

Similar arrangements may allow a DMA to provide smoking cessation, diet, exercise, cancer screening, heart disease and similar information to appropriate patients while those patients are in a clinic waiting room or at home filling out pre-clinical information. Such an arrangement also may allow a DMA to inform a patient about general procedures or features of the DMA, such as "Call 1-800-my-nurse for answers to any medical question," or "Go to http://www.DMA-A.com for answers to your health questions" or "Emergency room visits are only reimbursable if DMA-A is notified within 48 hours of the visit" and so on.

For resource utilization based embodiments, the healthcare EMR system may provide methods whereby DMAs can offer guidance to HCPs to improve resource utilization to reduce costs and improve quality of care. For example, the DMA may specify that certain medications, such as those on a formulary list, are preferred to others. This can be accomplished, for example, by highlighting on-formulary medications, highlighting off-formulary medications, or adding a banner of information for medication X that is displayed when medication Y is displayed.

In another example, the DMA may specify a set of questions that the HCP should answer to get approval to prescribe a given off-formulary medication. In one embodiment, this approval process may be accomplished by specifying a question with ID OFF-FORMULARY-DMA-1-MEDICATION-X for approval of medication X by DMA-1 that is displayed when medication X is displayed or when medication X is selected. In another embodiment, when the set of questions is long, this approval process may be accomplished by specifying one initial question that is displayed when medication X is displayed and specifying several additional questions that are asked when the initial question is answered and matches a specific condition. In another embodiment, this set of questions may be specified as a prerequisite question as described above. For example, a similar methodology may be used by a DMA to specify a set of questions that the HCP should answer to get approval to perform a procedure or test.

In another exemplary embodiment, a DMA such as an HMO may use the system to communicate with or guide an HCP who is referring a patient to a different HCP or specialist HCP, such as a surgeon or dermatologist. In one such embodiment, a DMA specifies that when an HCP is working on the SPECIALIST_REFERRAL task and the current patient is associated with the DMA, the system should insert content such as a list of DMA-approved specialists or highlights DMA-approved specialists on the default list. In another such embodiment, a DMA specifies that when an HCP is working on the CARDIAC_SPECIALIST_REFERRAL task and the current patient is associated with the DMA, the system inserts content, such as a list of DMA-approved cardiac specialists or highlights DMA-approved cardiac specialists on the default list. In another exemplary embodiment, a DMA may specify that when an HCP is working on the SPECIALIST_REFERRAL task and the current patient is associated with the DMA and under the condition that the current encounter record includes diagnosis of congestive heart disease, the system inserts content, such as a list of DMA-approved cardiac specialists or highlights DMA-approved cardiac specialists on the default list.

In another exemplary embodiment, a DMA, such as an HMO or benefits management company, may use the system to communicate with or guide an HCP who is ordering a laboratory test or procedure. In one such embodiment, a DMA specifies that when an HCP is working on the ORDER_LABS task and the current patient is associated with the DMA, the system may insert content, such as a list of DMA-approved labs, or highlights DMA-approved labs on the default list. In another such embodiment, a DMA may specify that when an HCP is working on the ORDER_CBC_LABS task and the current patient is associated with the DMA, the system may insert content, such as a list of DMA-approved lab for CBC tests or highlights DMA-approved labs for CBC tests on the default list.

In another exemplary embodiment, a DMA may specify to the system that it desires information gathered by HCPs during an encounter with patients associated with the DMA. In one such embodiment, a DMA may specify that for patients associated with the DMA, the system may insert in the FINISH_ENCOUNTER task content a prompt for the HCP to transmit all findings from the encounter to that DMA. In one embodiment, this content element may include a text message requesting that the HCP transmit the information, a set of hidden elements corresponding to the patient's ID and all findings by the HCP about the patient for the current encounter, and an activation button where activating the button causes the hidden elements to be transmitted to the DMA.

In another exemplary embodiment, a DMA may specify to the system that it wishes to enroll high risk patients, such as diabetics, in specific disease management programs. In one such embodiment, a DMA may specify that for patients associated with the DMA, the system may insert in the FINISH_ENCOUNTER task content including a prompt for the HCP to transmit the patient's name, ID, and diagnosis to that DMA on the condition that the patient is diagnosed with diabetes. In one embodiment, this content element may include a text message requesting that the HCP transmit the information, a set of hidden elements corresponding the patient's ID and diagnosis, and an activation button where activating the button causes the hidden elements to be transmitted to the DMA. In another exemplary embodiment, a DMA, such as a medical research institute, may specify to the system that it wishes to enroll patients meeting criteria specified by the DMA in specific medical studies, such as medication trials. In one such embodiment, a DMA may specify that for all patients, on the condition that the patient's encounter record has fields meeting specified Boolean tests (e.g., age >18 AND gender=F AND smoking=no AND diagnosis=Flu) the system may insert in the FINISH_ENCOUNTER task content including a prompt for the HCP to transmit the patient's name, ID, and diagnosis to that DMA in order to enroll the patient in a study. In one embodiment, this content element may include a text message describing the study and requesting that the HCP transmit the information, a set of hidden elements corresponding the patient's ID, demographic and contact information, and diagnosis, and an activation button where activating the button may cause the hidden elements to be transmitted to the DMA.

In another exemplary embodiment, a DMA, such as an HMO or prescription benefits management company, may use the system to communicate with or guide an HCP who is ordering a medication to encourage the physician to select an appropriate medication based on data-driven medicine, such as step therapy. In one such embodiment, a DMA may specify that when an HCP is working on the prescription task and the current patient is associated with the DMA, and on the condition that the diagnosis matches a specific diagnosis (e.g., diagnosis=ear infection) and that the patient's medical history does not indicate that a first-line antibiotic has been prescribed for the patient (e.g., medications during past 7 days does not include amoxycillin or tetracycline) and that the current encounter record indicates that a powerful or expensive antibiotic has been prescribed (e.g., new medications includes keflex), the system may insert content such as banner display or message reminding the physician that a specified first-line antibiotic is to be generally prescribed before a more powerful or more expensive antibiotic is used (e.g., "For patients with ear infection, the recommended step therapy begins with a 1 week course of amoxycillin or tetracycline. Keflex is to be generally prescribed only if the patient does not respond to these initial medications.")

In further exemplary embodiments, the HCP system may be configured to delete disease management algorithms. For example, a disease management algorithm may have a validity time stamp. The disease management algorithm may be deleted after a period of time or when a similar disease management algorithm having a later time stamp is received. The disease management algorithm may also be configured to direct the deletion of other disease management algorithms. For example, the disease management algorithm may include a specific set of selection criteria or a unique number. An insurance company or a government entity, for example, may periodically update rules and direct that outdated rules be replaced or deleted. In this manner, rules that are to be deleted and replaced may be transmitted instead of a complete set of disease management algorithms associated with that entity.

In an exemplary embodiment, payer information, such as insurance information, may be seamlessly integrated into a physician's workflow. A physician has many tasks to complete during a medical encounter. For example, a physician may document chief complaint, HPI, ROS, physical exam, diagnosis, orders, prescriptions, coding, notes, or any combination thereof. Insurance information includes a large number of factors such as schedule of benefits, covered benefits, exclusions, limitations, or any combination thereof. These factors differ for different patients depending on their payer and payer plan. For example, each insurance provider may have a variety of different insurance plans, including HMO, PPO, or HSA plans, or any combination thereof. Decisions, such as lab orders, radiology orders, tests, procedures, or any combination thereof depend on the interplay between documented findings and insurance information. For example, one payer may routinely approve payment for a particular test when the patient has condition X or condition Y, but a different payer may approve payment for a particular test when the patient has condition X, Y, or Z. By integrating such information in a HCP workflow, the system can use findings gathered during the healthcare provider's documentation of the encounter in order to guide the HCP to using tests that are approved by the patients payer or providing sufficient documentation to justify ordered tests and thereby reduce risk of claim denial, reduce processing effort, improve the quality of care, improve efficiency of the workflow, and reduce administrative processing costs for the payer.

In an embodiment, the system may provide interfaces for selecting a patient, entering findings about the patient (e.g., chief complaint, history of present illness, review of systems, physical exam, or diagnosis), and an interface for selecting one or more orders for a selected patient in an encounter. The system further may store for each patient information identifying payers and plans associated with the patient (e.g., the patient's insurance company and plan or pharmacy benefits management company and plan). The system further may store each payer plan authorization rules for one or more orders. In an exemplary embodiment, the system may store per-patient records that include findings stored in previous encounters, patient status information, and information identifying the patient's payer(s) and plan(s).

In an embodiment, authorization rules may be received via a network from a central server or cluster that, in turn, receives via a network authorization rules from each of a plurality of servers that provide information about the authorization rules of different payers. In another embodiment, authorization rules may be received directly from each payer's server(s). In another embodiment, authorization rules may be received via a network from a central server or cluster that stores rules entered manually based on information from payers. In another embodiment, authorization rules may be received via a network from a central server or cluster that stores rules in a single standard form based on information from payers provided in different, non-standard forms.

In an example, authorization rules may include Boolean rules that operate on medical findings encoded using a controlled medical vocabulary corresponding to the findings stored by electronic medical record. As a result, given a set of findings stored for a patient, the system may compute whether the current set of findings for a patient meets the criteria specified by the patient's payer for the patient's plan for an order.

For example, the system may receive findings documenting the patient's medical condition. The system may display a list of medical orders. In addition, the system may display information about the authorization status of a plurality of medical orders based on the rules specified by the patient's payer for the order and based on findings stored for the patient.

In particular, the present system may integrate orders into a broader electronic health record (EHR) system. In particular, the system may be used for various types of orders, such as labs, radiology, counseling, procedures, MRIs, tests, and so on. In addition, the system may be used for prescriptions for medication and medical equipment. For example, the EHR system may permit documentation of a medical encounter. Furthermore, the EHR system may store medical findings about a patient before an order to be considered in light of a payer's rules is selected. The received or stored medical findings may be automatically considered by the system when evaluating the rules. In addition, the present system further may permit entry of findings after an order has been selected and in the context of the authorization system's highlighting of relevant findings for documenting justification of an order.

In an exemplary embodiment, the system may categorize orders into groups based on findings stored for the patient and the patient's payer's rules for each order. For example, three such groups include: (1) coverage supported by documentation in EHR, (2) pre-certification required, and (3) not covered by patient's policy. In a particular embodiment, orders or prescriptions may be categorized and displayed with a graphic feature that identifies to which category the order or prescription belongs. For example, the graphic feature can be a font, font state, font size, color, icon, or any combination thereof.

Figure 30:
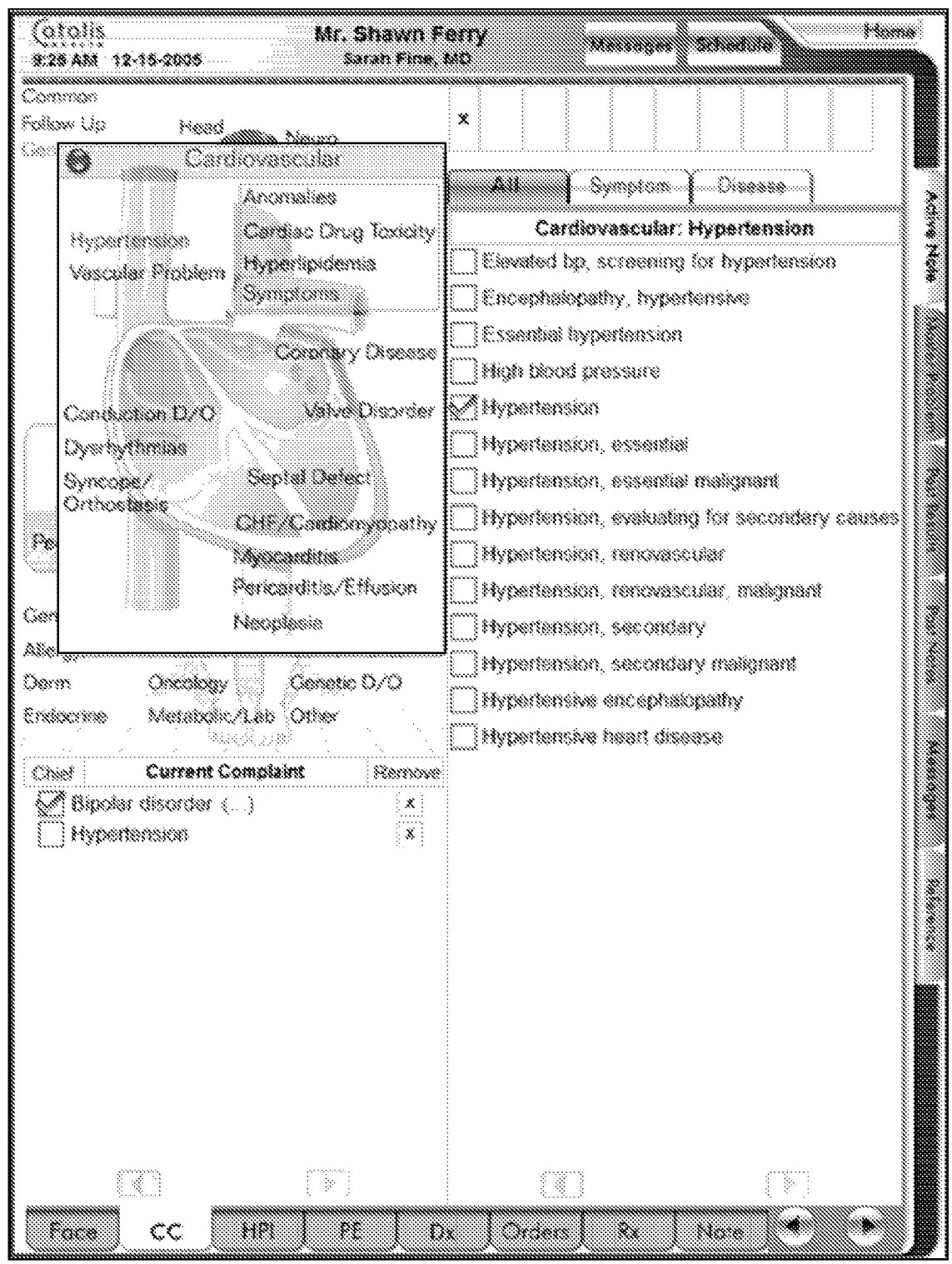

In a particular set of examples illustrated in FIG. 30 through FIG. 54, a healthcare provider performs a series of medical tasks associated with establishing a treatment for the patient. For example, the healthcare provider may logs in, select the patient, and select complaint templates for the patient. In this example, a HCP may selects two complaints: bipolar disorder (which is selected as the chief complaint) and hypertension. As illustrated in FIG. 30, selection of a complaint may be accomplished by navigating to the category of complaint using a graphical representation of the body and systems ("Cardiovascular"), selecting a class of complaint ("Hypertension"), and checking a box next to a specific complaint ("Hypertension"). In addition, in this example, the patient has an active problem of bipolar disorder.

Figure 32:
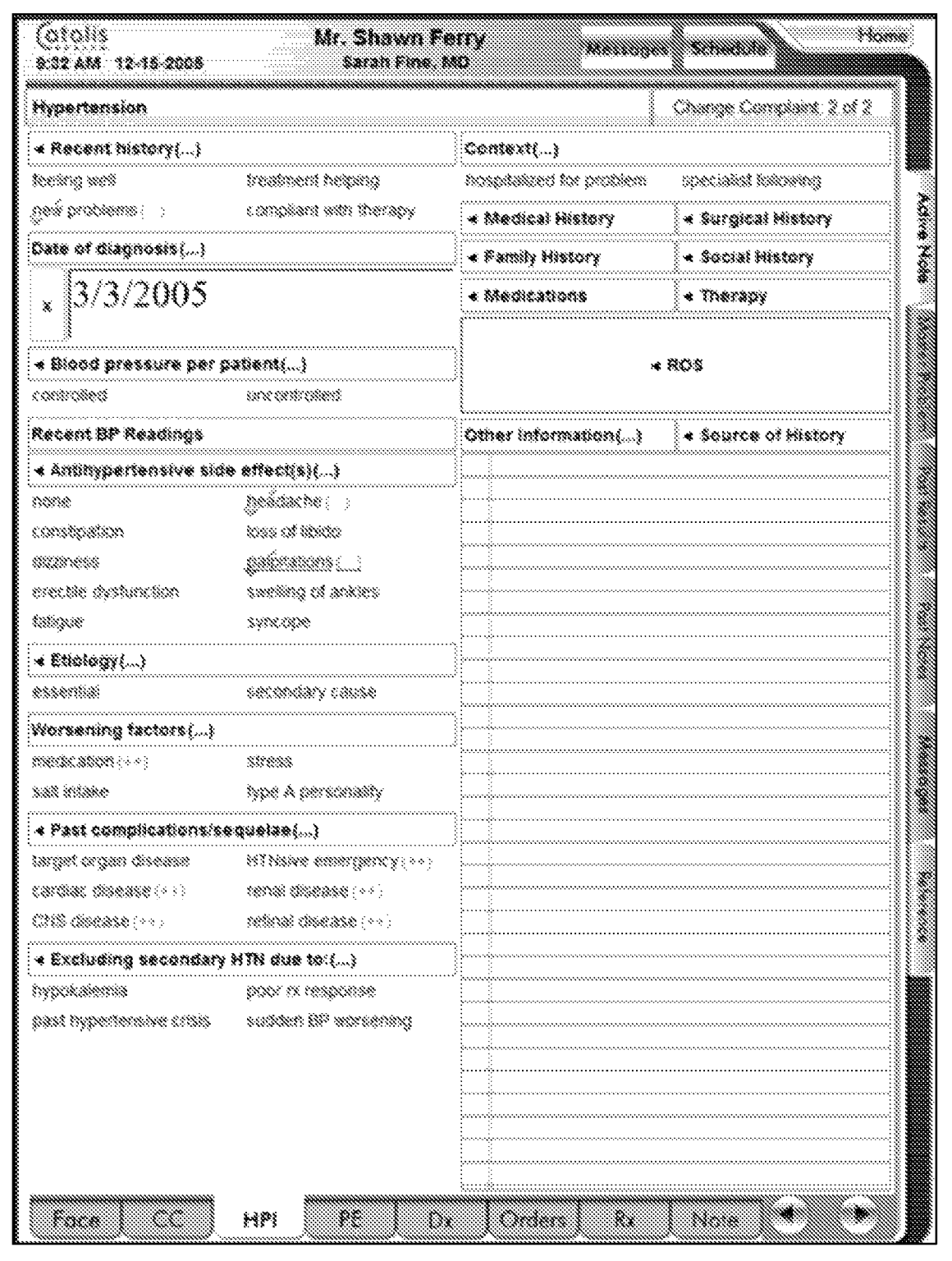

As illustrated in FIG. 31, the healthcare provider (HCP) may select the HPI tab to acquire a template from which the HCP can enter a history of present illness. As FIG. 31 illustrates, the patient has bipolar disorder and is failing phase one treatment (Li) by decompensating and displaying hypomania. The HCP may also access a template to record history of present illness findings associated with the hypertension, as illustrated at FIG. 32.

Figure 33:
Figure 34:
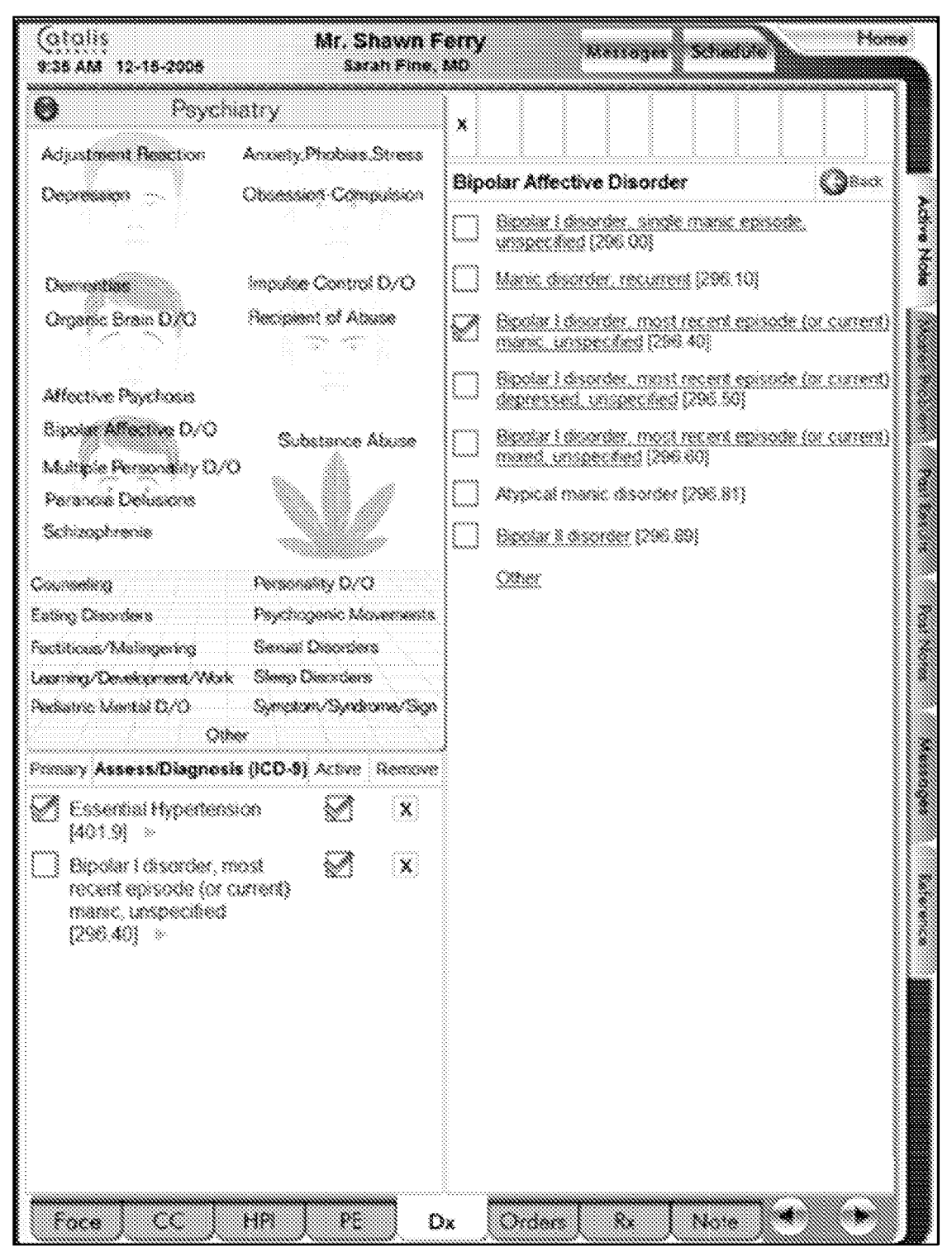

Generally, after entering the history of present illness for each template selected as a complaint (e.g., hypertension and bipolar disorder), the HCP may select the physical exam ("PE") and may enter the physical exam findings. Further, the HCP may select the diagnosis tab ("Dx") to enter diagnoses. As illustrated in FIG. 33, the HCP's may diagnose the patient with the new onset hypertension ("essential hypertension"). As illustrated, this diagnosis may be entered by navigating graphically to a specific system ("cardiovascular"), selecting a category of diagnosis ("hypertension"), and selecting a specific diagnosis ("essential hypertension"). In addition, the HCP may enter a second diagnosis regarding the patient's bipolar disorder, as illustrated in FIG. 34. For example, the HCP may navigate to a system ("psychiatry"), select a category of diagnosis ("bipolar affective D/O"), and select a specific diagnosis ("bipolar disorder most recent episode (or current) manic, unspecified").

Figure 35:
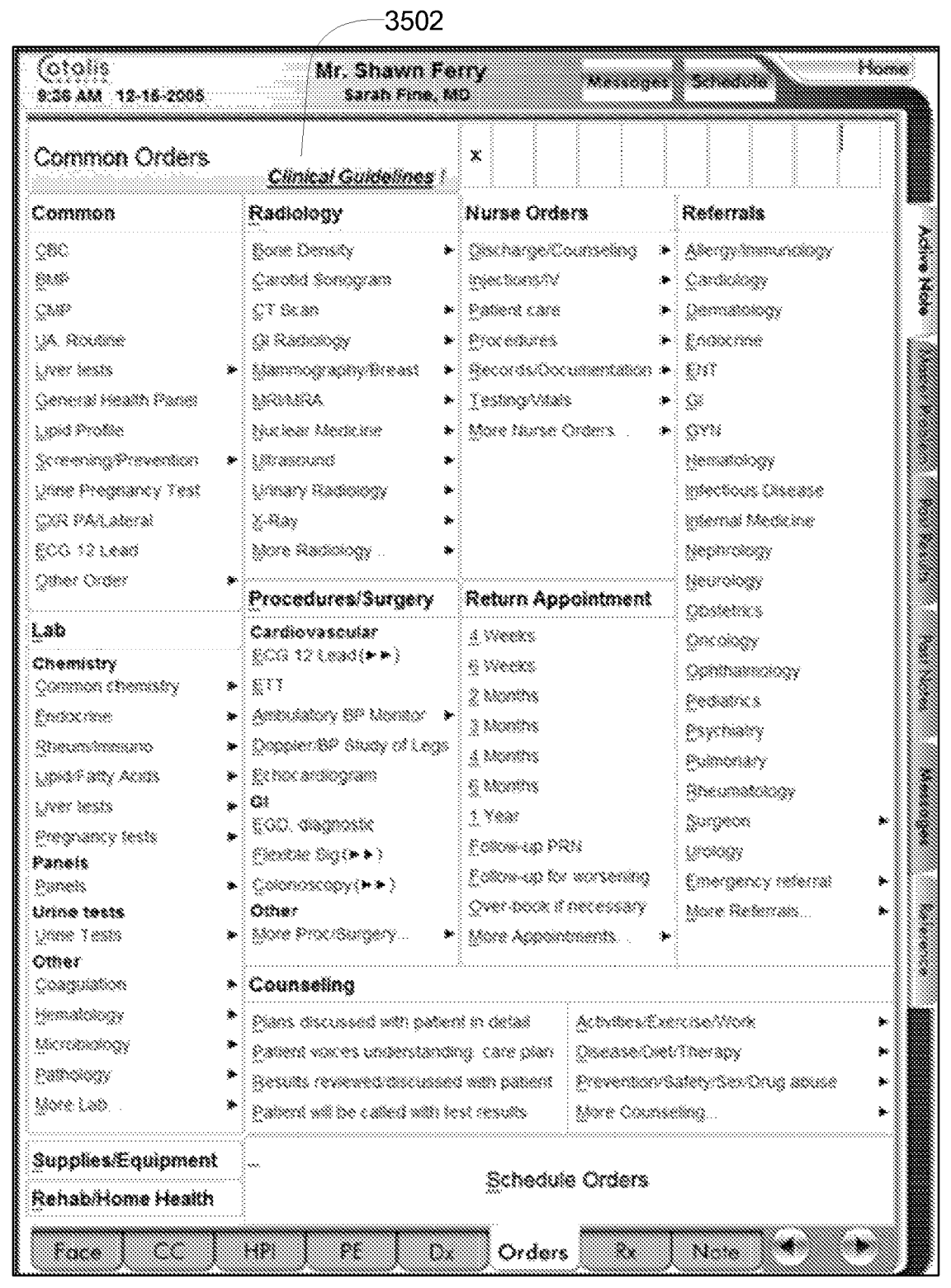

Subsequently, the HCP may select the "orders" tab to navigate to the orders screen, as illustrated in FIG. 35. The illustrated orders screen includes a number of categories of standard orders that are not associated with this patient or his diagnoses—"common", "radiology", "nurse orders", "referrals", "lab", "procedure/surgery", "return appointment", and "counseling". In addition, this screen illustrates a "clinical guidelines" item 3502, indicating that the system has selected some recommended orders associated with the current patient. In this example, the HCP activates the "clinical guidelines" notification and a system may display a set of recommended orders associated with the current patient, as illustrated in FIG. 36.

Figure 36:
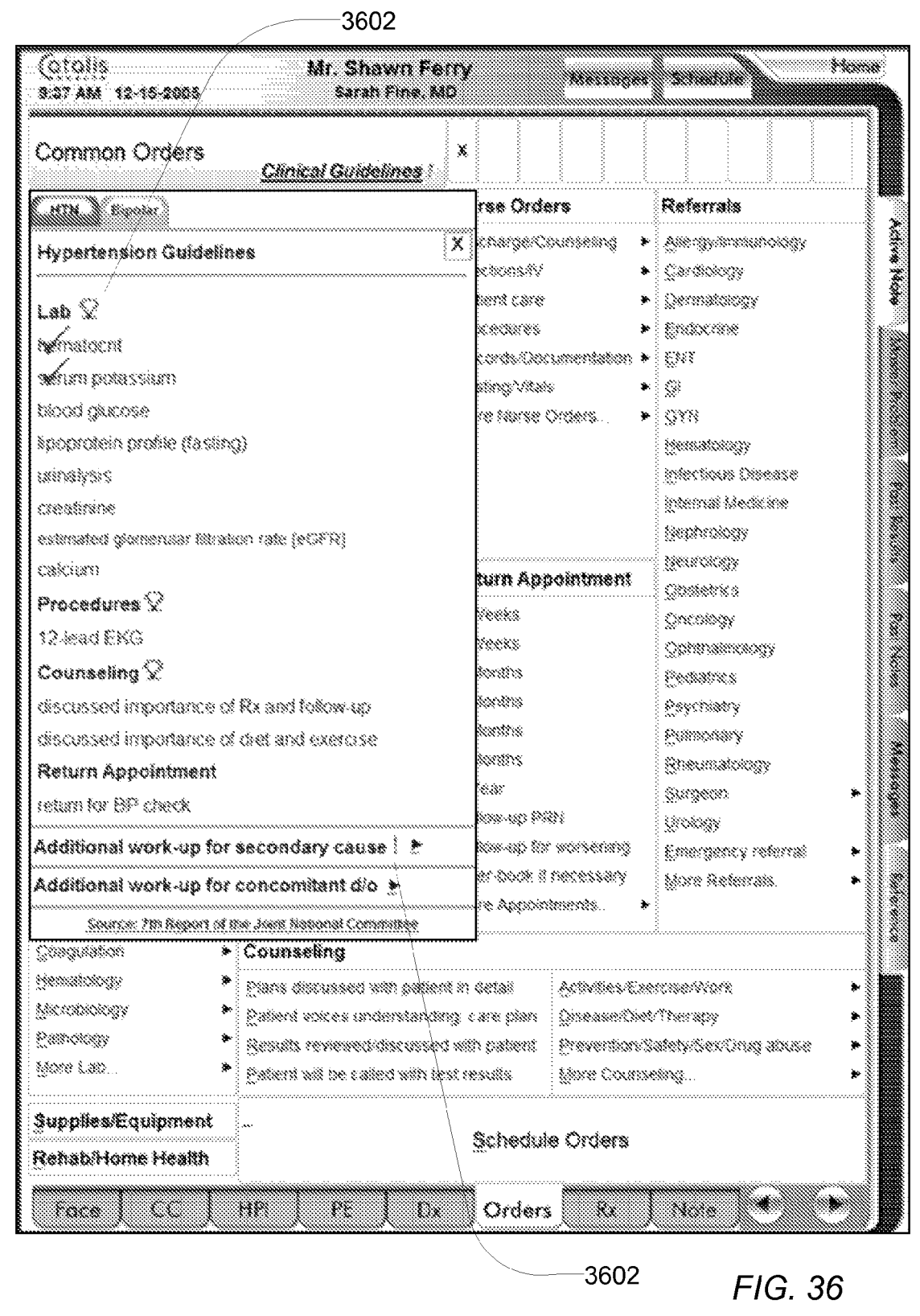
Figure 37:
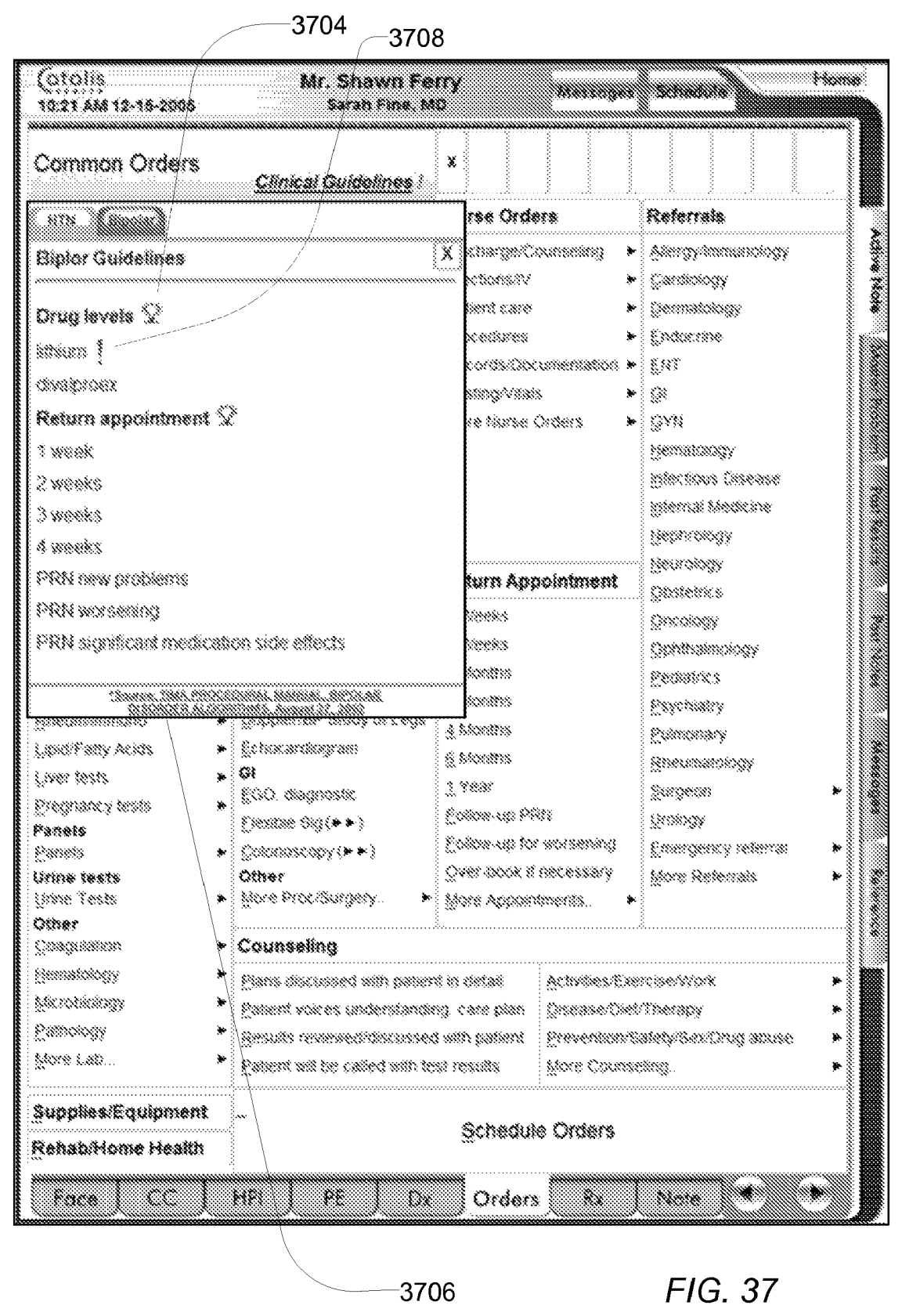

As FIG. 36 illustrates, the system may display a list of orders associated with the hypertension diagnosis. Additionally, the system may display two tabs—"HTN" and "Bipolar". In the event that there are more diagnoses, the system may display more than two tabs, such as displaying a number of tabs equal to the number of diagnoses for which the system has relevant recommended orders. As illustrated in FIG. 36, when multiple diagnoses have relevant recommended orders, this exemplary embodiment provides two lists of recommended orders and allows the HCP to switch between the lists by selecting a tab associated with each order. As illustrated in FIG. 37, the HCP may switch from the hypertension list of recommendations to the bipolar list of recommendations. When the HCP selects the "HTN", the system may display the recommended orders associated with the hypertension diagnosis and, when the HCP selects the "bipolar" tab, the system may display the recommended orders associated with the bipolar diagnosis, as illustrated in FIG. 37.

In this example, individual items may be selected and thereby ordered directly using the displayed screen. For example, FIG. 36 illustrates that the HCP may select the "hematocrit" and "serum potassium" lab orders. In this example, an icon 3602 next to classes of orders (e.g., "lab", "procedure", "counseling") may be selected in order to display additional information about the rationale, algorithm, or authority that justifies these recommendations. As illustrated, the "hypertension guidelines" screen lists recommended orders for the basic diagnosis of hypertension. Because the patient displays some additional symptoms, there may be additional recommendations under the "additional work up for secondary cause" portion of the screen. To indicate the presence of additional recommendations, the system may highlight this item by placing an icon ("!") 3604 next to this menu item.

As illustrated in the "bipolar" list of FIG. 37, the HCP can access additional information about a category of recommendations ("drug levels", "return appointment") or can select an item 3706 at the bottom of the page to get a full document on the treatment algorithm ("TIMA procedural manual, bipolar disorder algorithms, Aug. 27, 2002"). As such, the system may provide a method for accessing brief information about specific topics ("drug levels") or detailed information about the entire diseased treatment regimen. Note that the latter can often span 10's of pages of text, so the option to provide more focused information about specific topics can inform the HCP while limiting the amount of time spent by the HCP in reviewing the information. Also note that the system may place a warning icon, such as the icon 3708 next to the "Lithium" item.

Figure 38:
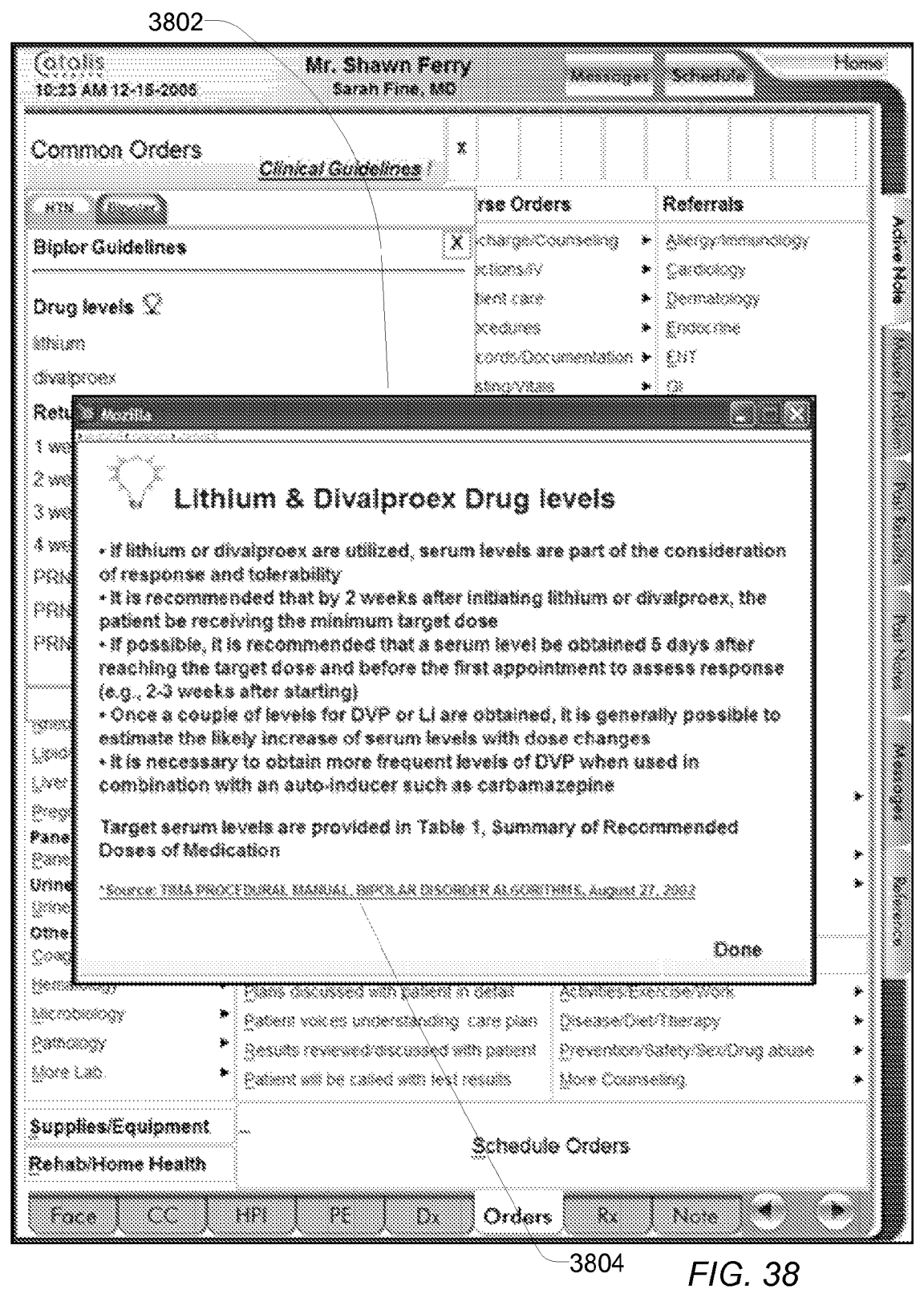

In an example, the HCP may select the "information" icon 3704 associated with the "drug levels" category. In response, the system may display information 3802 about the selected topic, as illustrated in FIG. 38. This display also may include a link 3804 to additional information about the treatment.

Figure 39:
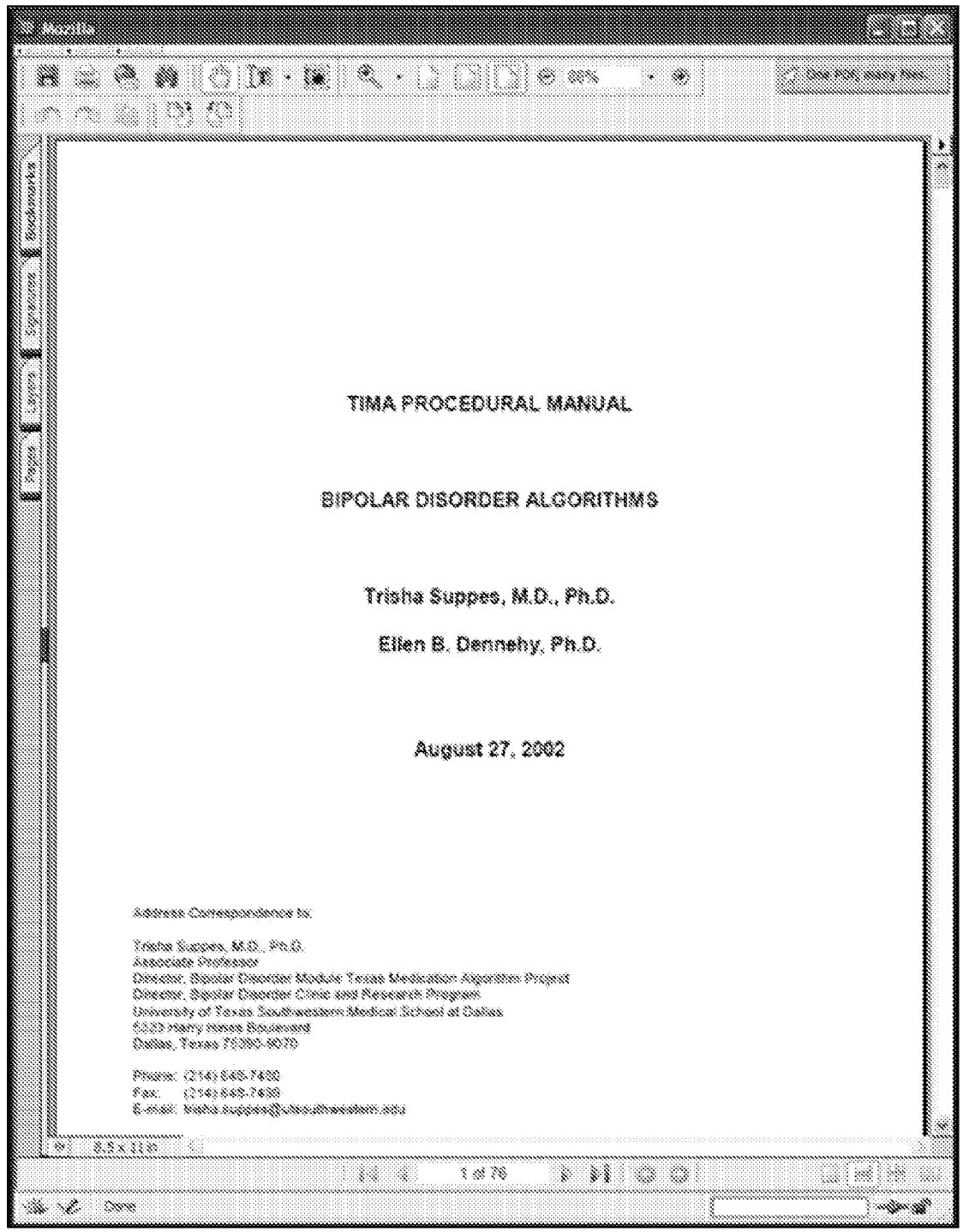

In an example, selecting the link 3804 may result in display of an additional document. For example, as illustrated in FIG. 39, selection of the link 3804 may open an Adobe portable document format (PDF) file "TIMA procedural manual: bipolar disorder algorithms", a 76 page document that the HCP can read using the tablet device on which the EMR is displayed.

Figure 40:
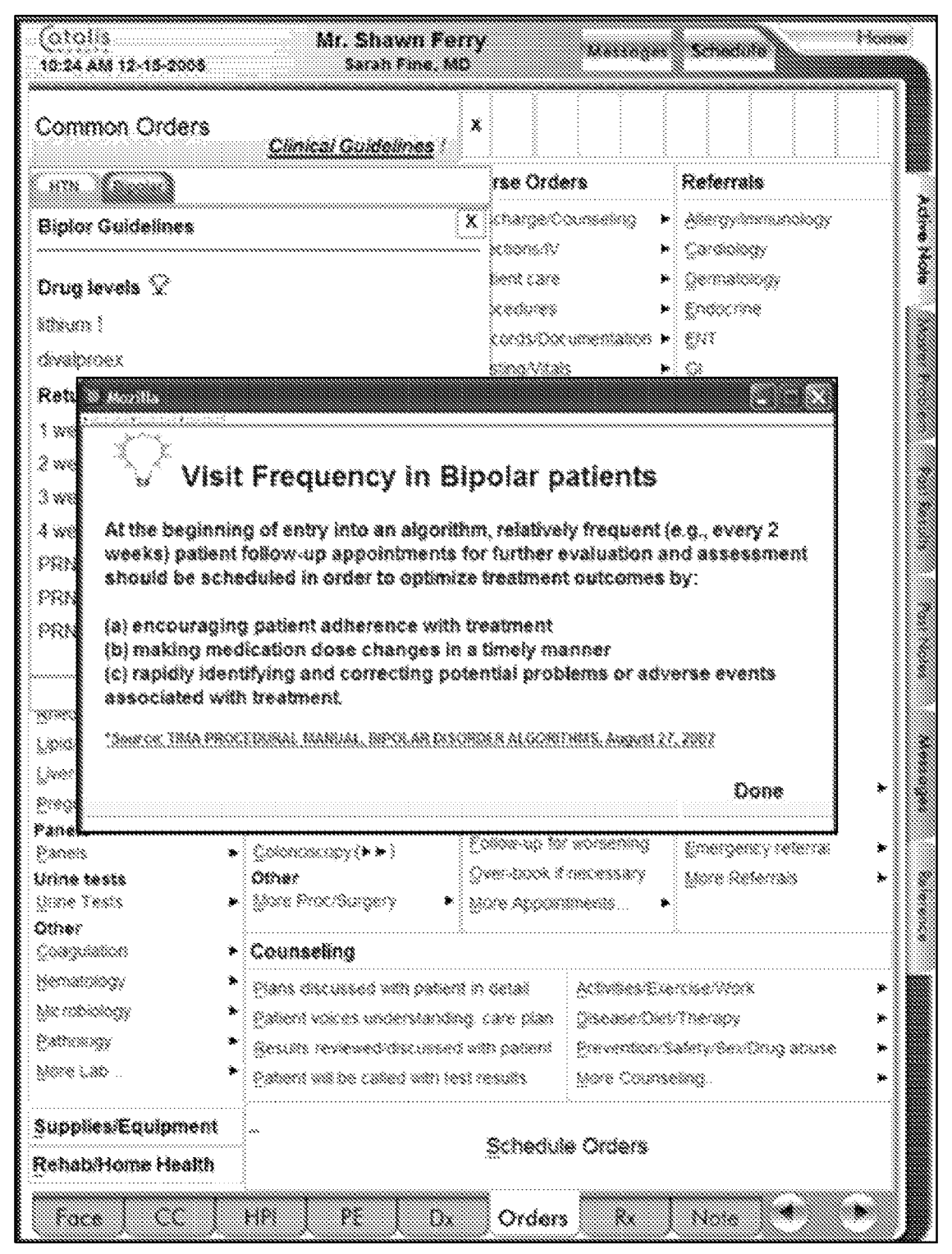

In another example, when the HCP selects the information icon associated with "return appointment" from the bipolar guidelines list, the system may display the reasoning and an authority behind the recommended return appointment items, as illustrated in FIG. 40.

Figure 41:
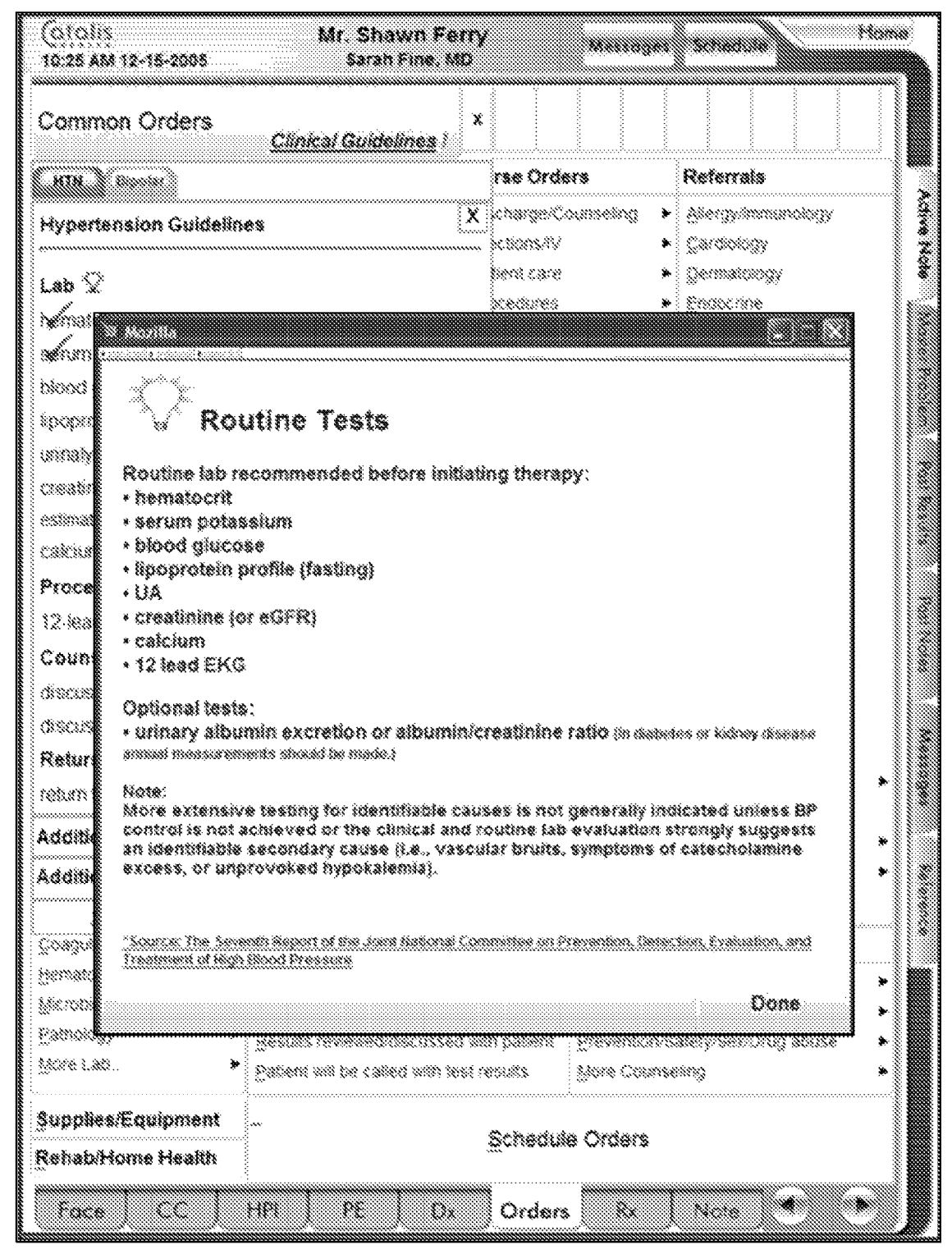

Returning to the "hypertension guidelines" list, when the HCP selects the "information" icon associated with the "lab" test, the system may display a short summary of the rationale and authority behind the recommended tests, as illustrated in FIG. 41. Note that the system may lists three types of tests: routine tests that should generally be ordered, optional tests that are recommended in some circumstances, and a discussion of "not recommended" tests (tests that should only be ordered under specific circumstances.)

Figure 42:
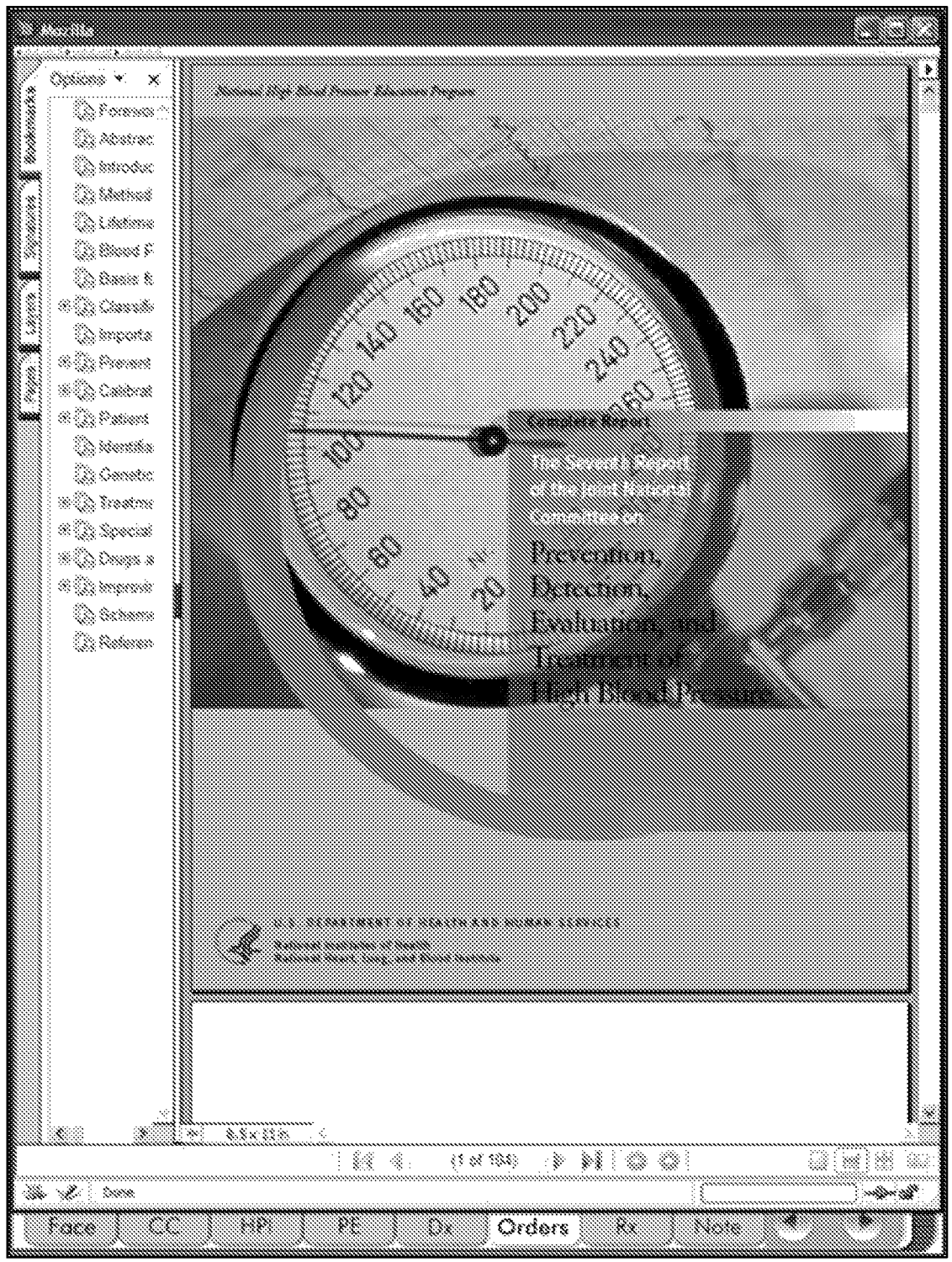

In general, from a screen listing a set of recommendations or a screen providing summary information about a set of recommendations, the HCP may select to see a full report on the treatment. As illustrated in FIG. 36 and FIG. 41, the recommendations were derived from "the seventh report of the joint national committee on prevention detection evaluation treatment of high blood pressure", and the system may provide access to this full report when the HCP selects to see more information, as illustrated in FIG. 42.

Figure 43:
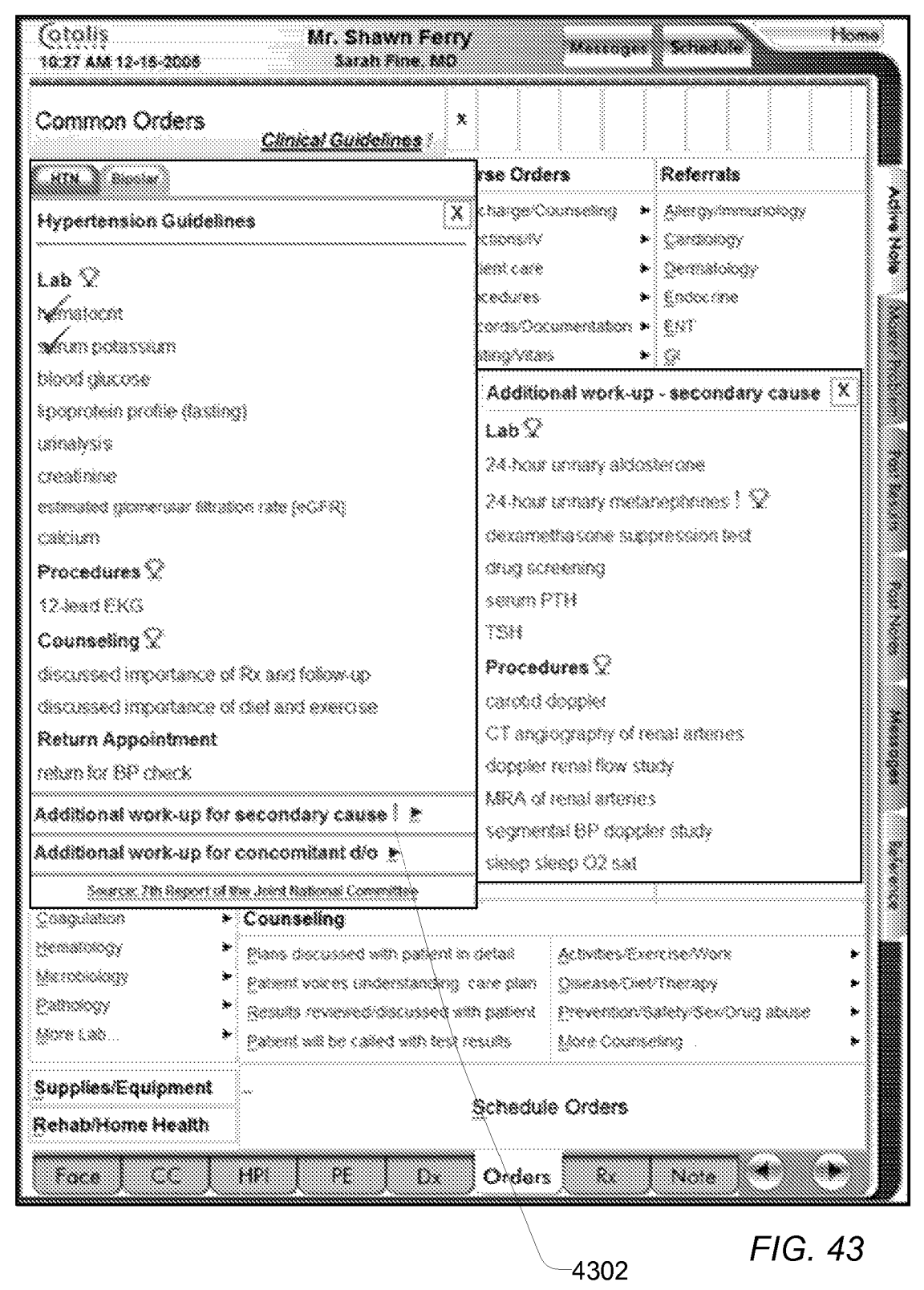

Because the exemplary patient has headaches and palpitations in addition to the hypertension, the system may select additional recommendations for secondary causes. As illustrated in FIG. 43, the system may highlight the such recommendations on screen by placing an icon 4302 with the secondary causes link. In an example, selecting the icon 4302 or the link displays the recommended items, as illustrated in FIG. 44.

Figure 44:
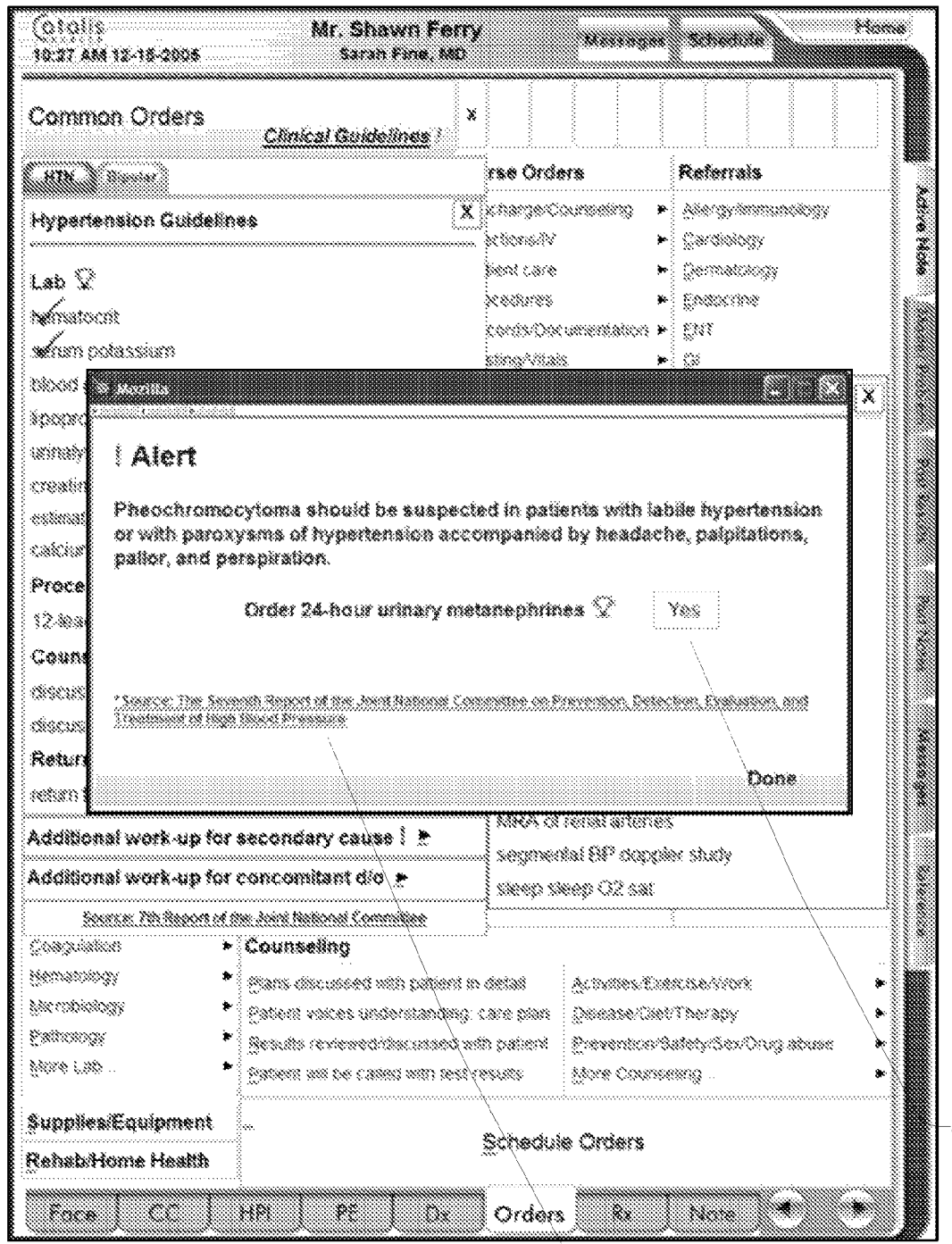

In the example illustrated in FIG. 44, the system may display an additional recommended test relating to a potential secondary cause. The example display may include an icon 4402 to display more information about the specific test, for example, a link to a full report on the recommendations for the disease, and a selection control 4404 to order the test directly from the display.

Figure 45:
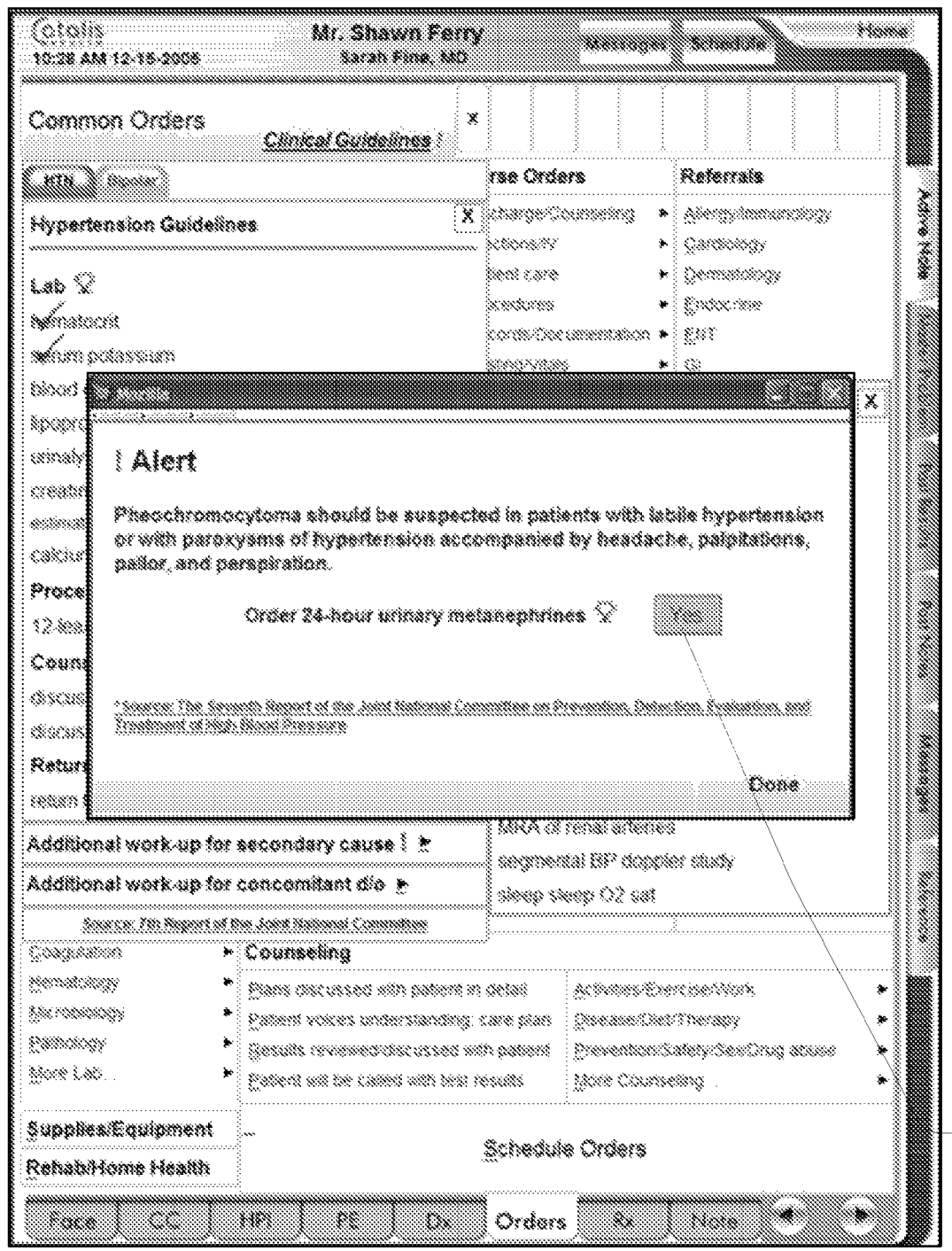
Figure 47:
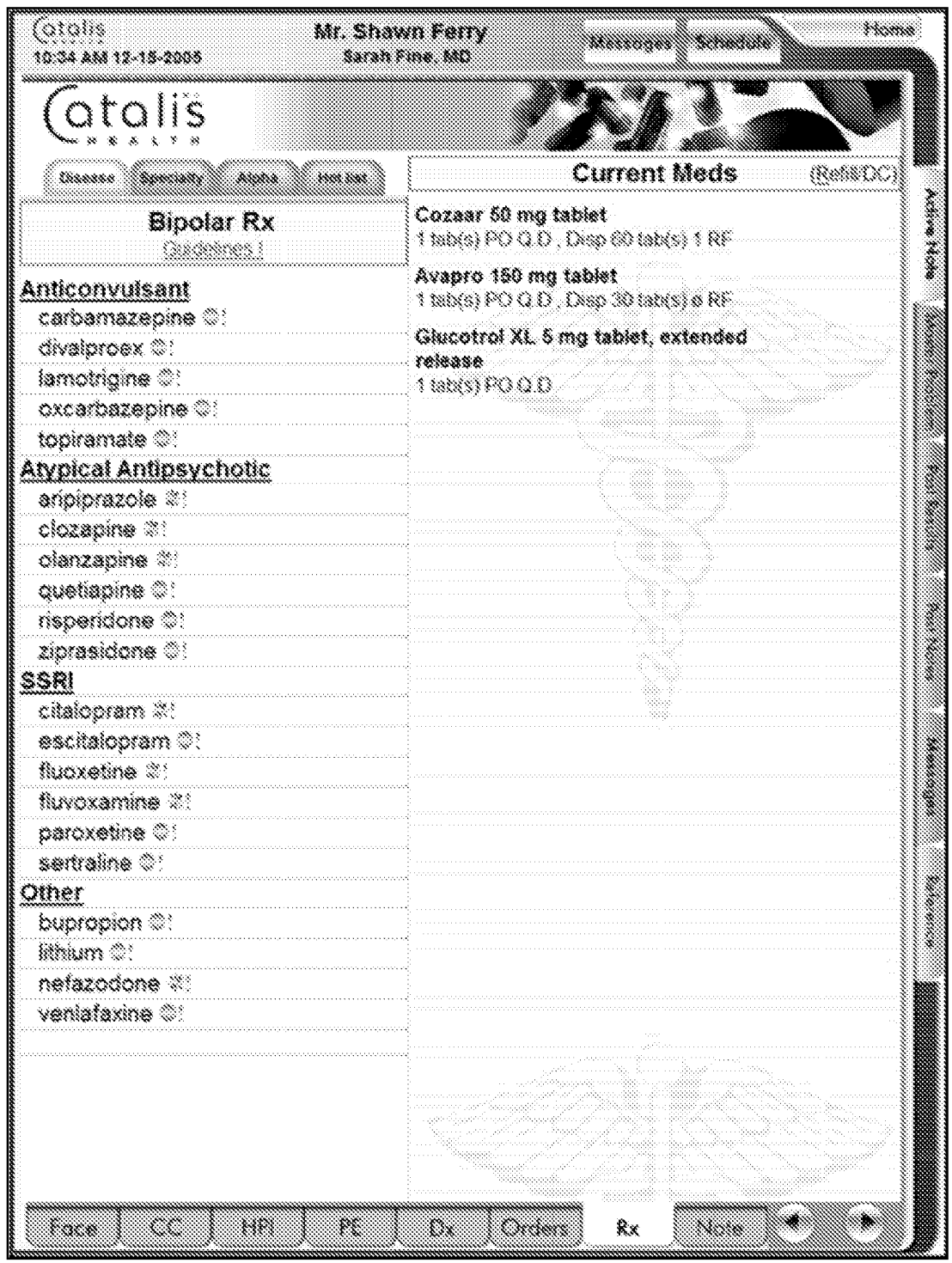

After the system displays is recommended order, the HCP may selects the order directly from the dialog box, as indicated by a change in the icon 4404, such as a change illustrated in FIG. 45. For example, the change may include a color change, shading change, shape change, substitution of the icon, or addition of an icon or image.

Figure 46:
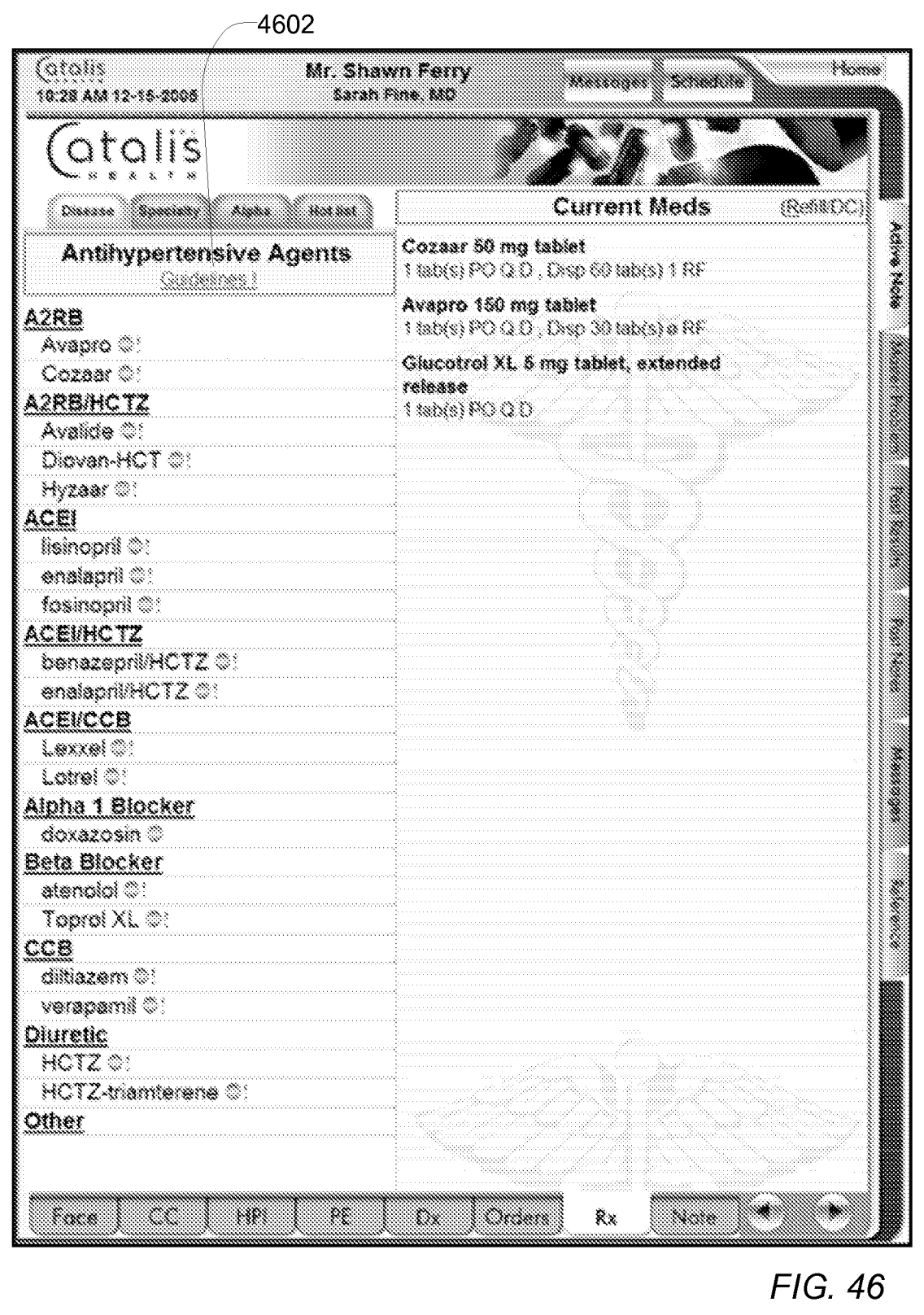

In a further example, the HCP may select the "Rx" tab and the system may display a screen for prescribing medications, as illustrated in FIG. 46. In this example, recommended medications are grouped by category. The system also may display options to view different sets of medications by: "disease" (medications recommended based on diagnosis), specialty, alphabetical, and hot list (medications often prescribed by the HCP). For example, selecting the "disease" tab may display medications recommended for a specific disease associated with the patient.

In the example illustrated in FIG. 46, a "guidelines" link 4602 is highlighted with an icon, indicating that there are additional recommendations relevant to the current patient. In addition, medications may be displayed with icons, such as icons indicating one of three formulary status levels for the medications: (1) (gold circle in the figure) "preferred, no prior authorization required", (2) (asterisk; not in current figure but will be illustrated in later figure) "prior authorization required", (3) (X; not in current figure but will be illustrated in later figure) "not covered". In addition, some medications may be associated with a "guideline alert" (!) indicating that the medication is recommended for the current patient. In another example, illustrated in FIG. 47, a recommended list of medications for bipolar disorder is displayed. Note that it includes both "no prior authorization required" items and "prior authorization required" items.

Figure 48:
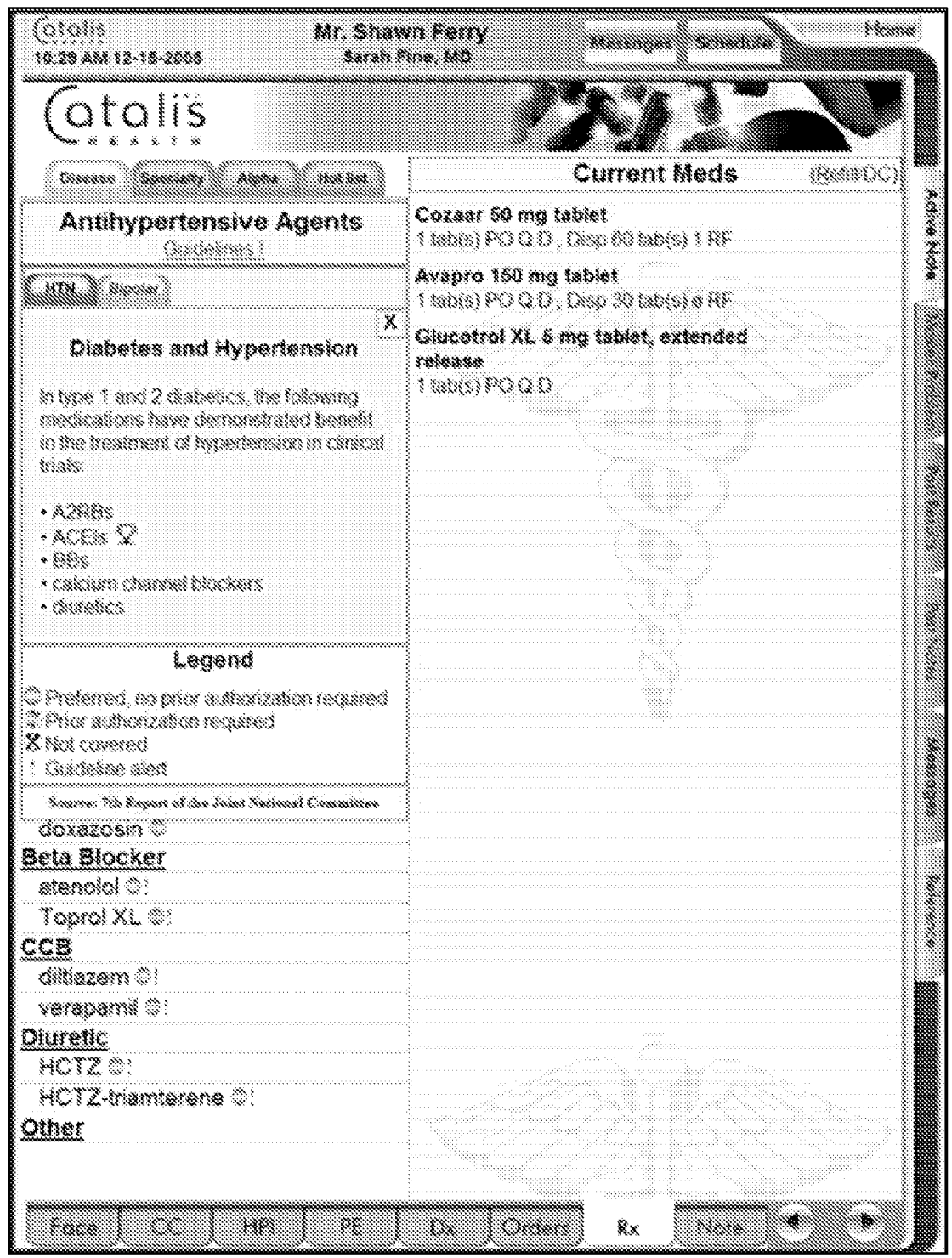

In an example, selecting the "guidelines" link, such as link 4602 of FIG. 46, may result in the display of additional information about the recommendation. As illustrated in FIG. 48, the system may include a control for switching between recommended lists for the different diagnoses associated with the current patient. In the illustrated example, tabs provide the ability to switch between hypertension and bipolar recommendations.

Figure 49:
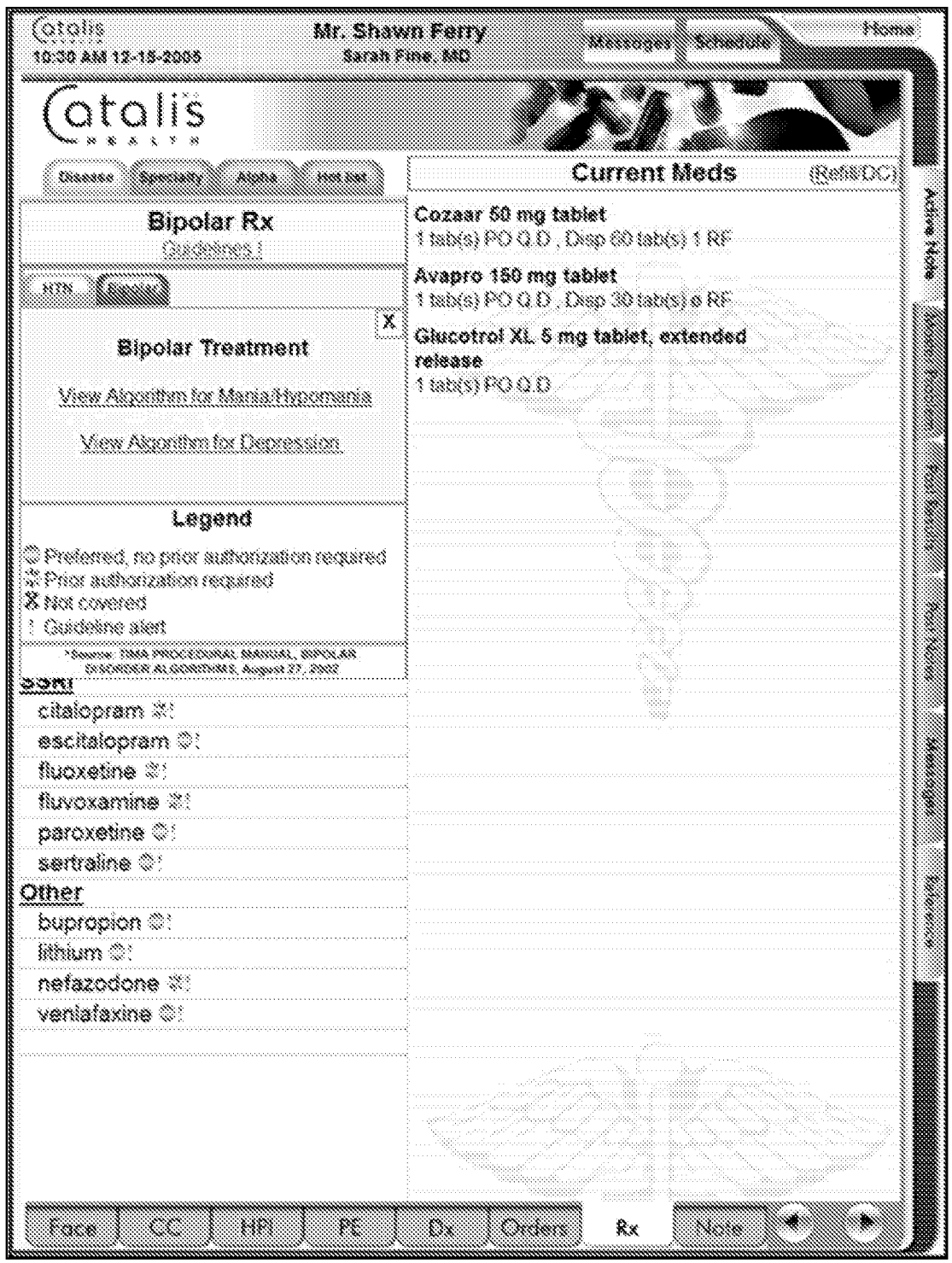
Figure 50:
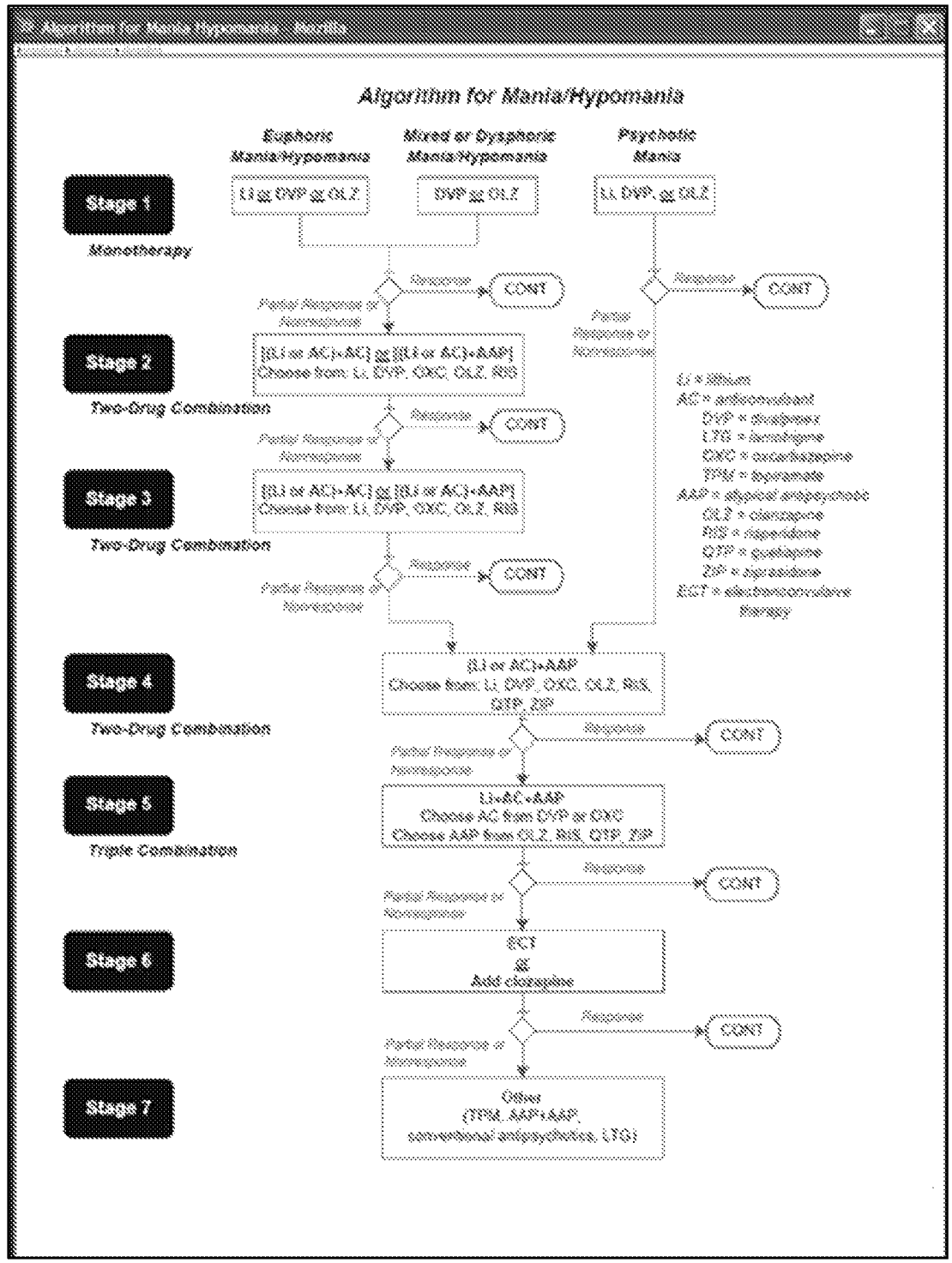
Figure 51:
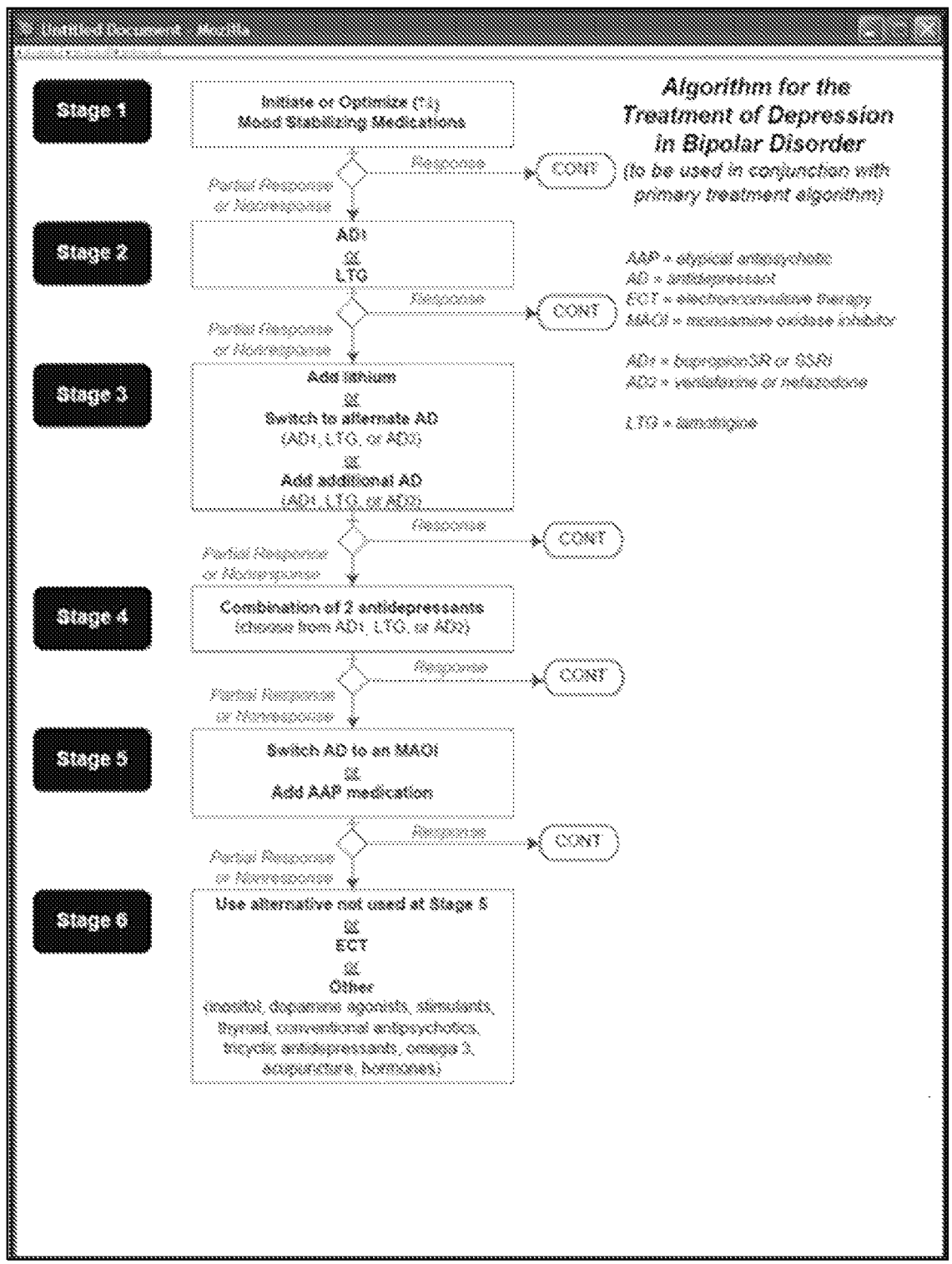

As illustrated in FIG. 49, additional information about bipolar treatment may include the option to view treatment algorithms. For example, when the HCP selects "view algorithm for media/hypomania", the system may display a graphical and textual depiction of the recommended phased-treatment algorithm, as illustrated in FIG. 50. In another example, when the HCP selects the algorithm for "depression", the system may displays the algorithm for the treatment of depression bipolar disorder, as illustrated in FIG. 51.

Figure 52:
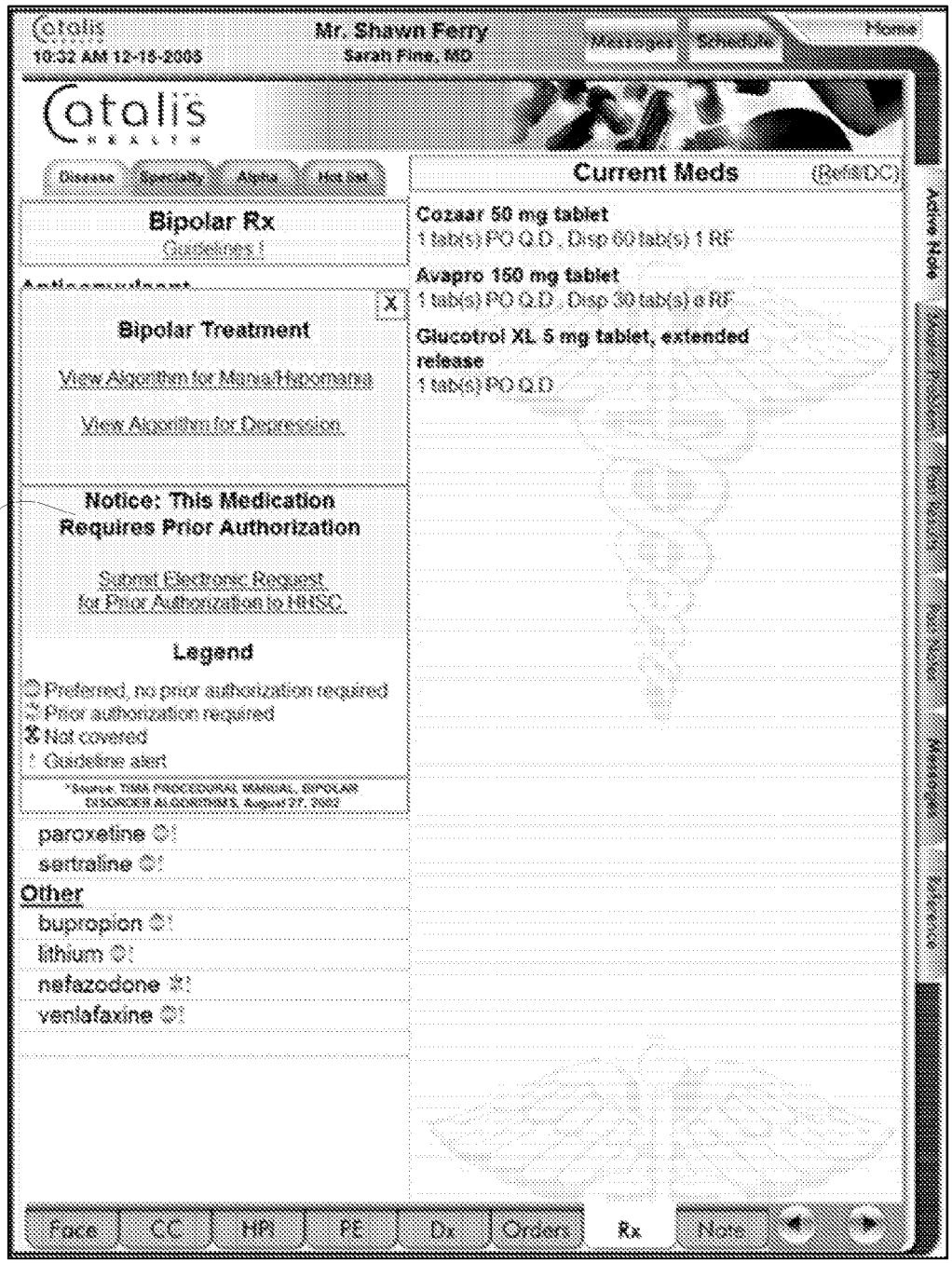
Figure 53:
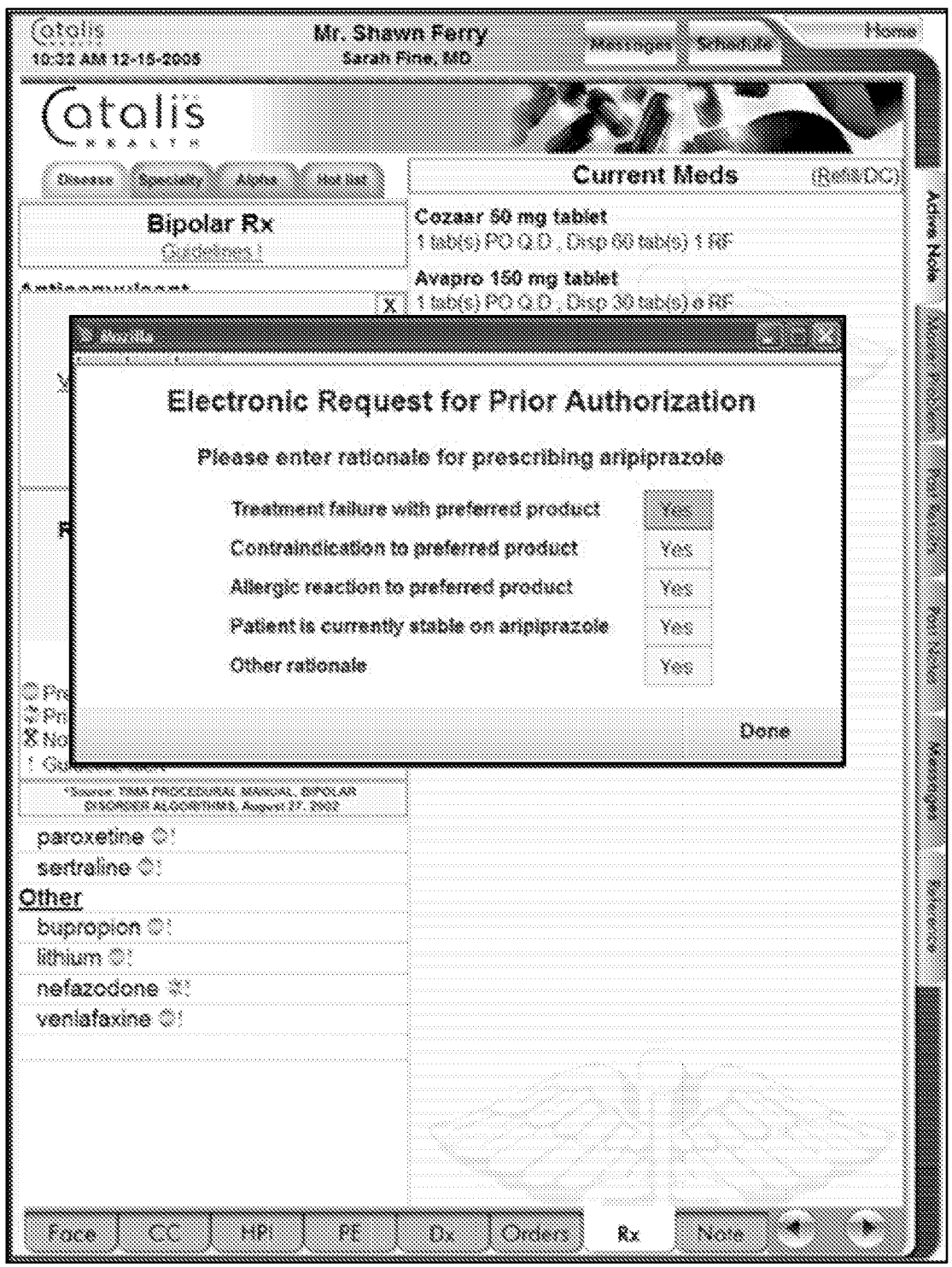

In a further example, when a HCP selects a medication for which prior authorization is required, the system may display a notification 5202, as illustrated in FIG. 52. This notification 5202 provides the option to "submit electronic request for prior authorization". In an example, when the HCP selects the option to submit a prior authorization request, the system may display a form that allows the HCP to enter relevant clinical information, as illustrated in FIG. 53. For example, the HCP may enter a finding that "treatment failure with preferred product" (in this case, the patient is no longer responding to the original lithium treatment). In an embodiment, one or more elements in the form may be filled out automatically by the system by drawing from store information about the patient. In another embodiment, the HCP may select the relevant items from a list.

Figure 54:
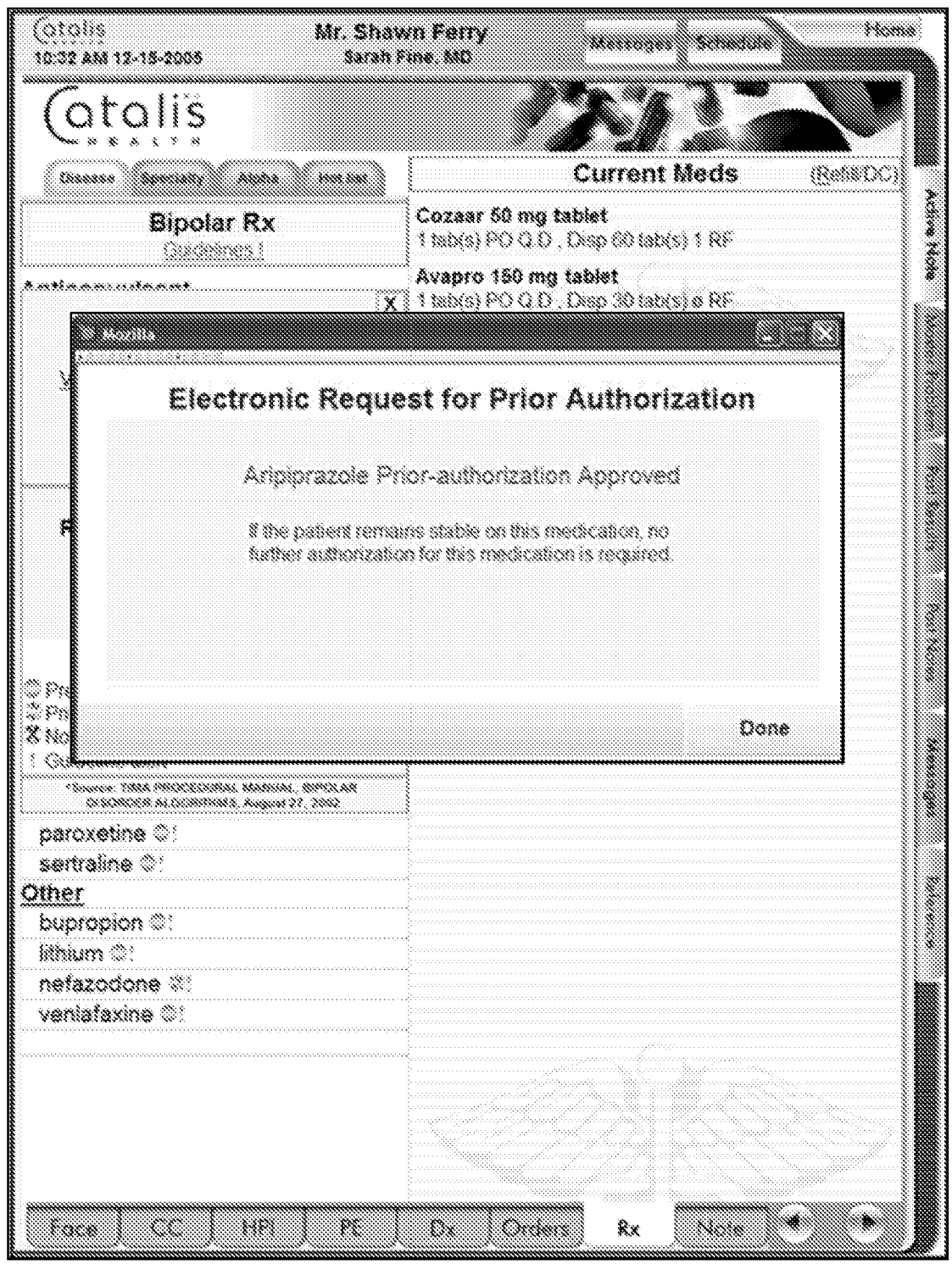

After the HCP issues a prior authorization request, the system may make a determination of whether prior authorization can be granted and may store and display this determination, as illustrated in FIG. 54. In an embodiment, the determination is made automatically by comparing information elements against a stored set of criteria. In another embodiment, the determination is made by separate human authorization. In a third embodiment, the system automatically approves request in some cases but, refers others to a human authority or separate system associated with a DMA, such as a payer.

In particular, when the HCP is finished entering information about the patient, the selected orders may be sent to fulfillment entities (e.g., pharmacies, labs, appointment calendar). For example, an order may be sent to a nurse's system, encouraging a nurse visit to the patient. In another example, an order may be forwarded to a radiology facility or a lab. The patient may be contacted by the radiology facility or lab, for example, to facilitate completion of the order. In a further example, a prescription may be forwarded to a pharmacy, such as a pharmacy previously specified by the patient. Where follow up appointments are specified, a receptionist may be notified and may schedule an appointment with the patient.

Figure 55:
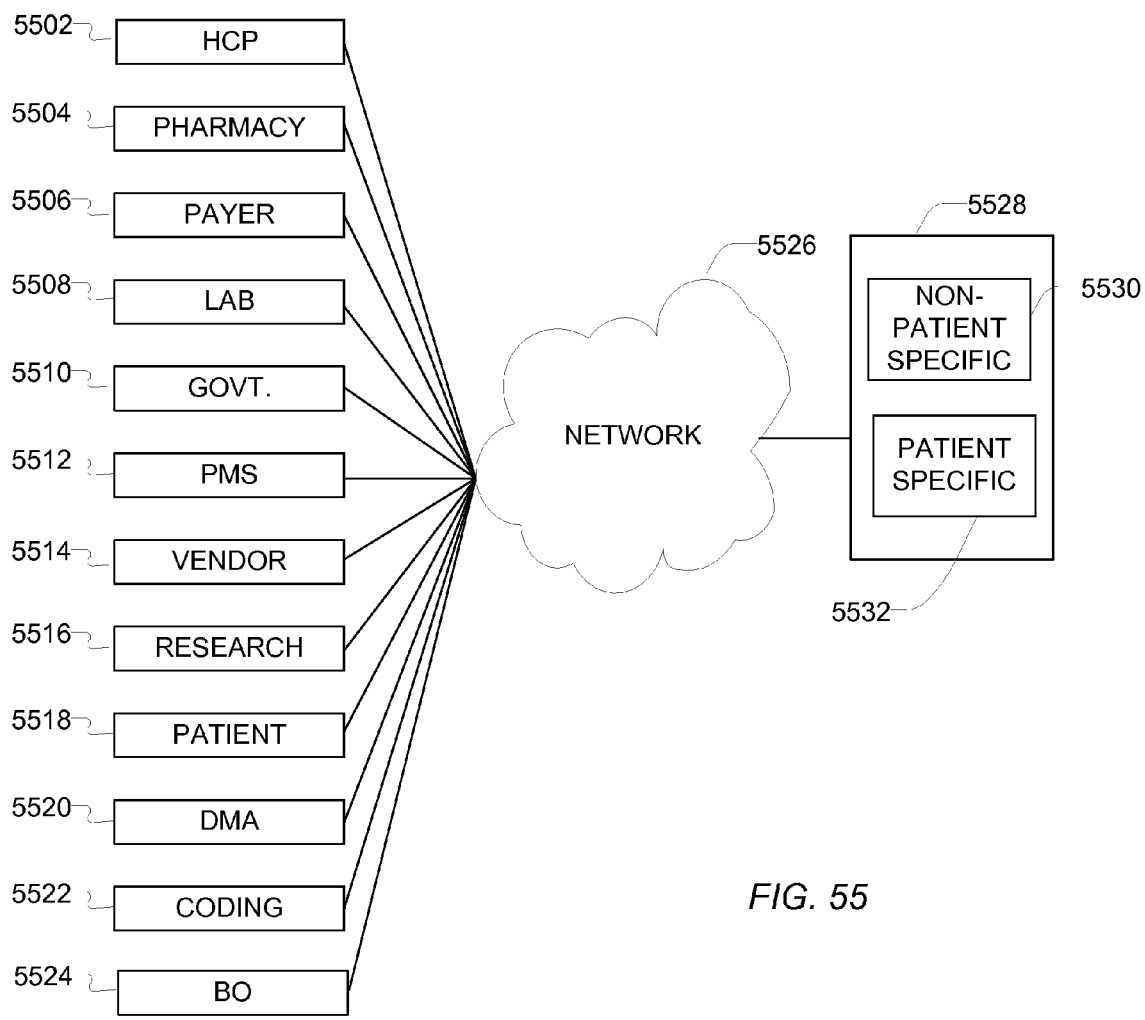
FIG. 55 includes an illustration of an exemplary system for transferring patient data.

Once findings have been collected or medical orders identified, data may be shared with various systems external to the HCP system. As illustrated in FIG. 55, at least one HCP uses an HCP interface 5502 to access via a network 5526 a server 5528 that stores at least one patient medical record 5532 and that stores non-patient specific data 5530. Other users also may accesses the server 5528 via the network 5526 via at least one other interface.

In an embodiment, the server 5528 comprises multiple computer devices connected by a network 5526. In another embodiment, the server 5528 is embodied in two sets of at least one computer machines and the patient specific medical data 5532 are stored on first set of at least one machines and the non-patient-specific medical data 5530 are stored on a second set of at least one machines. In an example, the HCP interface 5502 may access data from both sets of machines and the at least one other user accesses data from at least one set of machines. Alternatively, the server 5528 may be a single server component.

In alternative examples, the HCP interface 5502 may communicate with the server 5528 via a local area network and other access interfaces may communicate with the server 5528 via wide area networks or global networks. In a further example, server components associated with the patient specific data 5532 may be located locally to the HCP interface 5502 and server components including non-patient specific data 5530 may be located remotely from the HCP interface 5502.

Examples of other users and their associated interfaces include pharmacies 5504, payers 5506, labs 5508, government entities 5510, practice management systems (PMS) 5512, vendors 5514 such as pharmaceutical companies, researchers 5516, patients or patient agents 5518, disease management advisors 5520, coders 5522, or back office users 5524 (e.g., billing managers or office managers). While the disease management advisor 5520 is illustrated as a separate entity, other users (e.g., payers 5506, government entities 5510, vendors 5514, researchers 5516, or coders 5522) may function as disease management advisors.

In an exemplary embodiment, different classes of users may access the system via different interfaces. Furthermore, different classes of users may be granted different levels of access to non-patient-specific data and patient-specific data. For example, in an embodiment, a physician may be able to read non-patient specific data 5530 representing formularies and is able to both read and write patient-specific data 5532 relating to that physician's patients. In another example, a pharmacy benefits management company may be able to update non-patient-specific data 5530 relating to the formularies managed by that PBM and may be able to read a subset of patient-specific data 5532 relating to medication treatments for patient's enrolled in that PBM. In another embodiment, researchers 5516 may be able to access patient information that has been de-identified or aggregated to protect patient privacy. In a further embodiment, some classes of users have no access to patient specific data 5532, but are able to access non-patient-specific data 5530. For example, in one embodiment, pharmaceutical companies may be able to provide reference information relevant to the treatment of certain classes of patients, and this information will be displayed when the HCP is accessing patient information for a patient belonging to the relevant classes.

In a further embodiment, different classes of HCP users access the system via different HCP interfaces that provide different subsets of functionality. For example, a nurse module provides functionality useful for a nurse's duties and a physician module provides functionality useful for a doctor's duties. In another example, a cardiologist module provides functionality useful for a doctor specializing in cardiology while a pediatrics module provides functionality useful for a doctor specializing in pediatrics.

In an exemplary embodiment, an HCP or other user interface may include a distributed computer system including multiple computer machines connected via a network, at least one of which provides input and output interfaces accessible by the HCP or other user. In an embodiment, different interfaces for different users are implemented in software that may share one or more hardware components. For example, software may run on a wireless tablet-form-factor tablet computer that accesses both patient and non-patient-specific data stored on a per-clinic server that supports both the nurse and physician interfaces. In an embodiment, the same hardware may be used for two different classes of HCP user and may provide different interfaces to the different classes.

In a further exemplary embodiment, users may be provided with access to non-patient specific data in exchange for compensation. For example, researchers may be provided with access to the non-patient specific patient data with which they may perform research, such as determining correlations to disease or revised disease management algorithms.

In a particular embodiment, a third-party data management entity may manage the server system on which the non-patient specific data is stored. For example, the third-party data management entity may manage a server system located locally to the HCP and the local server system may include patient specific data and non-patient specific data. The non-patient specific data may include de-identified data or may include disease management algorithm data. In another example, the third-party data management entity may manage a server system remotely located from the HCP. The remotely located server system may include the non-patient specific data. For example, the third-party data management entity may de-identify the patient specific data or generate correlations from the patient specific data from a server located at an HCP facility and may store the de-identified data or correlations on a remotely located server.

In particular, the third-party data management entity may provide access to non-patient specific data to researchers, government entities, payers, disease management advisors, pharmaceutical companies, coders, or any combination thereof, for a fee. For example, the third-party data management entity may provide licenses to data, may perform data mining tasks at the behest of a subscriber, may provide access to subsets of the data for a fee, or any combination thereof.

In a further exemplary embodiment, the third-party data management entity may compensate a physician for the data. Alternatively, the third-party data management entity may compensate an organization, association, or professional society, organization, or association. For example, when a HCP belongs to a particular professional society, organization or association, the third-party data management entity may share revenue generated from the non-patient specific data acquired from the HCP with the professional society, organization, or association.

Figure 56:
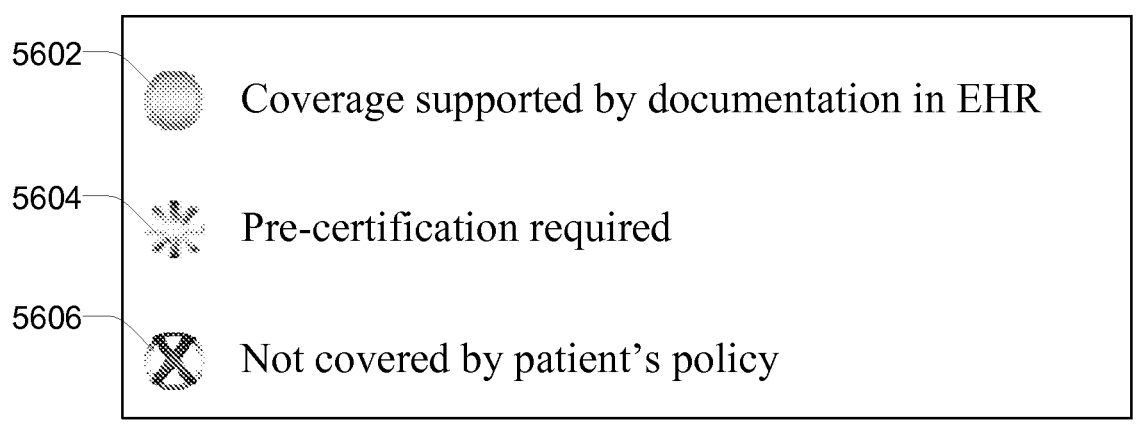

In a particular example, FIG. 56 illustrates icons used in one embodiment to identify orders in different categories. For example, icon 5602 may indicate that coverage for a particular order is supported by the documentation already available in the EHR system, icon 5604 may indicate that precertification is to be requested for the particular order, and icon 5606 may indicate that an order is not covered by a patient's policy. Additional icons can indicate that additional information is to be entered before an order can be supported for a patient's payer plan.

In a particular embodiment, an HCP user may log into the system. To initiate documenting an encounter, the user may select a patient using a patient-selection interface, such as selecting a patient from a list of patients that have appointments with the HCP on the current day. In an example, the HCP user may view a face sheet for the patient (which documents patient status information, such as patient demographic information, allergies, payer, current medications, or active problems). The HCP may access interfaces to select a chief complaint for the patient, enter findings for the history of present illness (HPI) by, for example, checking tri-state boxes (e.g., indicating whether each finding is PRESENT/ABSENT/NO_COMMENT) on a chief-complaint-specific template of discrete findings, enter review of systems (ROS) findings, enter physical exam findings, enter a diagnosis, or view a screen that provides a means for the system to receive medical orders, or any combination thereof. In an embodiment, the system provides a "tab" interface to switch between documentation and ordering tasks, such as those tasks listed above.

Figure 57:
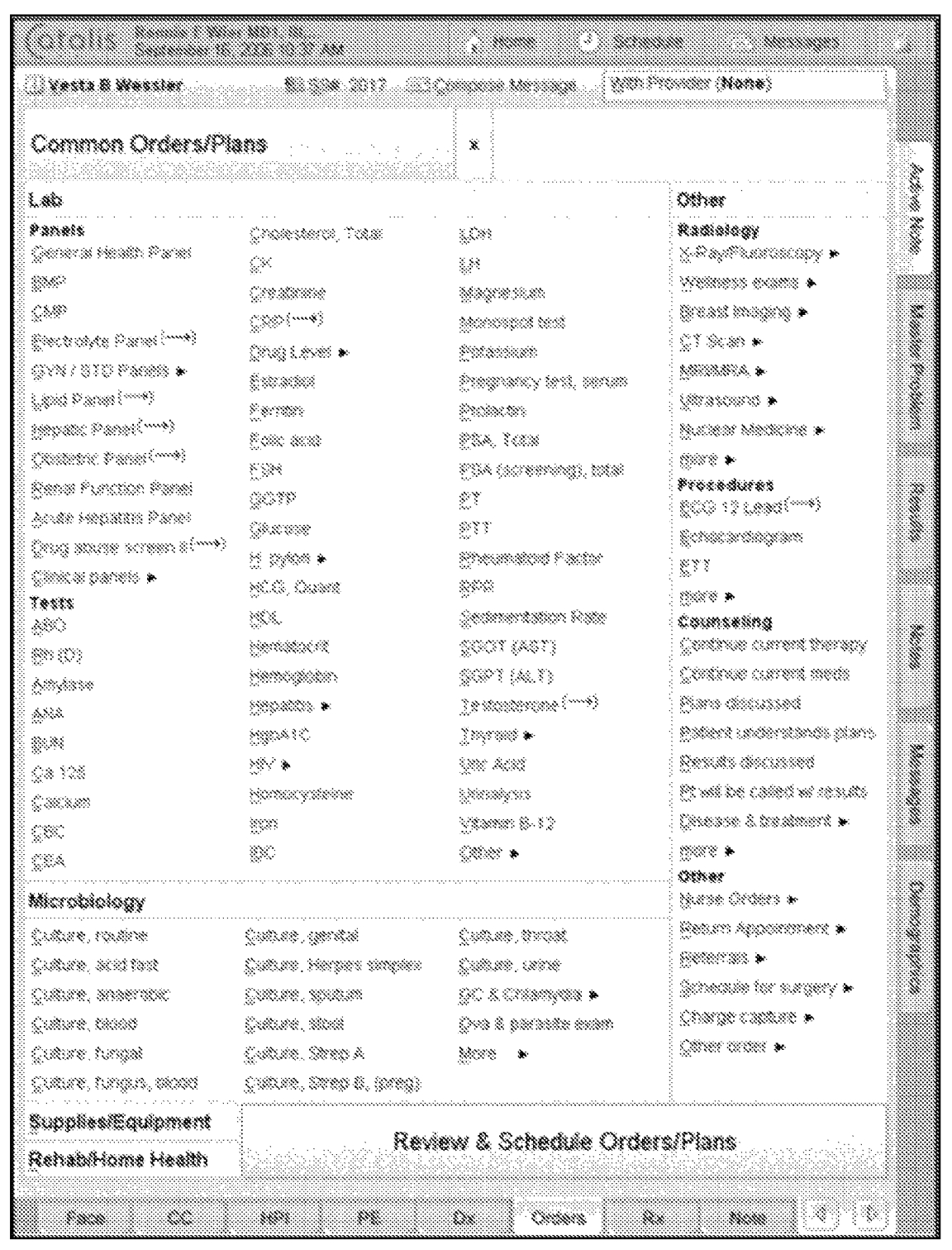

For example, FIG. 57 includes an illustration of an exemplary interface for receiving selection of a plurality of medical orders. The system may display lists of orders or order categories grouped by category, such as Lab, Other, or Microbiology. The system further may display lists of orders or order categories grouped by sub-category, such as Panels, Tests, Radiology, Procedures, and Counseling. In an exemplary embodiment, the system may signify whether displayed orders are approved, require pre-certification, or are not typically covered for the current patient based on the currently stored findings by displaying icons, such as those illustrated in FIG. 56.

As illustrated in FIG. 57, selecting a listed item may result in one of four things. First, selecting the item may cause the selected order to be stored and later transmitted. Such an action is appropriate when, for example, no further information is to be specified about the order or when the order is automatically authorized by the payer for the patient. Second, selecting the item may activate an interface for selecting an order from a selected category of orders. For example, the system may display a list of orders within the category from which the user may select an order. Third, selecting the item may activate an interface for specifying further details about the order. Such an action also may be appropriate when, for example, parameters are to be specified for the order. For example, an "MRI" order uses additional parameters that specify the area of the body targeted by the MRI. In such an example, the system may display an interface to enter parameters for the selected order.

Figure 58:
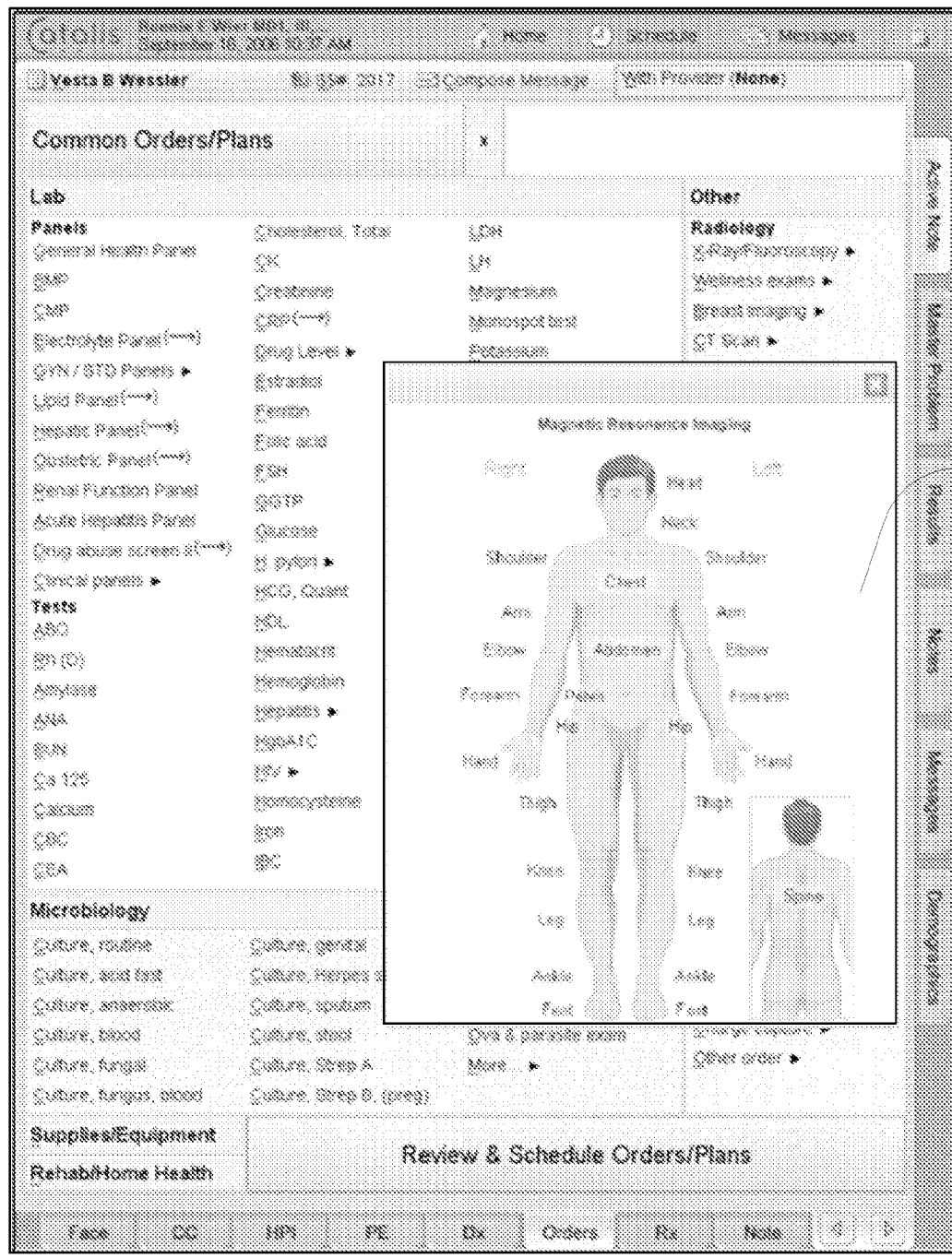
Figure 59:
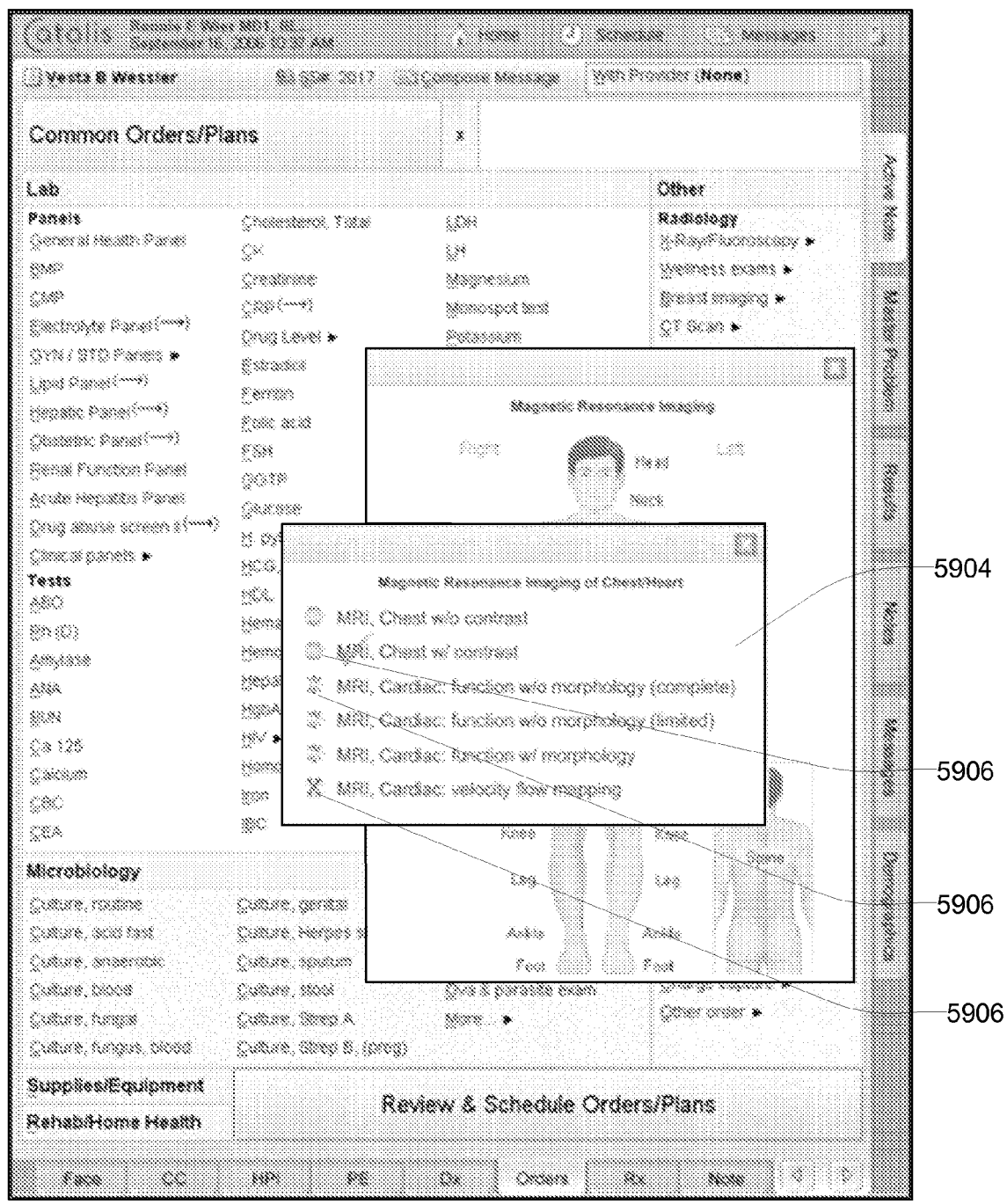

For example, FIG. 58 and FIG. 59 illustrate an embodiment of the third option, activating an interface for specifying further details about the order. When the user selects "MRI", the system prompts the user to provide more details specifying parameters for the MRI. In particular, the system first displays a schematic of the body 5802 that allows the user to specify a general region of the body for the MRI. As illustrated in FIG. 59, the system may include an interface 5904 to display several variations of the MRI that can be ordered for the region specified—for example, MRI Chest w/o contrast, MRI Chest w/contrast, and several variations of cardiac MRIs—corresponding to different parameters to the basic MRI order. In total, the identity of the order and the further details about the order constitute the order data, such order data being generally included with an order request and optionally included with a request for authorization sent to a third-party payer. In general, the order data is stored on electronic media in addition to patient medical findings.

In a further example, selecting the listed item may result in the display of information relating to coverage for the selected order or for variations of the selected order (e.g., different orders within a class or different parameters to an order.) For example, FIG. 59 illustrates an interface that displays icons 5906 identifying category of approval for different MRIs orders for the current patient based on the findings stored for the patient and on the authorization rules for the payer plan associated with the current patient.

Figure 60:
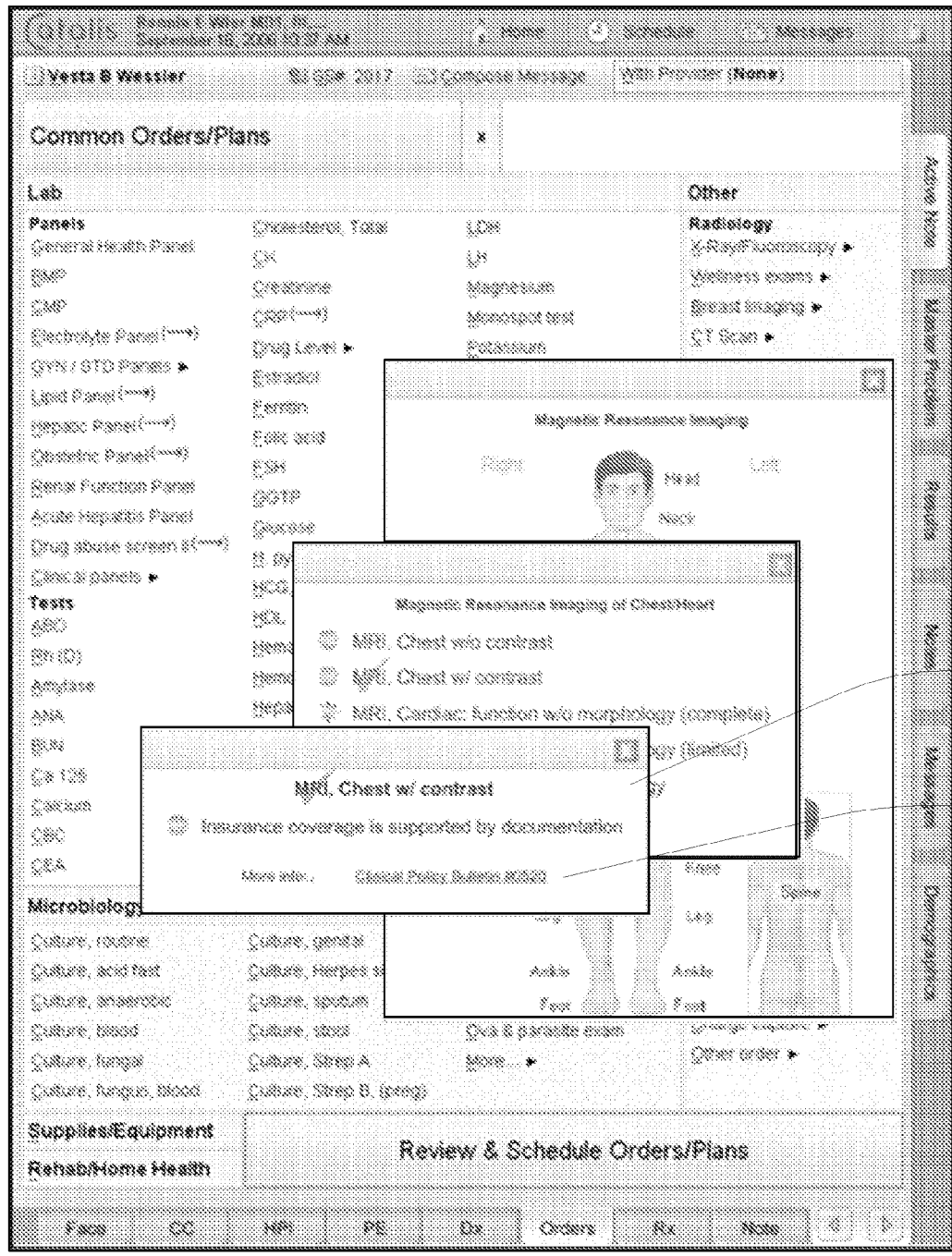

In an example, the findings stored supports the requested order. As such, the system informs the user that the order is covered by the patient's insurance, eliminating the provider/staff looking up coverage information and manually comparing payer rules with patient findings. In a further example, when the selected order is supported for the current patient based on received findings and stored rules, the system immediately notifies the user that the specified order is to be paid for by the patient's payer given the currently stored findings. FIG. 60 illustrates an example message 6008 indicating payer support of an order. Alternatively, notification may be skipped for such "automatic approval items" to reduce disruption to the user's workflow. In another example the notification may display information within an existing window rather than displaying a second dialog window. For example, in an embodiment that generates a narrative documenting the encounter, the system may include approval information in the narrative.

In an exemplary embodiment, the system may provide an interface feature to identify or display the payer policy that supports payment. In an example, the display is immediate. In an example illustrated in FIG. 60, the notation 6010 may indicate that policy bulletin #0520 states the conditions under which the specified test is supported by a particular payer. In an example, the system stores the specific payer policy relating to an order and provides a link or interface for the clinic staff to later retrieve and display this information.

When an order is to be pre-certified, the system may notify the user that an order uses pre-certification, identify relevant criteria for approval, and automatically prepare and transmit an authorization request. Such functionality eliminates tracking payer policies, matching such policies to patient findings, and performing call/fax authorization requests.

Figure 61:
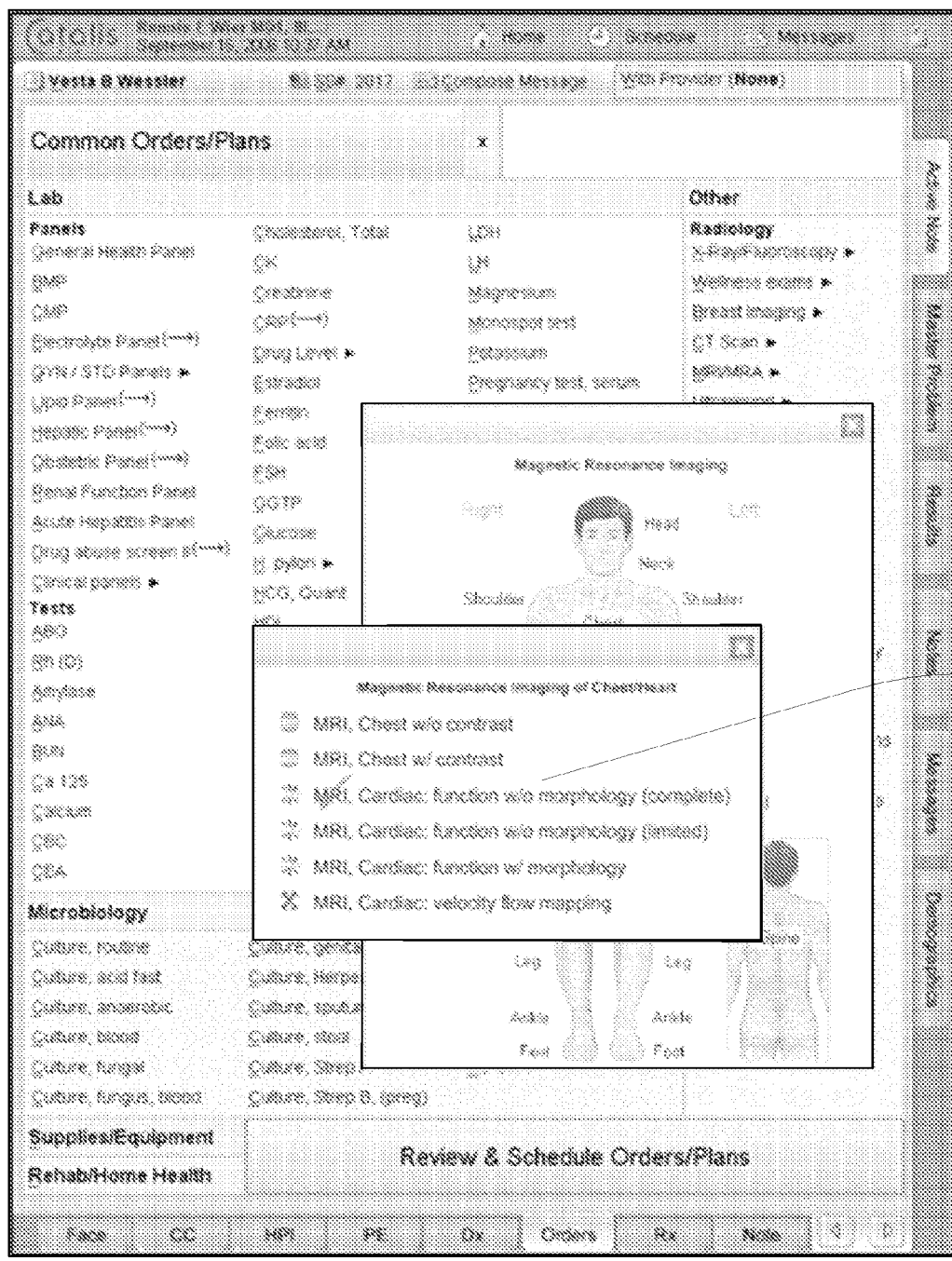
Figure 62:
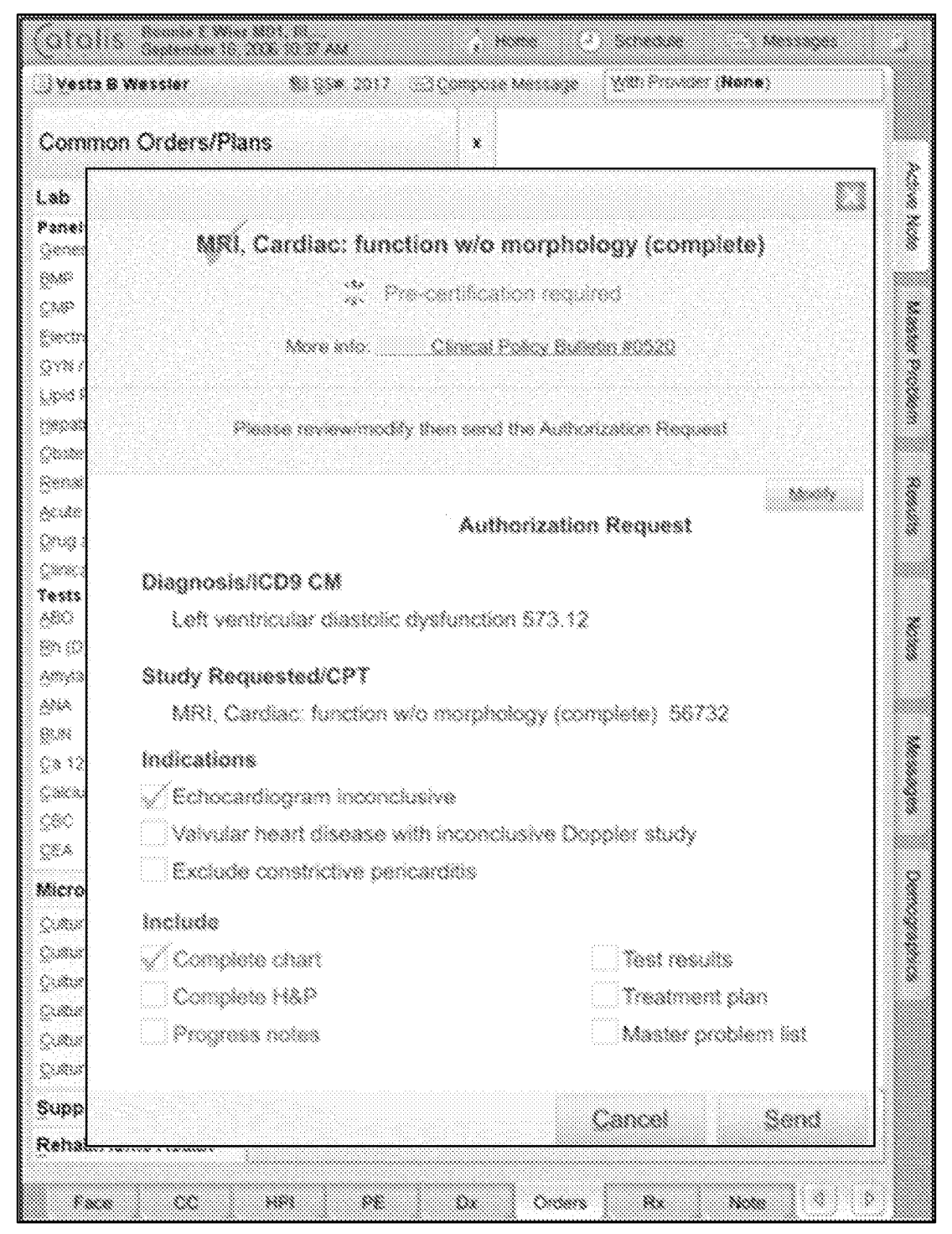

In an example illustrated in FIG. 61, a user may select an order item 6102 that uses precertification by the patient's payer. The system may display criteria for precertification by the payer as illustrated in FIG. 62. In such an embodiment, the system may display the selected order and findings relevant to the pre-certification criteria. For example, in FIG. 62, the system may display the diagnosis stored for the current patient and it also may display findings that bear on the precertification decision for the order to be approved in the context of the diagnosis. For example, some or all findings may be displayed as selectable items. Such selectable items may be coupled to the rest of the EHR system such that (1) the initially displayed state of these findings corresponds to the state of the finding as entered in other phases of the encounter via the EHR system and (2) updates to the state of these findings are stored in the EHR system and can be displayed by navigating to other tasks (such as HPI, ROS, or physical exam.)

In a further embodiment, the system also may provide an interface, as illustrated in FIG. 62, to specify what subset of findings to transmit with the request. Typically, the request includes the requested order and parameters and the findings that are specified in the payer's authorization rules for the order. In particular, the request may include a set of indications items that may be selected or deselected. The set of indications items may be determined based at least in part on the payer's authorization rules. In another example, the user also may wish to transmit additional information, such as the complete chart, the complete history and physical, progress notes, test results, treatment plan, master problem list, or any combination thereof. As illustrated, such additional data may be included in the transmission by checking one or more boxes. For example, such boxes or controls may represent a set of medical findings to be included with the request in addition to the order data. In particular example, one or more of the check boxes, indicating a set of medical findings or a indication, may be preselected, for example, based at least in part on the payer's authorization rules or based at least in part on the medical findings associated with the patient. In an embodiment, the interface also may include an interface to enter a text note or annotation to augment the request. Further, the system may provide in interface displaying the full request as it is to be sent based on the currently selected items, allowing a user to verify the information to be sent. In addition, the interface may include a "modify" control. When the "modify control" is selected, further interfaces may be displayed that permit the user to select or deselect information that is to be transmitted as part of the authorization request. In a particular example, selection of the "modify" control may lead to an interface that includes a selectable item, such as a check box, associated with each of the medical findings to be transmitted with the authorization request in addition to the order data and may include access to additional interfaces, such as those described above for entering medical findings, for selecting additional medical findings to be included with the authorization request.

When the user completes selecting information to be transmitted and findings, the system may transmit the request to the payer. For example, the interface may include a send control or button. In particular, when the send button is selected, the system may prepare and transmit an authorization request to a payer system. The authorization request may include order data, indications data, and optionally additional findings data specified by the HCP.

Figure 63:
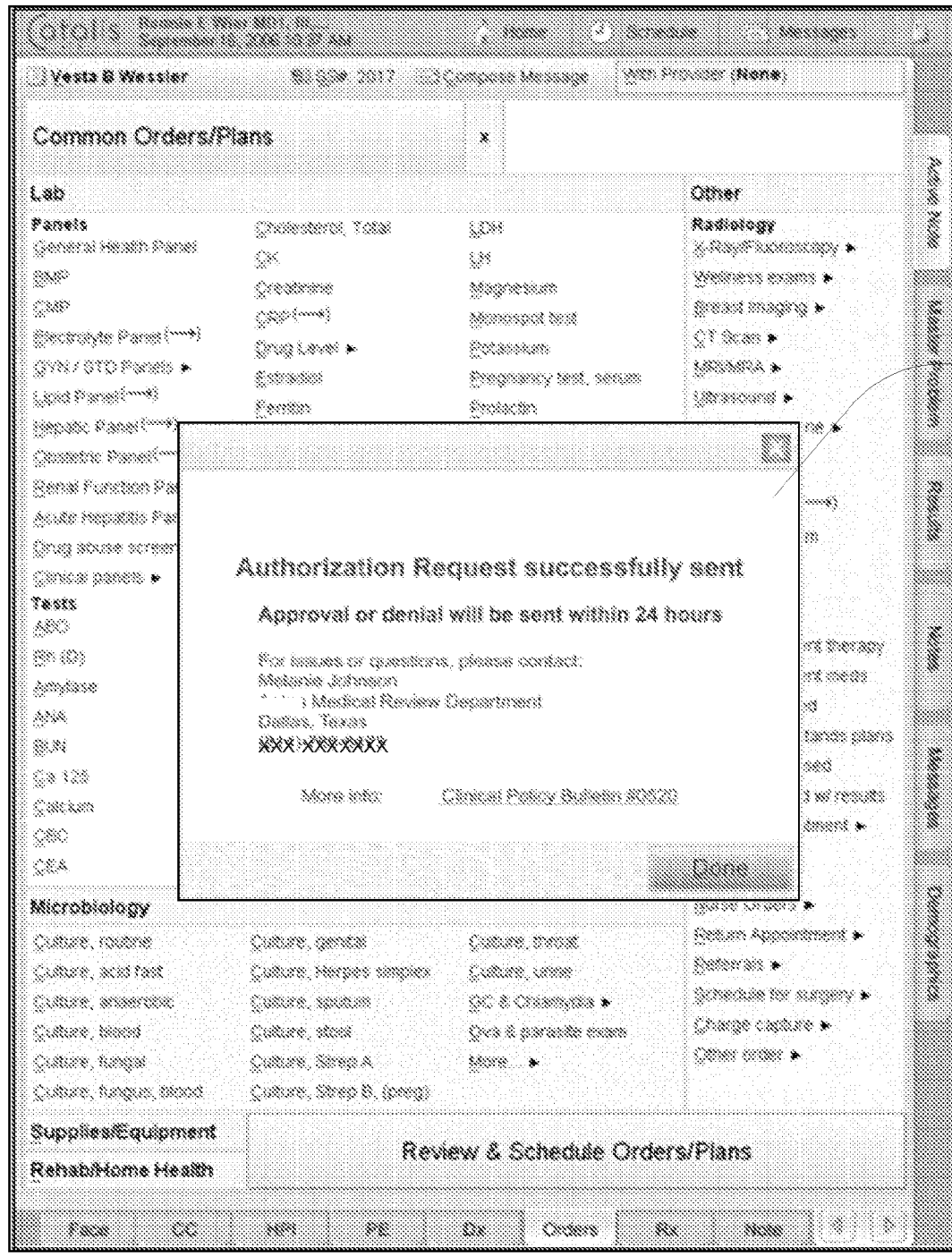

In an exemplary embodiment illustrated in FIG. 63, the system may display an acknowledgement 6302. In an embodiment, the acknowledgement may include a reference number or contact information to allow direct communication with the payer regarding this case. In another embodiment, the system may store the specific payer policy that is relevant to pre-approval for an order and may provide an interface or link for the clinic staff to later retrieve and display this information.

In an exemplary embodiment, upon reception of a precertification request, a payer system may execute an evaluation procedure, such as an automatic evaluation procedure, that evaluates the findings and request against payer policy and responds with an authorization when the request meets specified criteria. Conversely, when the request fails to meet the specified criteria, the request may be displayed by a remote computer so that a human or board can evaluate the request, or a rejection may be transmitted directly to the EHR system. In another exemplary embodiment, requests may be displayed to humans at the payer.

When an order is to be evaluated by a medical review board at the payer because the HCP believes the order is medically necessary even though the order does not meet the standard criteria used by the payer, the system may notify the user that an order is to be reviewed and may assist in completing and transmitting an authorization request based on medical findings received and stored for the patient. Furthermore, such functionality may immediately notify the payer that the item is to be considered and eliminates call/fax authorization requests.

Figure 64:
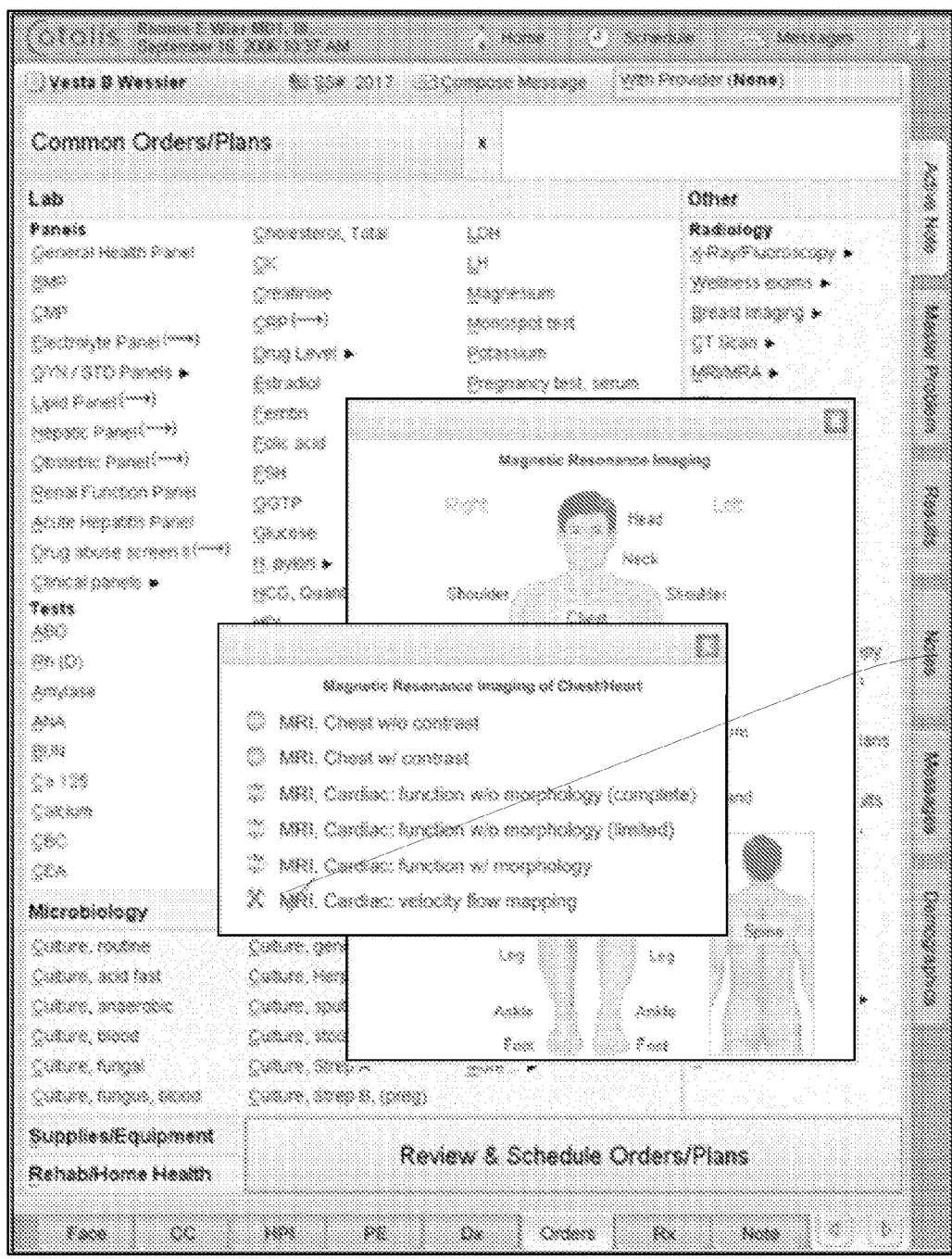
Figure 65:
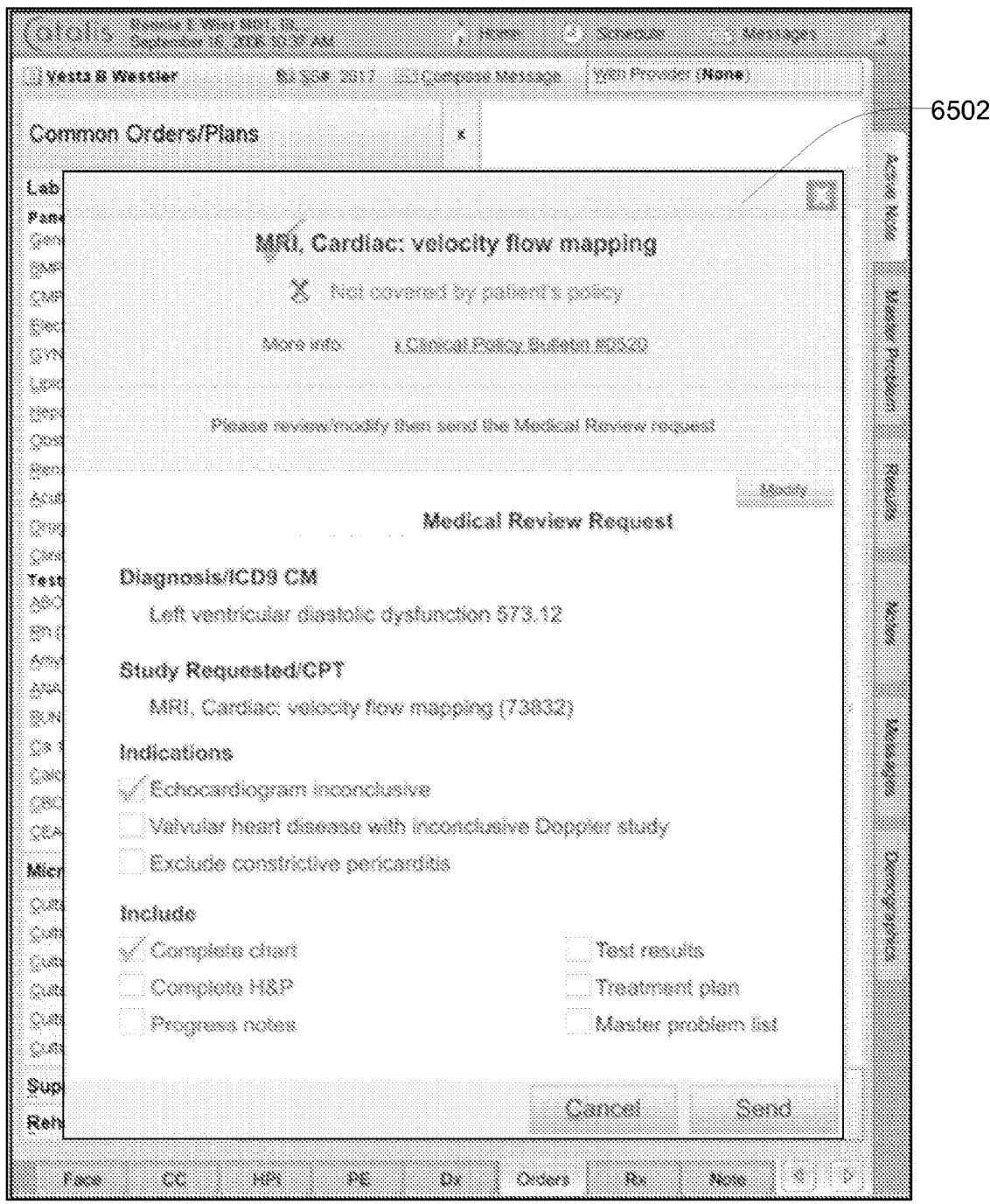

In an exemplary embodiment illustrated in FIG. 64, the user may select an order item 6402 that is not routinely covered by the patient's payer. The system may display an interface 6502 to initiate a medical review request, as illustrated in FIG. 65. In addition, the system may display the selected order and findings relevant to the review request.

In a particular embodiment, the system may not have a rule that describes the routine approval process for the order. As such, the system may use other approaches to determine what findings to transmit. In an exemplary embodiment, the system may use a generic (system-wide or per-provider) rule for determining which findings to include. For example, in FIG. 65, the system may display an request interface and may include in the request the diagnosis stored for the current patient. In addition, the interface may include a "modify" control for adding or deleting findings to be transmitted to the payer.

Figure 66:
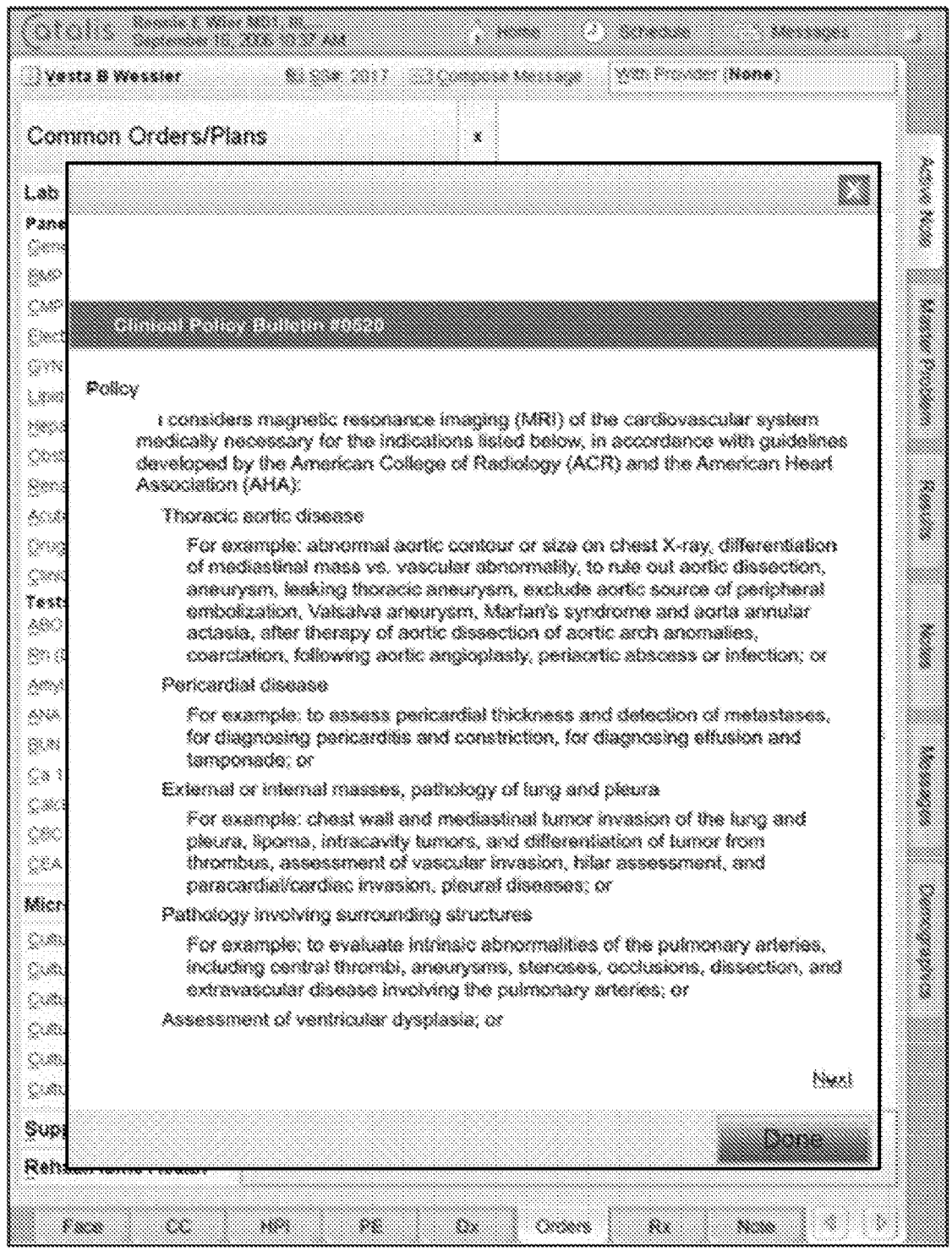

In another embodiment, the system may store payer-specific policies in a human-readable form and may provide an interface to review a payer's policy relevant to a particular order. FIG. 66 includes an illustration of an exemplary payer policy. Such an interface may allow the user to consider which information will be considered relevant by the payer's review board.

In another embodiment, such payer policies are realized as formal rules that are stored in the system. Such rules specify one or more findings whose state is commonly relevant to review board deliberations/requests for exceptions for a given order. FIG. 65 includes an interface in which a set of findings that often are considered in requests for exceptions on board approval requests of "MRI, Cardiac: velocity flow mapping" orders. Such findings generally relate to situations in which the MRI test is medically necessary for a patient.

Further, the system also may provide an interface and controls, as illustrated in FIG. 65, to specify which pre-defined subsets of findings to transmit with the request. In addition, the system may provide an interface to view the request as it will be sent based on the selected items.

When the user completes selecting information to be transmitted, the system may transmit the request to the payer. In an embodiment, the system may display an acknowledgement. For example, the acknowledgement may include a reference number or contact information to allow direct communication with the payer regarding this case. In an embodiment, the system may store the specific payer policy that is relevant to pre-approval for an order and may provide an interface or link for the clinic staff to later retrieve and display this information. In an example, an order sent for approval or review is associated with a reference number that allows the payer to be queried about the request or that allows the payer to query the HCP clinic about the request. Furthermore, the reference number may allow an electronic approval/denial decision to be received by the system and matched with the request so that the decision can be displayed when the HCP reviews the patient's chart.

In a particular embodiment, a method of formulating a medical order for a patient transmitting a medical order interface to a healthcare provider interface device. The medical order interface includes a plurality of selectable medical order items. The method further includes, in response to receiving a selection of a medical order item of the plurality of selectable medical order items, transmitting a payer request interface to the healthcare provider interface device. The payer request interface includes a set of selectable findings controls. Each selectable findings control of the set of selectable findings controls is associated with a set of medical findings associated with the patient. The payer request interface includes a send control. In addition, the method includes, in response to receiving a selection of a select findings control and receiving selection of the send control, sending an electronic payer request. The electronic payer request includes the set of medical finding associated with the select findings control and order data associated with the medical order item.

In another exemplary embodiment, a method of formulating a medical order for a patient includes storing a plurality of medical findings associated with a patient on an electronic storage medium, and storing a set of payer authorization rules associated with a payer. The patient is associated with the payer. The method further includes transmitting a medical order interface to a healthcare provider interface device. The medical order interface includes a plurality of selectable medical order items. In response to receiving a selection of a medical order item of the plurality of selectable medical order items, a payer request interface is transmitted to the healthcare provider interface device based at least in part on the set of payer authorization rules associated with the payer. The payer request interface includes a set of selectable indications items. The set of selectable indications items is based at least in part on the set of payer authorization rules. The payer request interface includes a send control. In response to receiving a selection of a select indications item and receiving selection of the send control, an electronic payer request is sent to a payer system. The electronic payer request includes order data associated with the selected medical order item and indications data associated with the select indications item.

In a further exemplary embodiment, a system includes processor-accessible storage including a set of authorization rules associated with a payer plan, patient information associating a patient associated with the payer plan, and patient medical findings associated with the patient. The system also includes computer implemented instructions operable by a processor to transmit a medical order interface to a healthcare provider interface device. The medical order interface includes a plurality of selectable medical order items. The system further includes computer implemented instructions operable by a processor to transmit a payer request interface to the healthcare provider interface device based at least in part on the set of payer authorization rules associated with the payer in response to receiving a selection of a medical order item of the plurality of selectable medical order items. The payer request interface includes a set of selectable indications items. The set of selectable indications items is based at least in part on the set of payer authorization rules. The payer request interface includes a send control. In addition, the system includes computer implemented instructions operable by a processor to send an electronic payer request to the payer in response to receiving a selection of a select findings control and receiving selection of the send control. The payer request includes order data associated with the selected medical order item and includes indications data associated with the selected indications item.

In general, the interfaces presented above may be implemented using one or more of various interface programming techniques, including hypertext markup language, Flash, Visual Basic, Visual C, JAVA, .NET or any combination thereof, among others. Each interface may include buttons, radio-buttons, check-boxes, tri-state controls, links, text boxes, and menus, or any combination thereof, each of which is referred to as a control or selectable item.

Data received through the interfaces described above may be transmitted to one or more servers and may be stored on one or more electronic storage media, such media and media types being well know to those of skill in the art. In particular, the stored data may include patient medical findings, order data, order request, authorization requests, response to order request and authorization request, payer authorization rules, or any combination thereof. In particular, the system may include more than one set of payer authorization rules, each set being associated with a different third-party payer.

The above-disclosed subject matter is to be considered illustrative, and not restrictive, and the appended claims are intended to cover all such modifications, enhancements, and other embodiments, which fall within the true scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A method of formulating a medical order for a patient, the method comprising:
   transmitting a medical order interface to a healthcare provider interface device, the medical order interface including a plurality of selectable medical order items;
   in response to receiving a selection of a medical order item of the plurality of selectable medical order items, transmitting an authorization request interface to the healthcare provider interface device, the authorization request interface associated with an electronic authorization request for authorization from a third party payer, the authorization request interface including a set of selectable findings controls, each selectable findings control of the set of selectable findings controls associated with a set of medical findings associated with the patient, at least one set of medical findings associated with a selectable findings control including a subset of medical findings less than a full set of medical findings associated with the patient, the authorization request interface including a send control; and in response to receiving a selection of a select findings control and receiving selection of the send control, sending the electronic authorization request to request authorization for a medical order associated with the selected medical order item from the third party payer, the electronic authorization request including the set of medical findings associated with the select findings control and order data associated with the medical order item.

2. The method of claim 1, further comprising:
storing a plurality of medical findings associated with the patient on electronic storage media; and
storing a set of payer authorization rules associated with a payer on the electronic storage media, the patient associated with the payer.

3. The method of claim 2, wherein transmitting the authorization request interface includes transmitting the authorization request interface based at least in part on the set of payer authorization rules associated with the payer associated with the patient.

4. The method of claim 2, wherein the authorization request interface further comprises a modify control, the method further comprising:
transmitting a further findings interface to the healthcare provider interface device in response to receiving a selection of the modify control, the further findings interface including a second set of selectable medical findings controls based at least in part on the plurality of medical findings.

5. The method of claim 3, wherein the authorization request interface includes a set of selectable indications items, the set of selectable indications items based at least in part on the set of payer authorization rules.

6. The method of claim 3, further comprising determining an authorization status associated with the selected medical order item based at least in part on the payer authorization rules.

7. The method of claim 3, further comprising determining an authorization status associated with the selected medical order item based at least in part on the stored plurality of medical findings associated with the patient.

8. The method of claim 3, further comprising, in the authorization request interface, pre-selecting a selectable findings control of the set of selectable findings controls based at least in part on the set of payer authorization rules.

9. The method of claim 5, wherein a selectable indications item is associated with an inconclusive test result.

10. The method of claim 1, further comprising receiving the order data associated with the medical order item.

11. A method of formulating a medical order for a patient, the method comprising:
storing a plurality of medical findings associated with a patient on an electronic storage media;
storing a set of payer authorization rules associated with a payer on the electronic storage media, the patient associated with the payer;
transmitting a medical order interface to a healthcare provider interface device, the medical order interface including a plurality of selectable medical order items;
in response to receiving a selection of a medical order item of the plurality of selectable medical order items, determining an authorization status;
based on the authorization status, transmitting an authorization request interface to the healthcare provider interface device based at least in part on the set of payer authorization rules associated with the payer, the authorization request interface associated with an electronic authorization request for authorization from the payer, the authorization request interface including a set of selectable indications items, the set of selectable indications items based at least in part on the set of payer authorization rules, at least one of the set of selectable indications items indicating an inconclusive result of a test, the authorization request interface including a send control; and in response to receiving a selection of a select indications item and receiving selection of the send control, sending the electronic authorization request to request authorization for a medical order associated with the selected medical order item to a payer system associated with the payer, the electronic authorization request including order data associated with the selected medical order item and indications data associated with the select indications item.

12. The method of claim 11, further comprising receiving the order data associated with the selected medical order item.

13. The method of claim 11, wherein determining the authorization status includes determining the authorization status based at least in part on the stored set of payer authorization rules and based at least in part on the stored plurality of medical findings associated with the patient.

14. The method of claim 11, wherein the authorization request interface further comprises a modify control, the method further comprising:
transmitting a further findings interface to the healthcare provider interface device in response to receiving a selection of the modify control, the further findings interface including a set of selectable medical findings controls based at least in part on the plurality of medical findings.

15. The method of claim 11, further comprising, in the authorization request interface, pre-selecting a selectable indications item of the set of selectable indications items based at least in part on the plurality of medical findings.

16. The method of claim 11, wherein the authorization request interface includes a set of medical findings controls, the method further comprising, in the authorization request interface, pre-selecting a medical findings control of the set of medical findings controls, at least one medical findings control of the set of medical findings controls associated with a subset of medical findings less than a full set of medical findings associated with the patient.

17. A system comprising:
processor-accessible storage including a set of authorization rules associated with a payer plan, patient information associating a patient with the payer plan, and patient medical findings associated with the patient; and
computer implemented instructions operable by a processor to transmit a medical order interface to a healthcare provider interface device, the medical order interface including a plurality of selectable medical order items;
computer implemented instructions operable by a processor to transmit an authorization request interface to the healthcare provider interface device based at least in part on the set of payer authorization rules associated with the payer plan in response to receiving a selection of a medical order item of the plurality of selectable medical order items, the authorization request interface associated with an electronic authorization request for authorization from the payer, the authorization request interface including a set of selectable indications items, the set of selectable indications items based at least in part on the set of payer authorization rules, at least one of the set of selectable indications items indicating an incon clusive result of a test, the authorization request interface including a send control; and computer implemented instructions operable by a processor to send the electronic authorization request to request authorization for a medical order associated with the selected medical order item to the payer in response to receiving a selection of a select findings control and receiving selection of the send control, the electronic authorization request including order data associated with the selected medical order item and including indications data associated with the selected indications item.

18. The system of claim 17, further comprising computer implemented instructions operable by a processor to receive order data associated with the selected medical order item.

19. The system of claim 17, further comprising computer implemented instructions operable by a processor to determine an authorization status based at least in part on the stored set of payer authorization rules and based at least in part on the stored plurality of medical findings associated with the patient.

20. The system of claim 17, wherein the authorization request interface further comprises a modify control, the system further comprising:

computer implemented instructions operable by a processor to transmit a further findings interface to the healthcare provider interface device in response to receiving a selection of the modify control, the further findings interface including a set of selectable medical findings controls based at least in part on the plurality of medical findings.

* * * * *